(12) United States Patent
Abdou

(10) Patent No.: US 7,842,074 B2
(45) Date of Patent: Nov. 30, 2010

(54) SPINAL STABILIZATION SYSTEMS AND METHODS OF USE

(76) Inventor: M. Samy Abdou, 7790 Doug Hill, San Diego, CA (US) 92127

( * ) Notice: Subject to any disclaimer, the term of this patent is extended or adjusted under 35 U.S.C. 154(b) by 527 days.

(21) Appl. No.: 12/072,695

(22) Filed: Feb. 26, 2008

(65) Prior Publication Data
US 2008/0243186 A1 Oct. 2, 2008

Related U.S. Application Data

(60) Provisional application No. 60/903,486, filed on Feb. 26, 2007, provisional application No. 60/921,570, filed on Apr. 3, 2007, provisional application No. 60/926,839, filed on Apr. 30, 2007.

(51) Int. Cl.
*A61B 17/88* (2006.01)
(52) U.S. Cl. .................. 606/279; 606/99
(58) Field of Classification Search .......... 606/86 A, 606/86 B, 99, 246, 248–272, 278, 279; 623/17.11–17.16
See application file for complete search history.

(56) References Cited

U.S. PATENT DOCUMENTS

| | | | |
|---|---|---|---|
| 4,554,914 A | 11/1985 | Kapp et al. |
| 4,611,582 A | 9/1986 | Duff |
| 5,011,484 A | 4/1991 | Breard |
| 5,234,432 A | 8/1993 | Brown |
| 5,250,055 A | 10/1993 | Moore et al. |
| 5,261,910 A | 11/1993 | Warden et al. |
| 5,304,178 A | 4/1994 | Stahurski |
| 5,496,318 A | 3/1996 | Howland et al. |
| 5,609,634 A | 3/1997 | Voydeville |
| 5,645,599 A | 7/1997 | Samani |
| 5,725,582 A | 3/1998 | Bevan et al. |
| 5,836,948 A | 11/1998 | Zucherman et al. |
| 5,860,977 A | 1/1999 | Zucherman et al. |
| 6,312,431 B1 | 11/2001 | Asfora |
| 6,582,433 B2 | 6/2003 | Yun |
| 7,048,736 B2 | 5/2006 | Robinson et al. |
| 2006/0015181 A1 | 1/2006 | Elberg |
| 2006/0036246 A1 | 2/2006 | Carl et al. |
| 2006/0085069 A1 | 4/2006 | Kim |
| 2006/0089646 A1 | 4/2006 | Bonutti |
| 2006/0149278 A1 | 7/2006 | Abdou |
| 2006/0235387 A1 | 10/2006 | Peterman |
| 2006/0241614 A1 | 10/2006 | Bruneau et al. |
| 2007/0162001 A1 | 7/2007 | Chin et al. |

(Continued)

OTHER PUBLICATIONS

Wang et al. "SPIRE spinous process stabilization plate: biomechanical evaluation of a novel technology" *J. Neurosurgery Spine* 4(2): 160-4 (2006).

(Continued)

*Primary Examiner*—Eduardo C Robert
*Assistant Examiner*—Christina Negrelli
(74) *Attorney, Agent, or Firm*—Fred C. Hernandez; Mintz, Levin, Cohn, Ferris, Glovsky and Popeo, P.C.

(57) ABSTRACT

Devices and methods are adapted to permit fixation and stabilization of the bony elements of the skeleton. The devices permit adjustment and maintenance of the spatial relationship between neighboring bones. The motion between adjacent skeletal segments may be maintained, limited or completely eliminated.

20 Claims, 61 Drawing Sheets

U.S. PATENT DOCUMENTS

| | | |
|---|---|---|
| 2007/0179500 A1 | 8/2007 | Chin et al. |
| 2007/0233082 A1 | 10/2007 | Chin et al. |
| 2007/0270840 A1 | 11/2007 | Chin et al. |
| 2008/0183211 A1 | 7/2008 | Lamborne et al. |
| 2008/0183218 A1 | 7/2008 | Mueller et al. |

OTHER PUBLICATIONS

Wang et al. "Comparison of CD Horizon SPIRE spinous process plate stabilization and pedicle screw fixation after anterior lumbar interbody fusion" *J. Neurosurgery Spine* 4(2): 132-6 (2006).

Andersen T. et al., "Pain 5 years after instrumented and non-instrumented posterolateral lumbar spinal fusion" Eur Spine J Aug. 2003;12(4):393-9. Epub May 20, 2003.

Asazuma T. et al., "Intersegmental spinal flexibility with lumbosacral instrumentation. An in vitro biomechanical investigation" Spine (Phila PA 1976) Nov. 1990; 15(11):1153-8.

Bendo J.A. et al., "Instrumented posterior arthrodesis of the lumbar spine in patients with diabetes mellitus" Am J Orthop (Belle Mead NJ) Aug. 2000;29(8):617-20.

Benz R.J. et al., "Current techniques of decompression of the lumbar spine" Clin Orthop Relat Res Mar. 2001;(384):75-81.

Branch C.L., "Posterior lumbar interbody fusion with the keystone graft: technique and results" Surg Neurol May 1987;27(5):449-54.

Chen W. et al., "Surgical treatment of adjacent instability after lumbar spine fusion" Spine (Phila Pa 1976) Nov. 15, 2001;26(22):E519-24.

Chiba M. et al., "Short-segment pedicle instrumentation. Biomechanical analysis of supplemental hook fixation" Spine (Phila Pa 1976) Feb. 1, 1996;21(3):288-94.

Cobo Soriano J. et al., "Predictors of outcome after decompressive lumbar surgery and instrumented posterolateral fusion" Eur Spine J Feb. 5, 2010; [Epub ahead of print].

Dawson E.G. et al., "Intertransverse process lumbar arthodesis with autogenous bone graft" Clin Orthop Relat Res Jan.-Feb. 1981;(154):90-6.

Deguchi M. et al., "Biomechanical comparison of spondylolysis fixation techniques" Spine (Phila Pa 1976) Feb. 15, 1999;24(4):328-33.

Dove J., "Internal fixation of the lumbar spine. The Hartshill rectangle" Clin Orthrop Relat Res Feb. 1986;(203):135-40.

Fischgrund J.S. et al., "1997 Volvo Award winner in clinical studies. Degenerative lumbar spondylolisthesis with spinal stenosis: a prospective, randomized study comparing decompressive laminectomy and arthrodesis with and without spinal instrumentation" Spine (Phila Pa 1976) Dec. 15, 1997;22(24):2807-12.

Freeman B.J., et al., "Posterior lumbar interbody fusion combined with instrumented postero-lateral fusion: 5-year results in 60 patients" Eur Spine J Feb. 2000;9(1):42-6.

Gibson J., "Surgery for degenerative lumbar spondylosis" Cochrane Database Syst Rev 2005;(4):CD001352. Epub Oct. 19, 2005.

Gill G.G., "Long-term follow-up evaluation of a few patients with spondylolisthesis treated by excision of the loose lamina with decompression of the nerve roots without spinal fusion" Clin Orthop Relat Res Jan.-Feb. 1984;(182):215-9.

Greenough C.G. et al., "Instrumented posterolateral lumbar fusion. Results and comparison with anterior interbody fusion" Spine (Phila Pa 1976) Feb. 15, 1998;23(4):479-86.

Gunzburg R. et al., "The conservative surgical treatment of lumbar spinal stenosis in the elderly" Eur Spine J Oct. 2003;12 Suppl 2( ):S176-80. Epub Sep. 5, 2003.

Hajek P.D. et al., "Biomechanical study of C1-C2 posterior arthrodesis techniques" Spine (Phila Pa 1976) Feb. 1993;18(2):173-7.

Katz J.N. et al., "Lumbar laminectomy alone or with instrumented or noninstrumented arthrodesis in degenerative lumbar spinal stenosis. Patient selection, costs, and surgical outcomes" Spine (Phila Pa 1976) May 15, 1997;22(10):1123-31.

Krag M.H. et al., "An internal fixator for posterior application to short segments of the thoracic, lumbar, or lumbosacral spine. Design and testing." Clin Orthop Relat Res Feb. 1986; (203):75-98.

Lin P.M., "Internal decompression for multiple levels of lumbar spinal stenosis: a technical note" Neurosurgery Oct. 1982; 11(4):546-9.

Lorenz M. et al., "A comparison of single-level fusions with and without hardware" Spine (Phila PA 1976) Aug. 1991; 16 (8 Suppl): S445-8.

Luque E.R., "Segmental spinal instrumentation of the lumbar spine" Clin Orthop Relat Res Feb. 1986;(203):126-34.

Madan S. et al., "Circumferential and posterolateral fusion for lumbar disc disease" Clin Orthop Relat Res Apr. 2003;(409):114-23.

Madan S. et al., "Outcome of posterior lumbar interbody fusion versus posterolateral fusion for spondylolytic spondylolisthesis" Spine (Phila Pa 1976) Jul. 15, 2002;27(14):1536-42.

O'Leary P.F. et al., "Distraction laminoplasty for decompression of lumbar spinal stenosis" Clin Orthop Relat Res Mar. 2001;(384):26-34.

Polly D. et al., "Surgical treatment for the painful motion segment: matching technology with the indications: posterior lumbar fusion" Spine (Phila Pa 1976) Aug. 15, 2005;30(16 Suppl): S44-51.

Rompe J.D. et al., "Degenerative lumbar spinal stenosis. Long-term results after undercutting decompression compared with decompressive laminectomy alone or with instrumented fusion" Neurosurg Rev Oct. 1999;22(2-3):102-6.

Rousseau M. et al., "Predictors of outcomes after posterior decompression and fusion in degenerative spondylolisthesis" Eur Spine J Feb. 2005;14(1):55-60. Epub Jun. 10, 2004.

Sidhu K.S. et al., "Spinal instrumentation in the management of degenerative disorders of the lumbar spine" Clin Orthop Relat Res Feb. 1997;(335):39-53.

Smith M.D. et al., "A biomechanical analysis of atlantoaxial stabilization methods using a bovine model. C1/C2 fixation analysis" Clin Orthop Relat Res May 1993;(290):285-95.

Stambough J. et al., "Instrumented one and two level posterolateral fusions with recombinant human bone morphogenetic protein-2 and allograft: a computed tomography study" Spine (Phila PA 1976) Jan. 1, 2010; 35(1):124-9.

Stambough J.L., "Lumbosacral instrumented fusion: analysis of 124 consecutive cases" J Spinal Disord Feb. 1999;12(1):1-9.

Swanson K. et al., "The effects of an interspinous implant on intervertebral disc pressures" Spine (Phila Pa 1976) Jan. 1, 2003;28(1):26-32.

Vamvanij V. et al., "Surgical treatment of internal disc disruption: an outcome study of four fusion techniques" J Spinal Disord Oct. 1998;11(5):375-82.

Voor M.J. et al., "Biomechanical evaluation of posterior and anterior lumbar interbody fusion techniques" J Spinal Disord Aug. 1998;11(4):328-34.

Wang J. et al., "Comparison of CD Horizon Spire spinous process plate stabilization and pedicle screw fixation after anterior lumbar interbody fusion. Invited submission from the Joint Section Meeting on Disorders of the Spine and Peripheral Nerves, Mar. 2005" J Neurosurg Spine Feb. 2006; 4(2):132-6.

Wang J. et al., "SPIRE spinous process stabilization plate: biomechanical evaluation of a novel technology. Invited submission from the Joint Section Meeting on Disorders of the Spine and Peripheral Nerves, Mar. 2005" J Neurosurg Spine Feb. 2006;4(2):160-4.

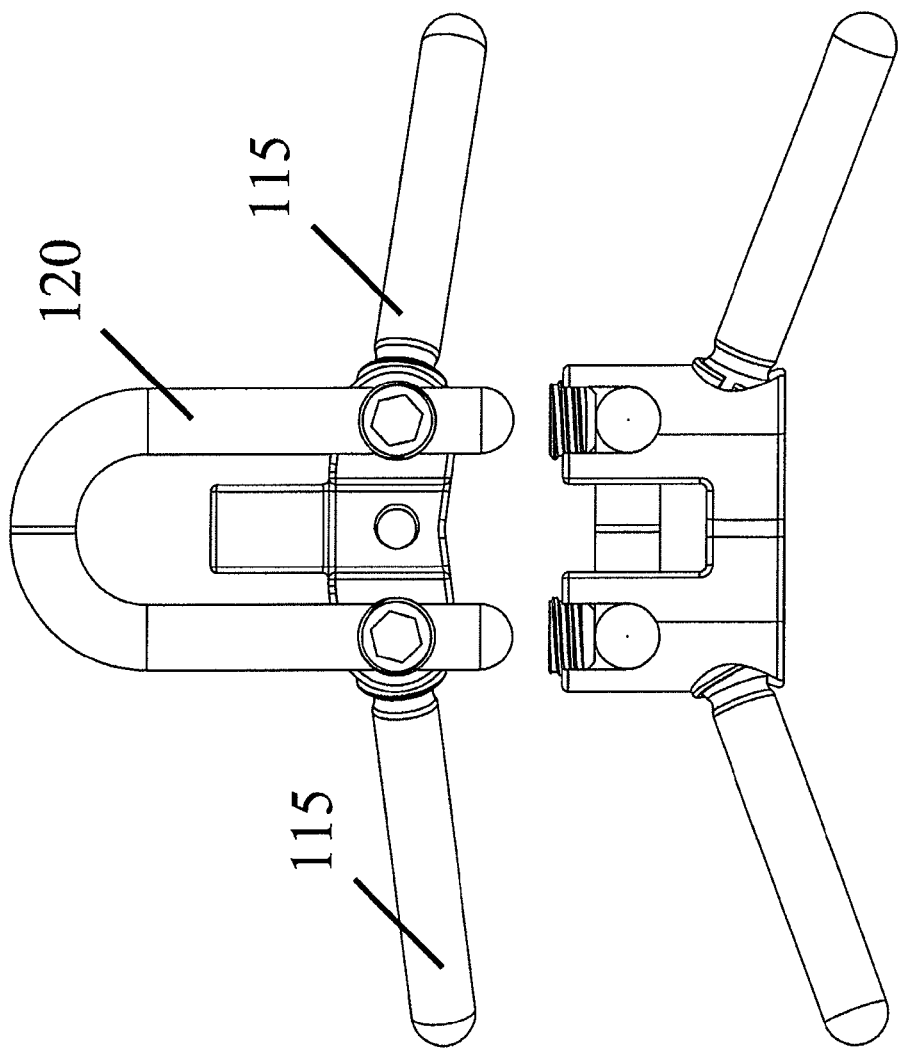
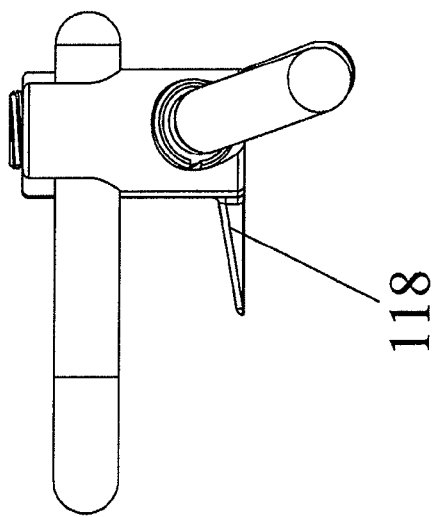
Fig. 2

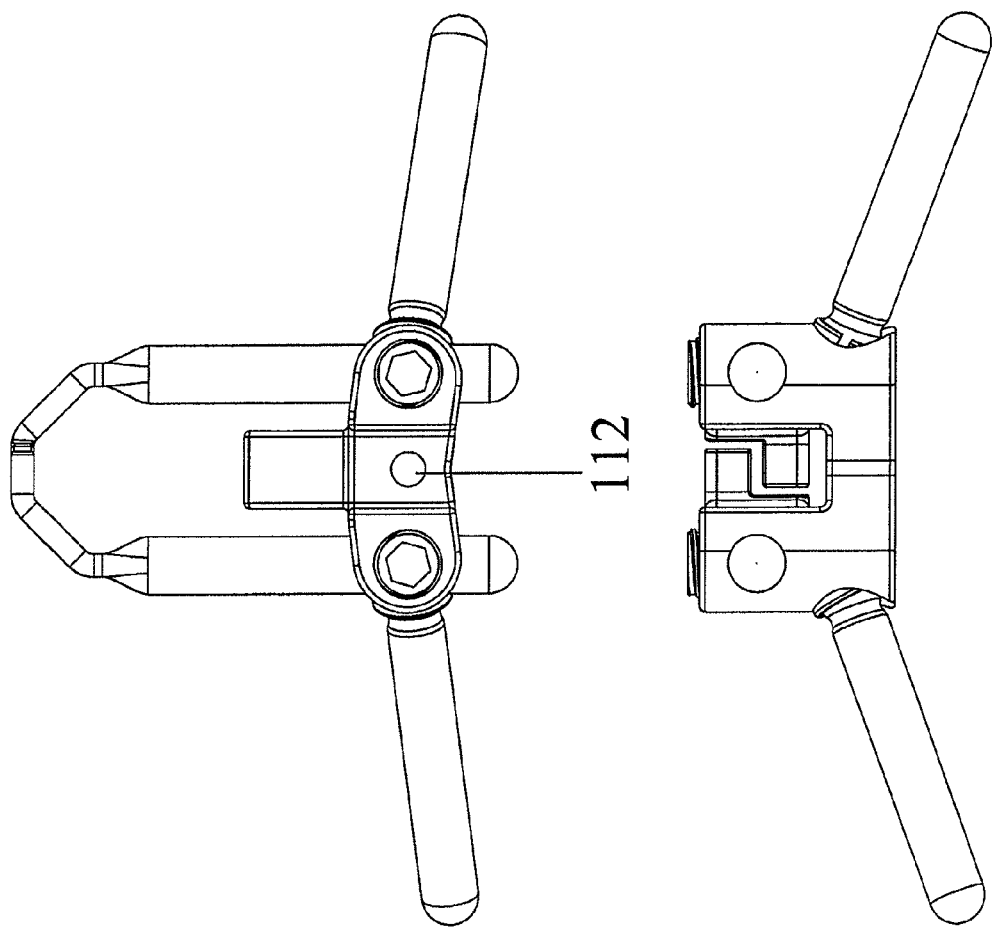
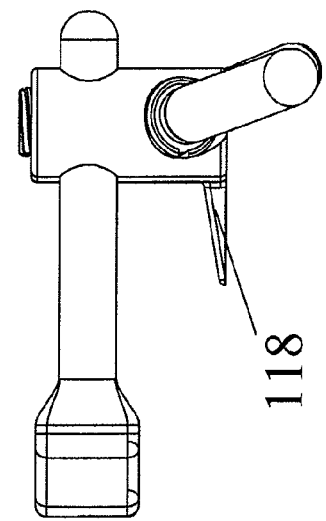
Fig. 7

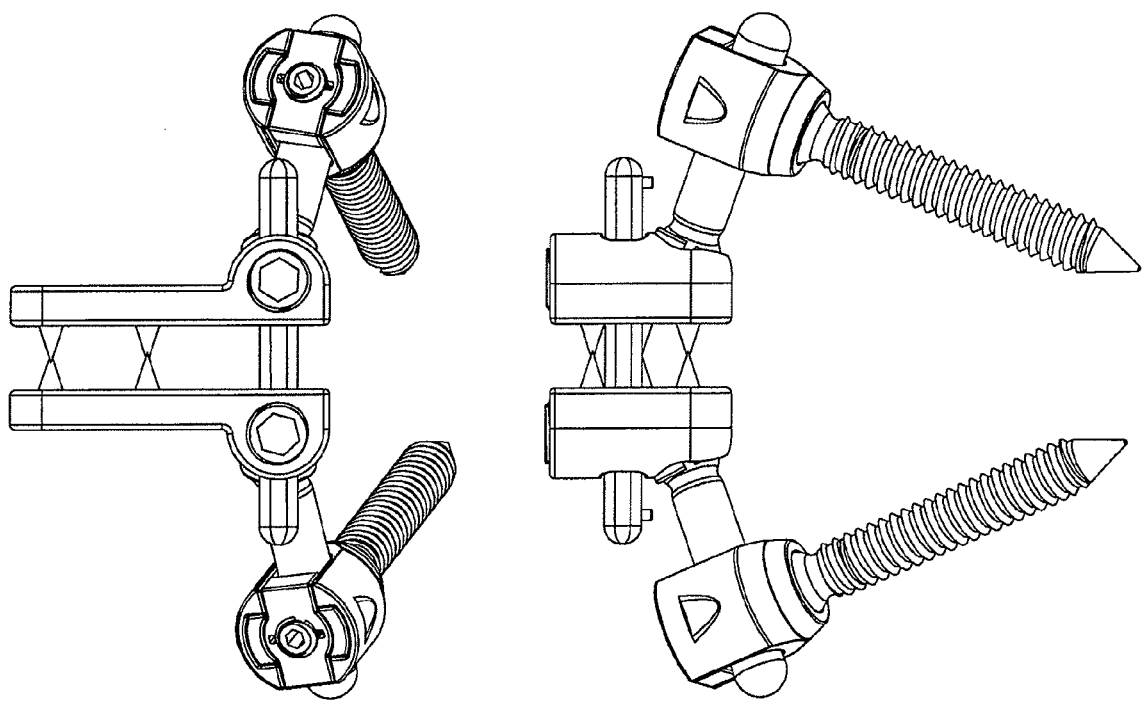
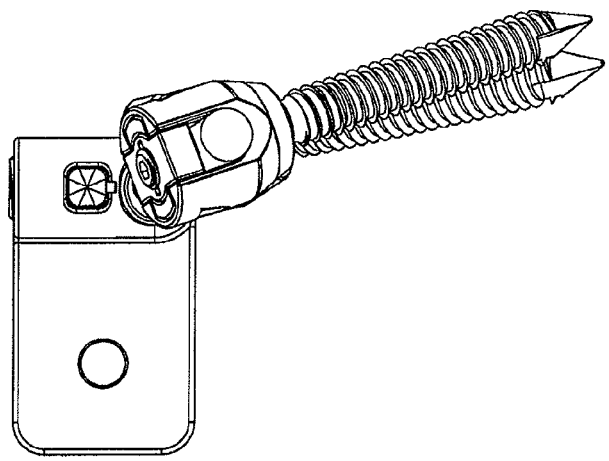
Fig. 12

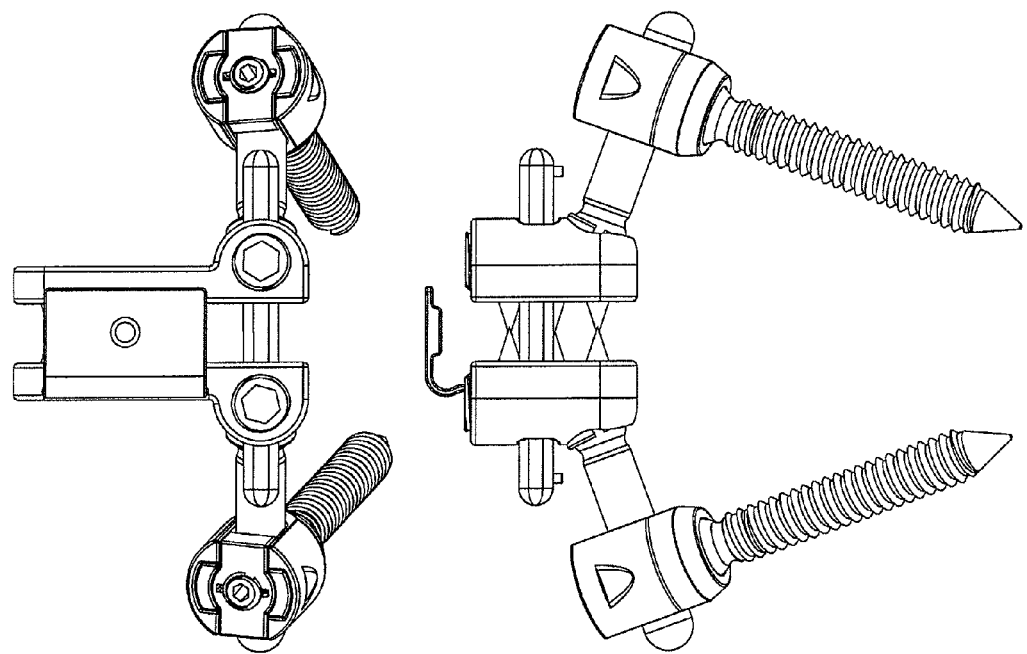
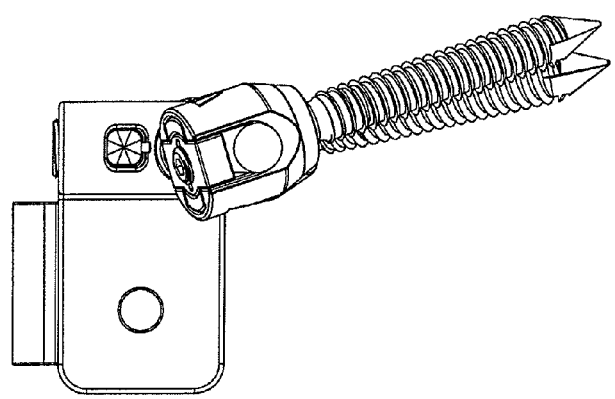
Fig. 24

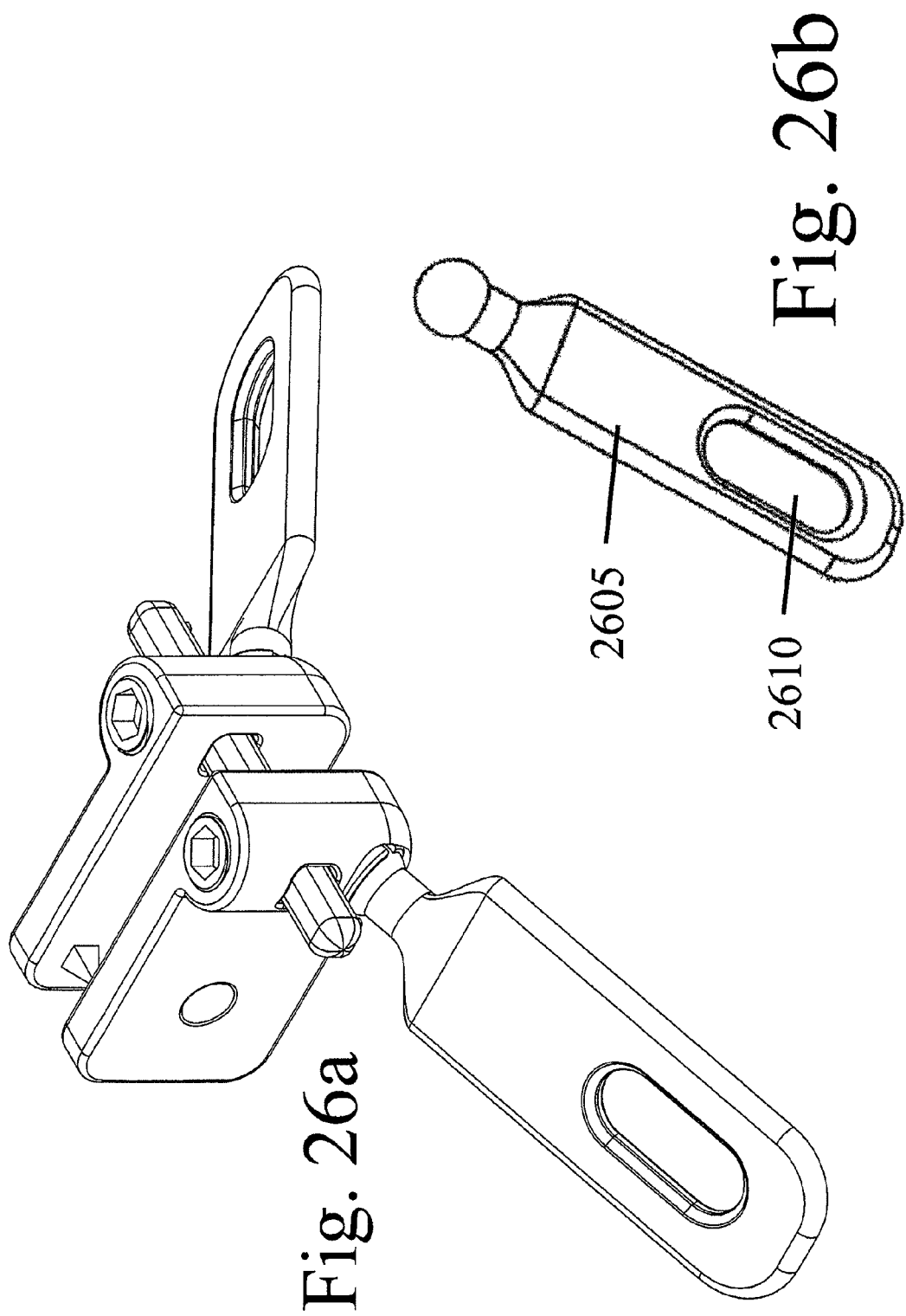

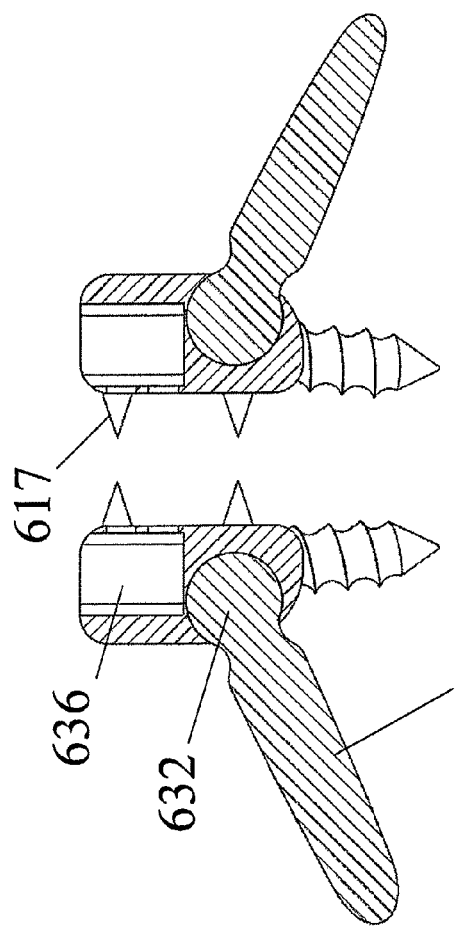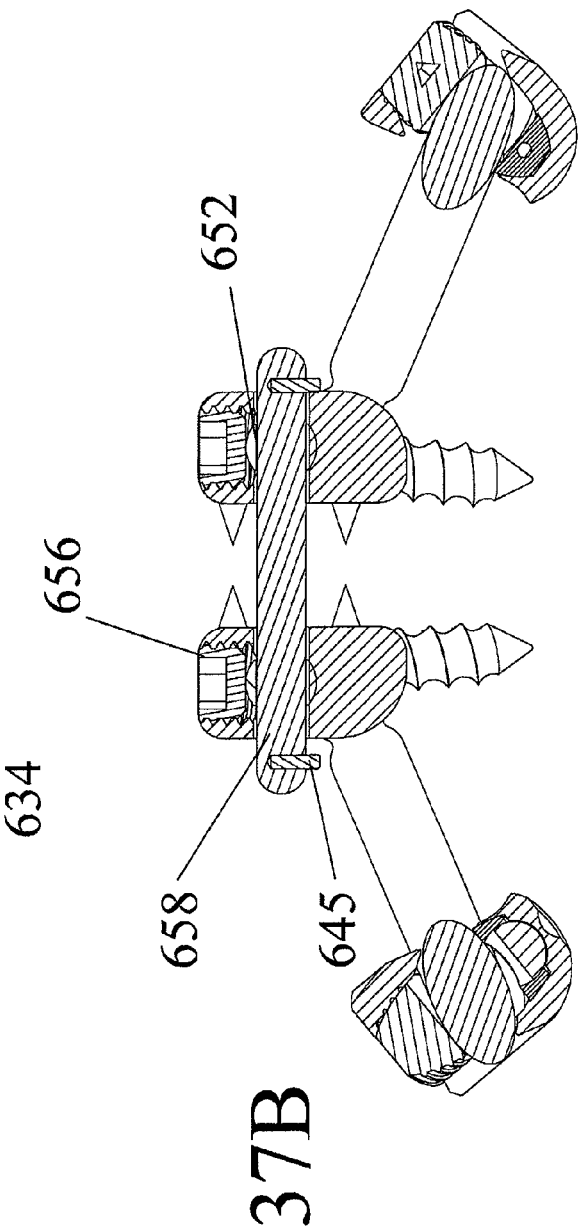
Fig. 37A
Fig. 37B

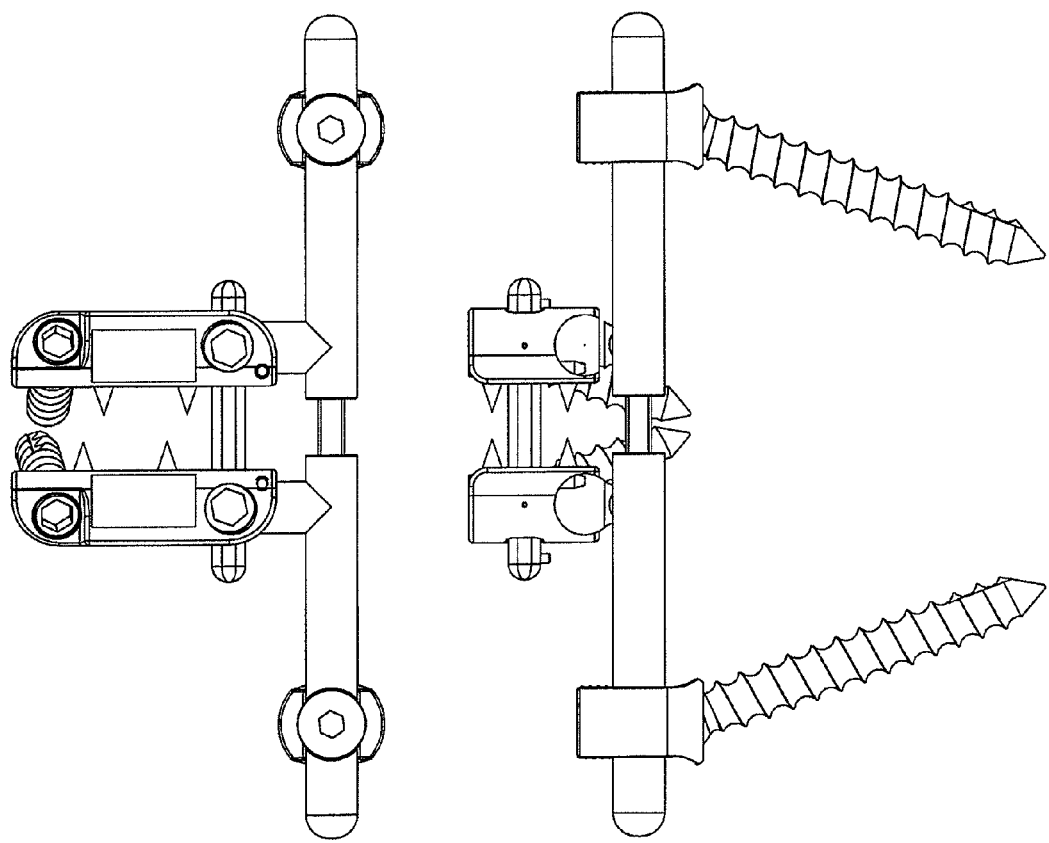
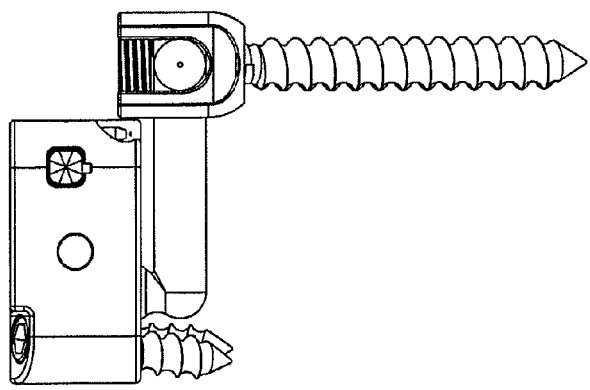
Fig. 39

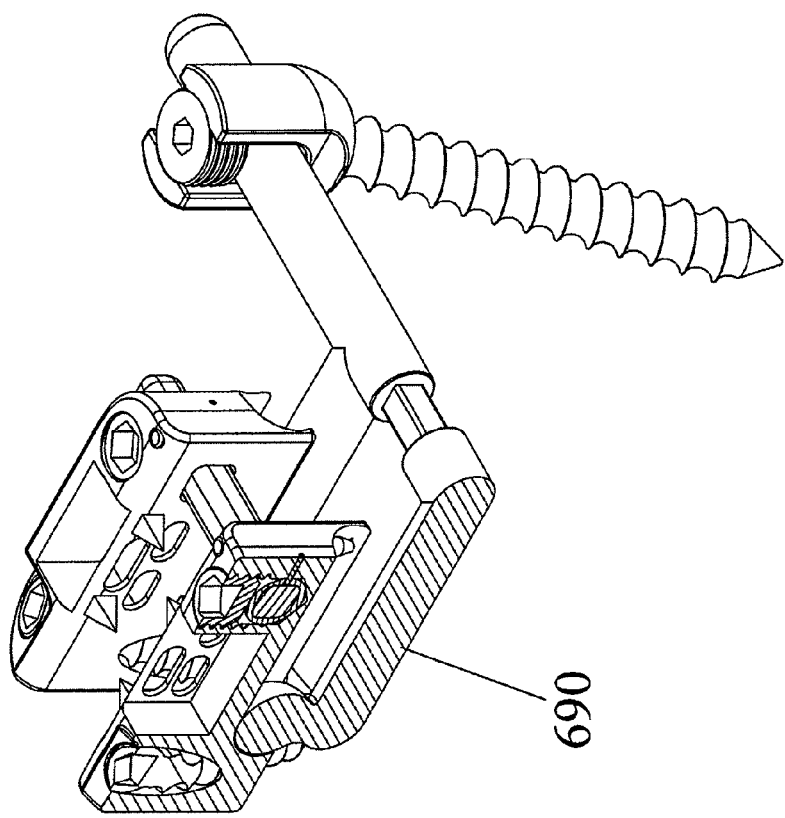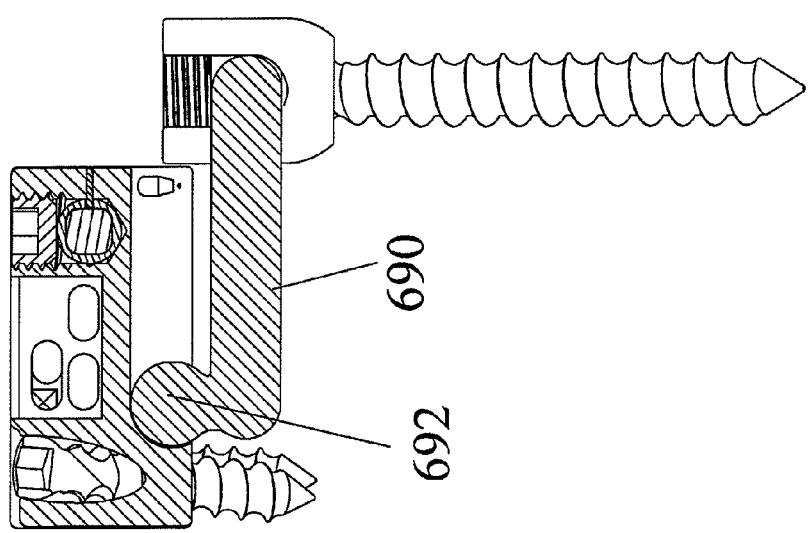
Fig. 42

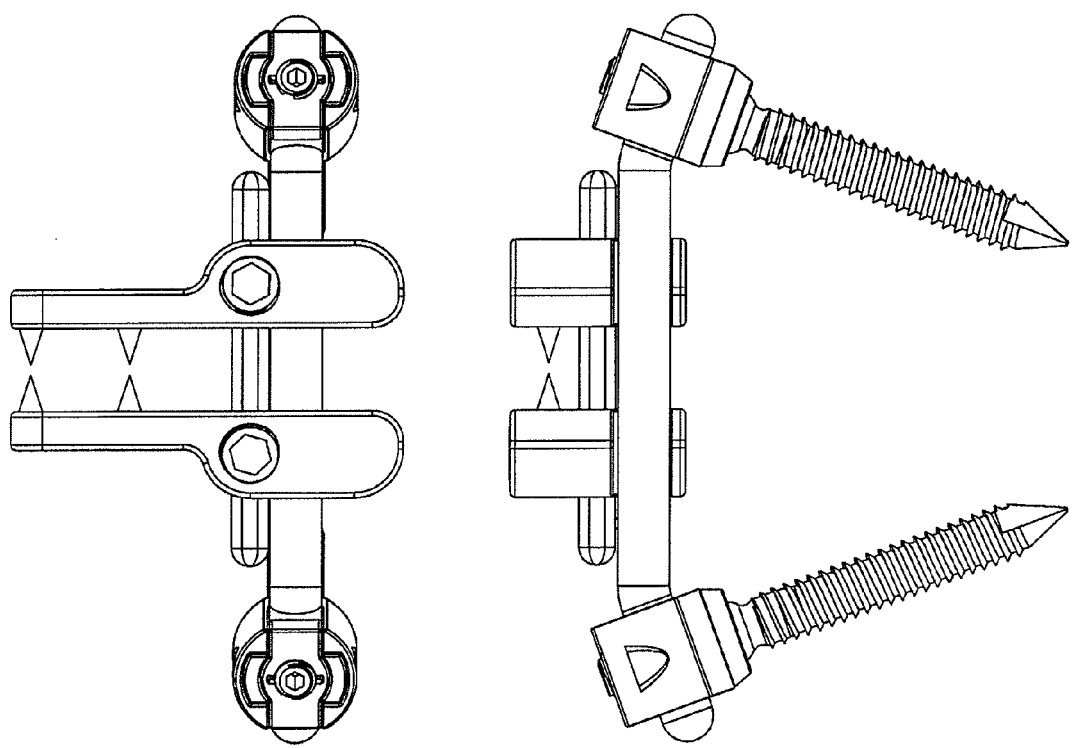
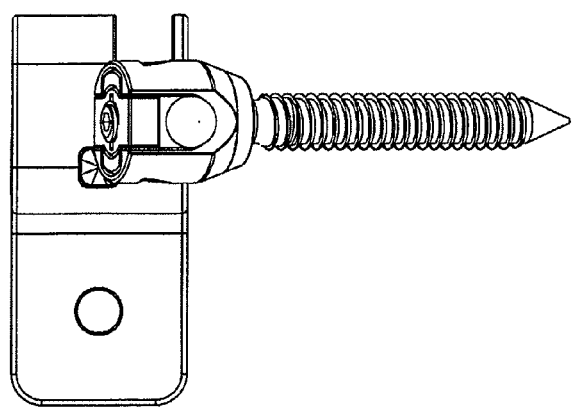
Fig. 46

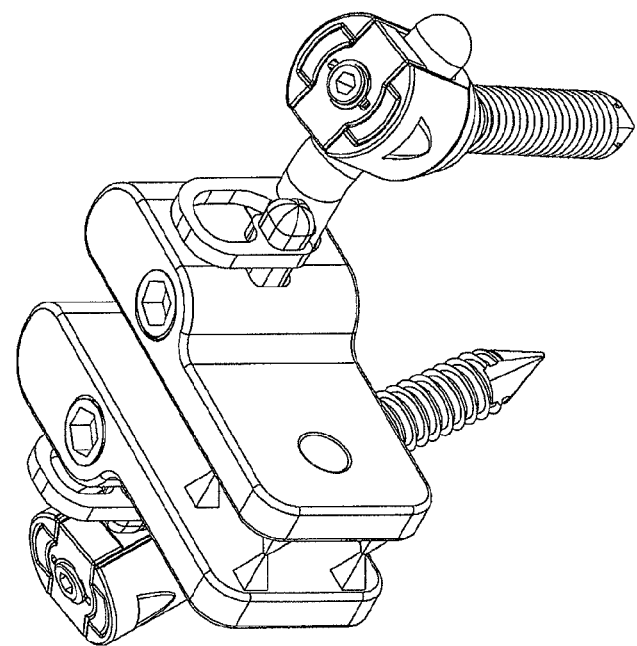
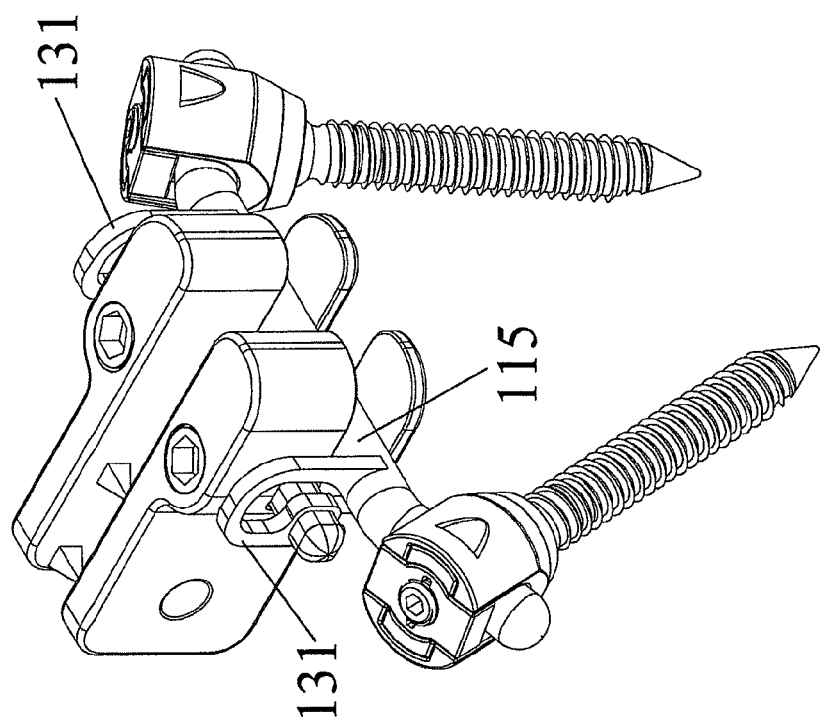
Fig. 49

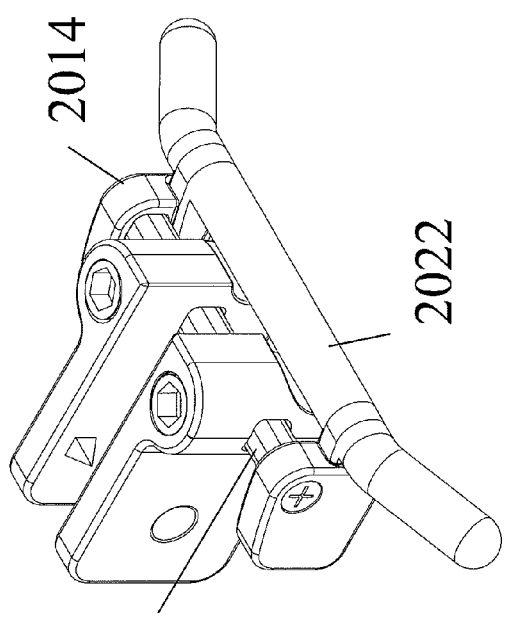
Fig. 54
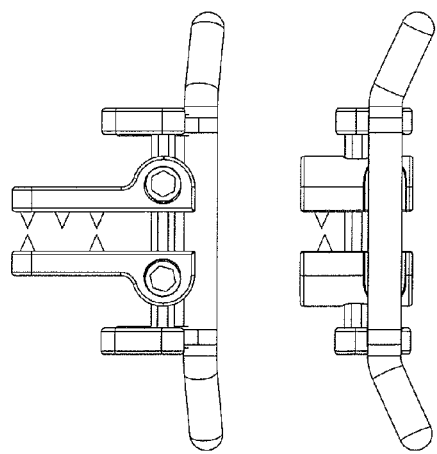
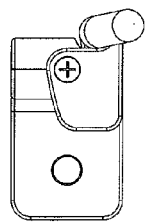
Fig. 55

SPINAL STABILIZATION SYSTEMS AND METHODS OF USE

REFERENCE TO PRIORITY DOCUMENTS

This application claims priority of co-pending U.S. Provisional Patent Application Ser. No. 60/903,486 filed Feb. 26, 2007, U.S. Provisional Patent Application Ser. No. 60/921,570 filed Apr. 3, 2007, and U.S. Provisional Patent Application Ser. No. 60/926,839 filed Apr. 30, 2007. Priority of the aforementioned filing dates is hereby claimed and the disclosures of the Provisional Patent Applications are hereby incorporated by reference in their entirety.

BACKGROUND

The present disclosure relates to devices and methods that permit fixation and stabilization of the bony elements of the skeleton. The devices permit adjustment and maintenance of the spatial relationship(s) between neighboring bones. Depending on the specifics of the embodiment design, the motion between adjacent skeletal segments may be maintained, limited or completely eliminated.

Spinal degeneration is an unavoidable consequence of aging and the disability produced by the aging spine has emerged as a major health problem in the industrialized world. Alterations in the anatomical alignment and physiologic motion that normally exists between adjacent spinal vertebrae can cause significant pain, deformity, weakness, and catastrophic neurological dysfunction.

Surgical decompression of the neural tissues and immobilization of the vertebral bones is a common option for the treatment of spinal disease. In addition to mechanical fixation, a bone graft or comparable bone-forming material is used to connect the vertebral bones and, with ossification of the graft material, the vertebral bodies are fused together by the bony bridge. Currently, mechanical fixation is most frequently accomplished by anchoring bone screws into the pedicle portion of each vertebral body and then connecting the various screw fasteners with an interconnecting rod. The screw/rod construct produces rigid fixation of the attached bones.

The growing experience with spinal fusion has shed light on the long-term consequences of vertebral immobilization. It is now accepted that fusion of a specific spinal level will increase the load on, and the rate of degeneration of, the spinal segments immediately above and below the fused level. As the number of spinal fusion operations have increased, so have the number of patients who require extension of their fusion to the adjacent, degenerating levels. The rigidity of the spinal fixation method has been shown to correlate with the rate of the degenerative progression of the adjacent segments. In specific, implantation of stiffer instrumentation, such as rod/screw implants, produced a more rapid progression of the degeneration disease at the adjacent segment than use of a less stiff fixation implant.

An additional shortcoming of the traditional rod/screw implant is the large surgical dissection required to provide adequate exposure for instrumentation placement. The size of the dissection site produces unintended damage to the muscle layers and otherwise healthy tissues that surround the diseased spine. A less invasive spinal fixation implant would advantageously minimize the damage produced by the surgical exposure of the spine.

Fixation of the spinous process segment of adjacent vertebrae provides a less rigid and less invasive method of vertebral fixation. Kapp et al. in U.S. Pat. No. 4,554,914 issued Nov. 26, 1985 disclosed a device of two elongated plates that are adapted to clamp onto adjacent spinous process. The plates are disadvantageously connected by locking bolts that transverse the substances of each spinous process. Bolts placed in this configuration will necessarily weaken the bony elements and lead to spinous process fractures and construct failure. Howland et al in U.S. Pat. No. 5,496,318, issued Mar. 5, 1996 disclosed the placement of an inter-spinous process spacer and encircling tension band to reduce vertebral motion. While the device can reduce vertebral flexion and extension, it can not effectively resist vertebral movement in the other motion planes. In U.S. Pat. No. 6,312,431 issued Nov. 6, 2001, Asfora disclosed a device comprised of two opposing plates that are interconnected by a malleable tether and adapted to capture the adjacent spinous processes between them. As with the Howland device, the fixation strength of this implant is limited by the mobile interconnecting tether. As such, neither implant can effectively immobilize the vertebral bones in all relevant motion planes. The lack of fixation significantly increases the possibility that the bone graft will not heal, the vertebral bones will not fuse, the construct will fail and the patient will develop chronic pain.

Superior immobilization devices were disclosed by Robinson et al. in U.S. Pat. No. 7,048,736 issued May 23, 2006 and by Chin et al. in U.S. Pub. Nos. 2007/0179500, 2007/0233082 and 2007/0270840. Each of these documents disclosed plates (or segments thereof) that engage each side of two adjacent spinous processes, wherein the plates are interconnected by a rigid member that resides within the interspinous space. Mechanical testing of the Robinson device was recently published by J C Wang et al. in the Journal of Neurosurgery Spine (February 2006; 4(2):160-4) and the text is hereby incorporated by reference in its entirety. The device was found to be weaker than conventional fixation techniques in all modes of vertebral movement and particularly lacking in fixation of rotational motion. Because of its limited stabilization properties, the device should be used in conjunction with additional implants. (See Wang J C et al. in the Journal of Neurosurgery Spine. February 2006; 4(2):132-6. The text is hereby incorporated by reference in its entirety.)

As an additional shortcoming, the Robinson device can not be used to fixate the L5 vertebral bone to the sacrum. The spinous process of the first sacral vertebra is simply too small to permit adequate bone purchase and fixation with either the Robinson or Chin device. Since the L5/S1 level is a frequent site of spinal disease, the inapplicability of these devices at this level is a significant limitation of these implants.

In U.S. Pub. Nos. 2006/0036246, Carl and Sachs disclose a fixation device adapted to fixate the spinous process of one vertebral level to bone screws anchored into the pedicle portion of an adjacent vertebral level. While this invention would permit application at the L5/S1 level and circumvent one disadvantage of the aforementioned spinous process fixation plates, it relies on direct screw fixation into the distal aspect of the spinous process. This technique disadvantageously replicates the inadequate fixation characteristics of the Kapp device previously discussed (U.S. Pat. No. 4,554,914) and carries a high likelihood of spinous process fracture and complete construct failure. Indeed, the inventors try to address this design flaw by augmenting the strength of the spinous process through the use of an internal bone filler or an external brace. Regardless of these efforts, however, the disclosed device provides a cumbersome implant that carries a high likelihood of spinous process fracture and complete loss of vertebral fixation.

SUMMARY

The preceding discussion illustrates a continued need in the art for the development of a spinous process device and method that would provide superior vertebral fixation than existing spinous process implants. The device should be amenable to placement through a minimally invasive surgical approach. When vertebral fusion is desired, the device desirably provides adequate fixation in all movement planes so that the probability of bone graft healing is maximized. The implant would desirably provide less rigid fixation than traditional rod/screw fixation.

In the treatment of spinal disease, it is sometimes desirable to limit vertebral motion in one or more axis while maintaining movement in other motion planes. Vertebral segments that are treated using these motion preservation techniques will not be fused and a bone graft spanning the space between the vertebral bones is not employed. When motion preservation is desired, the device provides adequate fixation onto each attached vertebral bone while controlling the motion between them. Moreover, a hybrid device would advantageously provide fusion at one or more vertebral levels and motion preservation at other vertebral levels.

This application discloses novel implants and methods of implantation that address current deficiencies in the art. In an embodiment, there is disclosed an orthopedic device adapted to fixate the spinous processes of one vertebral bone to bone fasteners anchored into the pedicle portion of an adjacent vertebral body. The implant may capture the spinous process by using an encircling contoured rod or hooks. Alternatively, the implant may contain at least one barbed bone engagement member located on each side of the spinous process and adapted to forcibly abut and fixate into the side of the spinous process. The device further contains a locking mechanism that is adapted to transition from a first unlocked state wherein the device components are freely movable relative to one another to a second locked state wherein the device is rigidly immobilized and affixed to the bone.

Alternative embodiments of the aforementioned device are disclosed. In one embodiment, the device is adapted to fixate at least three vertebral bones. In that embodiment, the device captures the spinous processes of one vertebral bone and fixates it onto an elongated rod that is adapted to engage bone fasteners anchored into the pedicle portion of at least two additional vertebral bodies. In another embodiment, the device is adapted to attach onto the rod portion of an existing screw/rod construct and functions to extend the level of vertebral fixation.

In other embodiments, there is disclosed a series of orthopedic devices that are adapted to fixate onto the spinous processes of one vertebral bone and onto bone fasteners anchored into the pedicle portion of an adjacent vertebral body. The device provides controlled movement between the two attached vertebral bones. Multiple iterations of this device are illustrated. In some embodiments, bone graft or bone graft substitute may be used to fixate and fuse the device onto each of the anchored vertebral bones while still permitting movement between them.

In an alternative embodiment, the device also contains an elongated rod that is adapted to engage bone fasteners anchored into the pedicle portion of at least two additional vertebral bodies. This design feature produces a hybrid device that provides controlled motion between at least a first pair of vertebral bones and rigid immobilization between at least a second pair of vertebral bones.

In an additional embodiment, a implant is used to fixate onto the spinous process of each of two adjacent vertebral bone. The implant contains at least one barbed bone engagement member located on each side of the spinous process and adapted to forcibly abut and fixate into the side of the spinous process at each level. The implant allows controlled movement between the two attached spinous processes. The implant may further contain a cavity adapted to accept a bone graft or bone graft substitute so that, with bone formation, the device members may fuse onto the spinous processes and provide superior device adhesion to the vertebral bone. In another embodiment, a bone containment device is disclosed that is adapted to span the distance between the lamina of neighboring vertebrae. The device contains an internal cavity adapted to accept a bone graft or a bone graft substitute so that, with bone formation, the lamina of neighboring vertebral bones are fused together.

In one aspect, there is disclosed an orthopedic device adapted to fixate at least two vertebral bones, comprising: at least one bone engagement member located on each side of a spinous process of a first vertebra wherein the bone engagement member are each forcibly compressed and affixed onto the sides of the spinous process; a connector member adapted to interconnect each bone engagement members on one side of a spinous processes of a first vertebra with at least one bone fastener affixed to a second vertebra; a cross member extending across the vertebral midline and adapted to adjustably couple the bone engagement member and connector member on one side of the vertebral midline with the bone engagement member and the connector member on the other side of the vertebral midline; and a connection between the bone engagement members the connection comprising a connector member, and a cross member wherein the connection is capable of reversibly transitioning between a first state where the orientation between the bone engagement member, the connector member and the cross member is changeable in at least one plane and a second state where the orientation between the bone engagement member, the connector member and the cross member is rigidly affixed.

In another aspect, there is disclosed an orthopedic device adapted to fixate at least two vertebral bones, comprising: at least one bone engagement member located on each side of a spinous process of a first vertebra wherein the bone engagement member is forcibly compressed and affixed onto the sides of the spinous process; a connector member adapted to inter-connect each bone engagement members on one side of a spinous processes of a first vertebra with at least one rod that is used to inter-connect at least two bone fastener affixed to additional vertebral bones; a cross member extending across the vertebral midline and adapted to adjustably couple the bone engagement member and connector member on one side of the vertebral midline with the bone engagement member and connector member on the other side of the vertebral midline; and a connection between a bone engagement members, the connection comprising a connector member and a cross member wherein the connection is capable of reversibly transitioning between a first state where the orientation between the engagement member, the connector member and the cross member is changeable in at least one plane and a second state where the orientation between the engagement member, the connector member and the cross member is rigidly affixed.

In another aspect, there is disclosed an orthopedic device adapted to fixate at least two vertebral bones, comprising: at least one contoured rod that contacts at least one surface of the spinous process of a first vertebra; a connector member adapted to interconnect one end of the contoured rod that is located on one side of a spinous processes of a first vertebra with a bone fastener affixed to a second vertebra; and a device body member extending across the vertebral midline and adapted to adjustably couple at least one end of the contoured rod with the connector members wherein the device body member further contains at least one locking mechanism that is capable of reversibly transitioning between a first state wherein the orientation between the contoured rod and at least one connector member is changeable in at least one plane and a second state wherein the orientation between the contoured rod and at least one connector member is rigidly affixed.

In another aspect, there is disclosed an orthopedic device adapted to fixate at least two vertebral bones, comprising: at least one hook member that contacts at least one surface of the posterior aspect of a first vertebra; and a connector member adapted to interconnect one end of the hook member attached to the posterior aspect of a first vertebra with a bone fastener affixed to a second vertebra; a device body member extending across the vertebral midline and adapted to adjustably couple at least one hook member attached to the posterior aspect of a first vertebra the connector members wherein the device body member further contains at least one locking mechanism that is capable of reversibly transitioning between a first state wherein the orientation between the hook member and at least one connector member is changeable in at least one plane and a second state wherein the orientation between the hook member and at least one connector member is rigidly affixed.

In another aspect, there is disclosed an orthopedic device adapted to control motion between at least two vertebral bones, comprising: at least one bone engagement member located on each side of a spinous process of a first vertebra wherein the bone engagement member is forcibly compressed and affixed onto the sides of the spinous process; a connector member adapted to interconnect each bone engagement members on one side of a spinous processes of a first vertebra with at least one bone fastener affixed to a second vertebra, wherein the engagement member contains a channel adapted to accept an end of the connector member and wherein the motion permitted by the interaction of each of the two channel and connector member surfaces determines the motion profile permitted by the device; a cross member extending across the vertebral midline and adapted to adjustably couple bone engagement member and connector member on one side of the vertebral midline with the bone engagement member and connector member on the other side of the vertebral midline; and a connection between the bone engagement members and cross member wherein the connection is capable of reversibly transitioning between a first state where the orientation between the engagement member and the cross member is changeable in at least one plane and a second state where the orientation between the engagement members and the cross member is rigidly affixed.

Other features and advantages will be apparent from the following description of various embodiments, which illustrate, by way of example, the principles of the disclosed devices and methods.

BRIEF DESCRIPTION OF THE DRAWINGS

FIG. 2 illustrates multiple views of the implant.

FIGS. 6 and 7 illustrate multiple views of a second device embodiment.

FIG. 12 shows the device of FIG. 11 in multiple orthogonal planes.

FIG. 24 shows the device of FIG. 23 in multiple orthogonal planes.

FIG. 26A shows another embodiment of the device of FIG. 11 wherein the rods are replaced with paddle attachment members.

FIG. 26B shows an exemplary embodiment of a paddle attachment member.

FIG. 37A shows a cross-sectional view through the articulation mechanism.

FIG. 37B shows a cross-sectional view through the locking mechanism.

FIG. 39 shows the device of FIG. 38 in multiple orthogonal planes.

FIGS. 41, 42 and 43 illustrate cross-sectional views at different points within the device.

FIG. 46 shows the device of FIG. 45 in multiple orthogonal planes.

FIG. 49 illustrates a perspective view of an alternative embodiment.

FIG. 54 illustrates another device embodiment.

FIG. 55 shows the device of FIG. 54 in multiple orthogonal planes.

DETAILED DESCRIPTION

Figure 1:
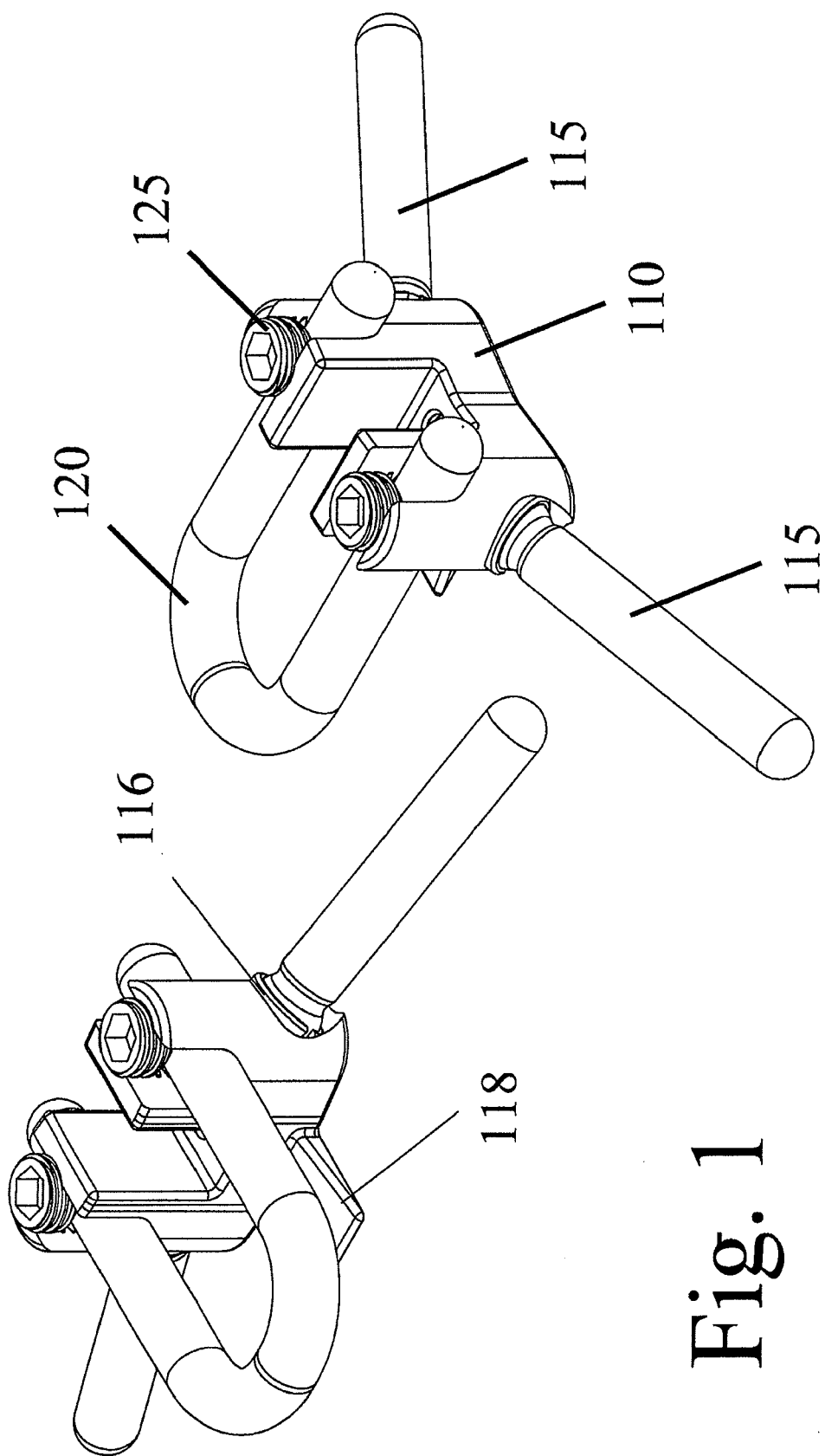
FIG. 1 shows perspective views of an orthopedic implant adapted to fixate the spinous process of a first vertebral bone to screw fasteners affixed to the pedicle portion of a second vertebral bone.
Figure 3:
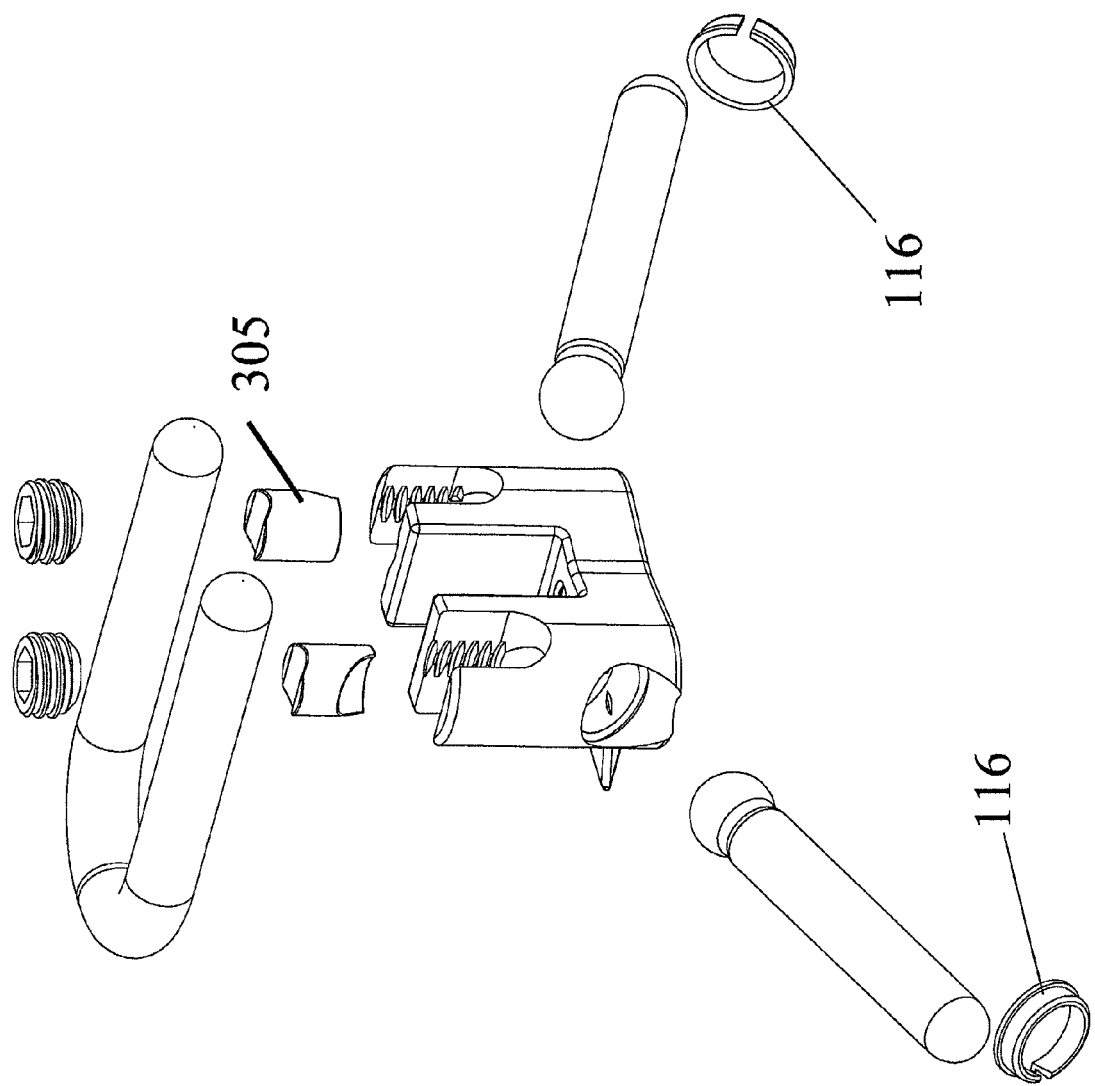
FIG. 3 shows an exploded view of the implant.

FIGS. 1-3 show various views of an orthopedic device adapted to fixate the spinous process of a first vertebral bone to screw fasteners affixed to the pedicle portion of a second vertebral bone. The device includes a central member 110 having a pair of movably attached rods 115 extending outwardly therefrom. A central threaded bore 112 is contained in member 110 and serves as an attachment point for the device placement instruments. Each of the rods 115 has a ball-shaped head that is positioned inside a complimentary shaped seat inside the central member 110. The spherical head is positioned into the seat inside member 110 and retained in place by collapsible "C" ring 116. In the unlocked state, the spherical head of rod 115 is freely movable within the seat of member 110.

A U-shaped rod 120 is also attached to the central member 110. The rod 120 can be fixated to the central member 110 by tightening a pair of lock nuts 125 downwardly onto ends of the rod 120. As shown in FIG. 2, the lock nuts 125 are positioned atop the heads of the rods 115. This permits the lock nuts 125 to provide a downward force onto both the U-shaped rod 120 and the heads of the rods 115. In this manner, the lock nuts 125 serve as a locking member that simultaneously locks the U-shaped rod 120 and the rods 115 to the central member 110. The U-shaped rod 120 is adapted to fit around a spinous process of a vertebral bone. The rod 120 can have various shapes and configurations beside a U-shape that permits the rod to be fit around a spinous process.

Figure 4:
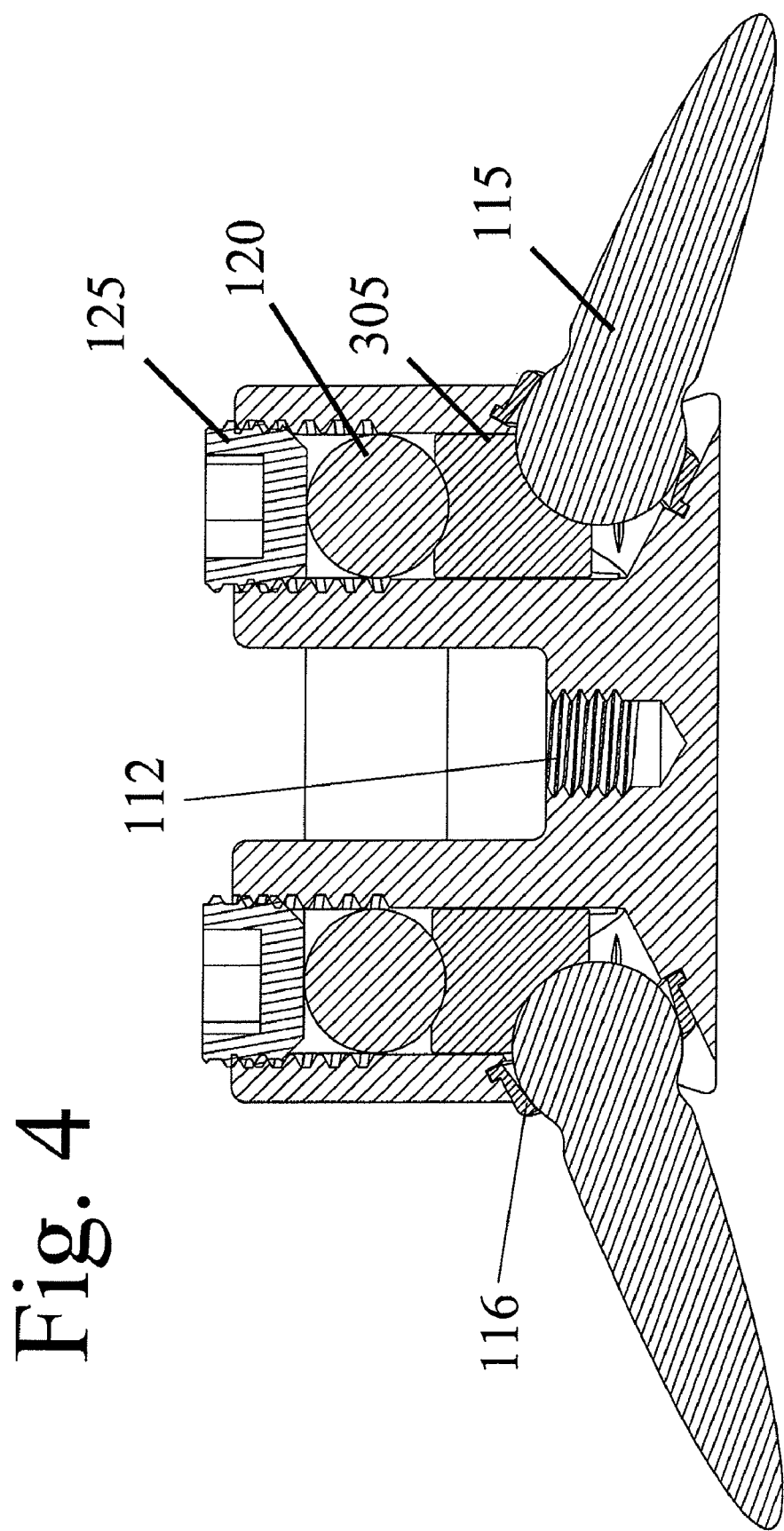
FIG. 4 shows a section view through the locking mechanism of the implant.

FIG. 3 shows an exploded view of the device and FIG. 4 shows a cross-sectional view of the device through the locking mechanism. A locking plug 305 is interposed between each of rods 120 and the spherical heads of rods 115. As the locking nuts 125 are tightened downward onto the rod 120, the locking plugs 305 are advanced onto the spherical heads of rods 115, locking and immobilizing the rods 115 relative to the central member 110.

Figure 5:
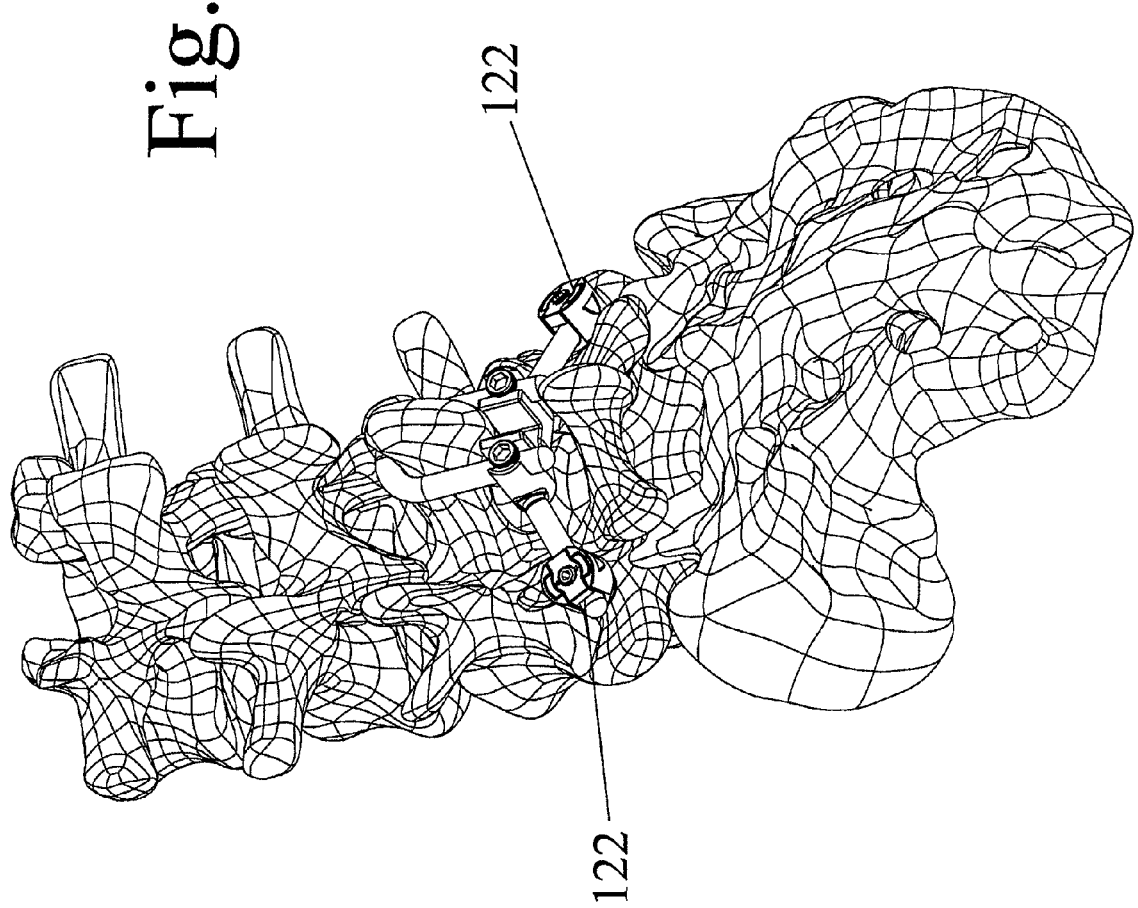
FIG. 5 shows a perspective view of the implant attached onto a segment of the spine.

FIG. 5 shows a perspective view of the device attached onto a segment of the spine. The vertebrae are represented schematically and those skilled in the art will appreciate that actual vertebral bones may include anatomical details that differ from those shown in FIG. 5. The U-shaped rod 120 is shaped such that it can wrap around or otherwise secure onto the spinous process of a vertebral body. The central member 110 is also positioned to contact the spinous process. The foot plate 118 of member 110 is preferably positioned beneath the lamina of the upper vertebral bone. The U-shaped rod 120 can be adjusted relative to the central member 110 prior to the actuation of the lock nuts. The rod 120 can adjustably slide relative to the central member 110 to accommodate spinous processes of various sizes. Preferably, the rod 120 is positioned around the spinous process in a manner that tightly captures the top surface of the spinous process against the central rod bend and the bottom surface of the spinous process or lamina against member 110. After appropriate positioning of rod 120, the free end of each rod 115 is rotated and placed into the rod-receiving seat of the previously placed bone fasteners 122. The fastener lock nuts are tightened and the ends of rods 115 are immobilized relative to the fasteners. Subsequently, tightening of lock nuts 125 immobilizes rod 122, rods 115 and central member 110 relative to one another and produce a rigid implant. As illustrated, the device fixates the spinous processes of a first vertebral bone to bone fasteners anchored into the pedicle portion of a second vertebral bone.

Figure 6:
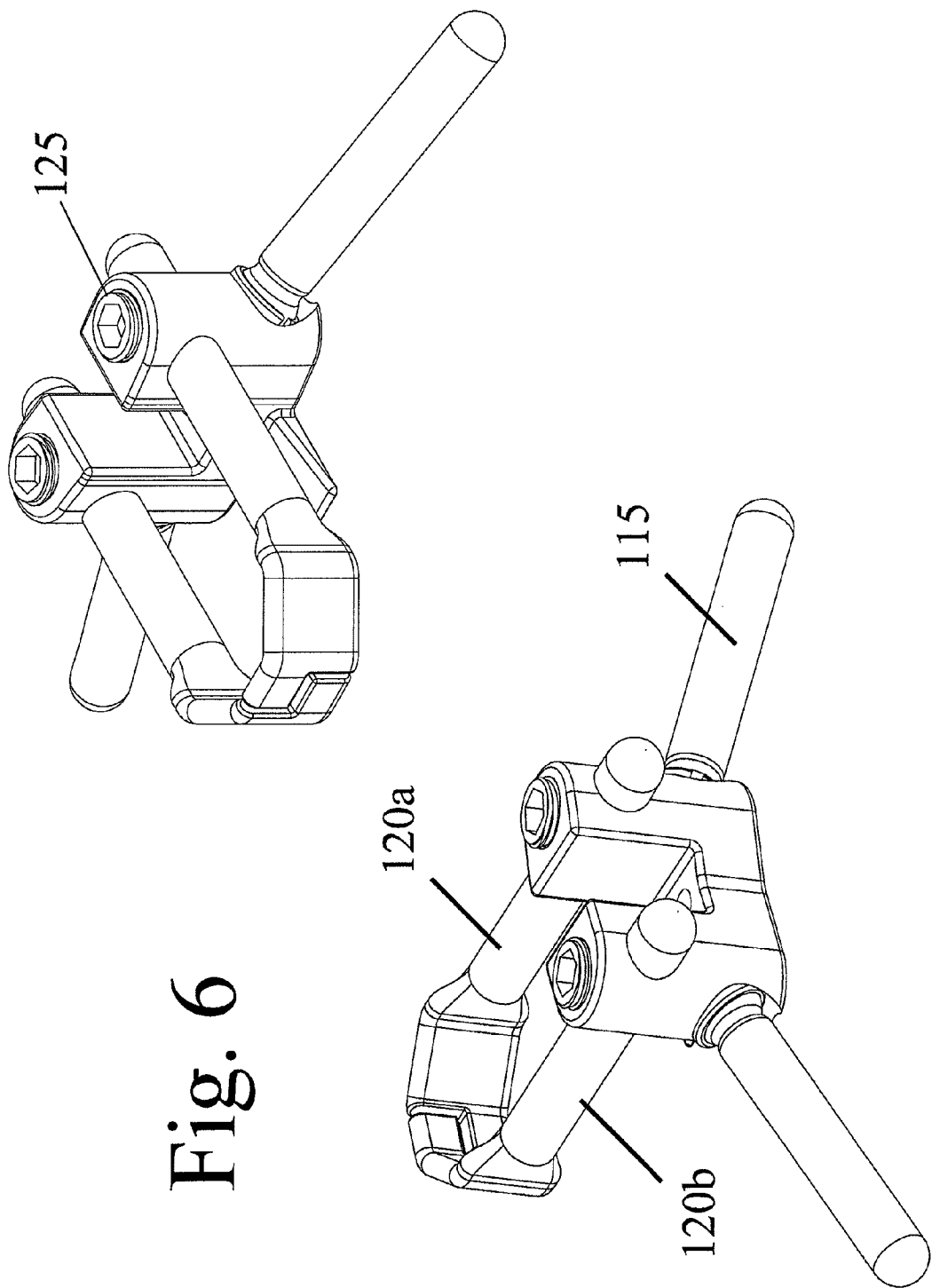
Figure 8:
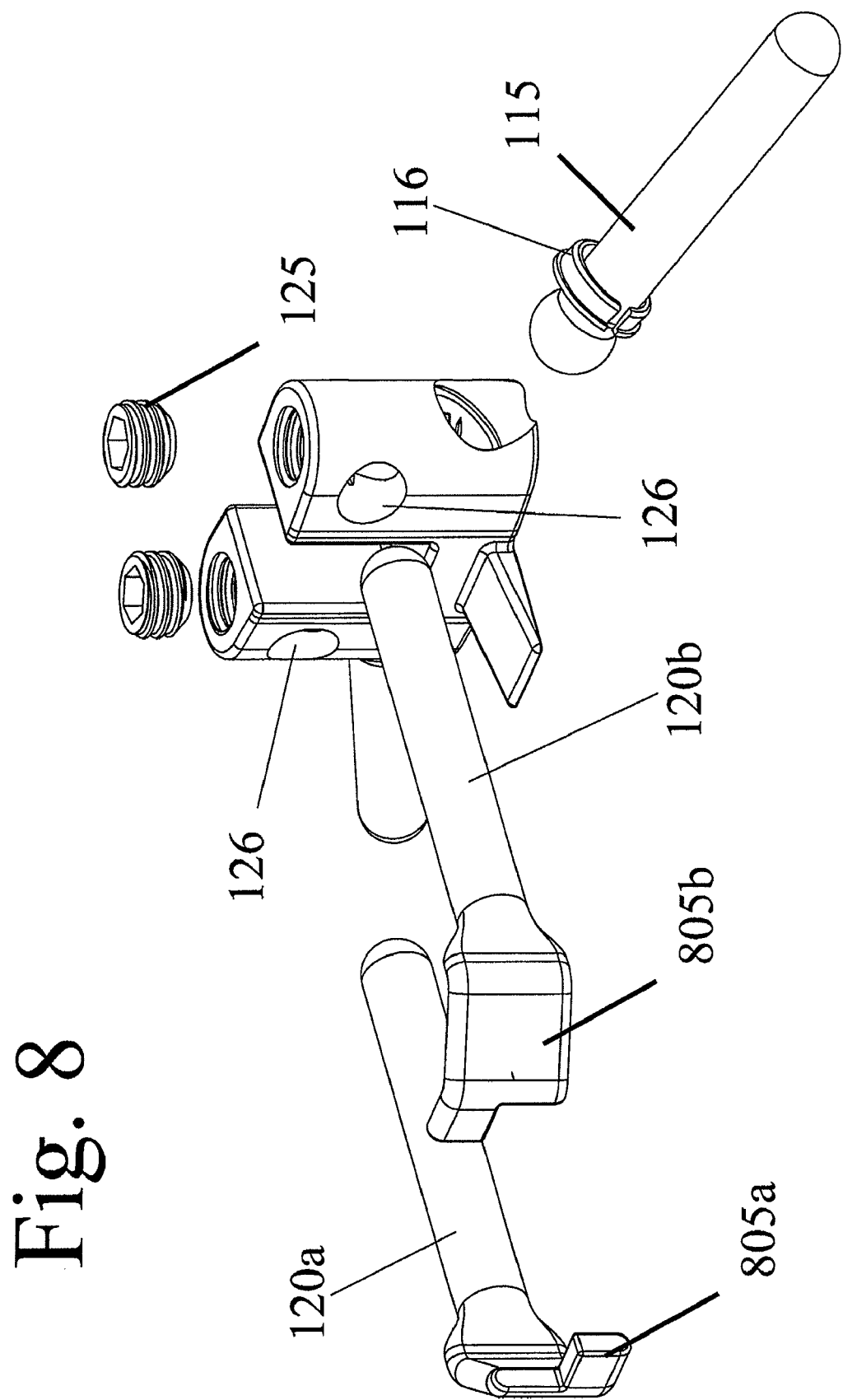
FIG. 8 shows a partly exploded view of the second device embodiment.

FIGS. 6 and 7 show another device embodiment. An exploded view is shown in FIG. 8. While similar to the previous embodiment, the current device uses rods 120 with terminal hooks 805 to attach onto the upper aspect of the spinous process or upper edge of the lamina of the upper vertebral bone. As shown in the exploded view of FIG. 8, the end 805 of each rod 120 is configured as a hook wherein the two hooks 805a and 805b can interfit with one another. The cylindrical end of each rod 120 is adapted to fit within complimentary bores 126 of member 110.

As in the previous embodiment, central member 110 has a cavity adapted to accept the spherical head of each rod member 115. "C" ring 116 retains the spherical heads attached to member 110 after device assembly. The locking mechanism of the device is similar to that of the previous embodiment. Advancement of lock nuts 125 immobilizes rods 120, rods 115 and central member 110 relative to one another. The placement protocol is similar to that of the previous embodiment. However, as noted, hook member 805 may be alternatively attached onto the superior edge of the lamina of the upper vertebral bone.

Figure 9:
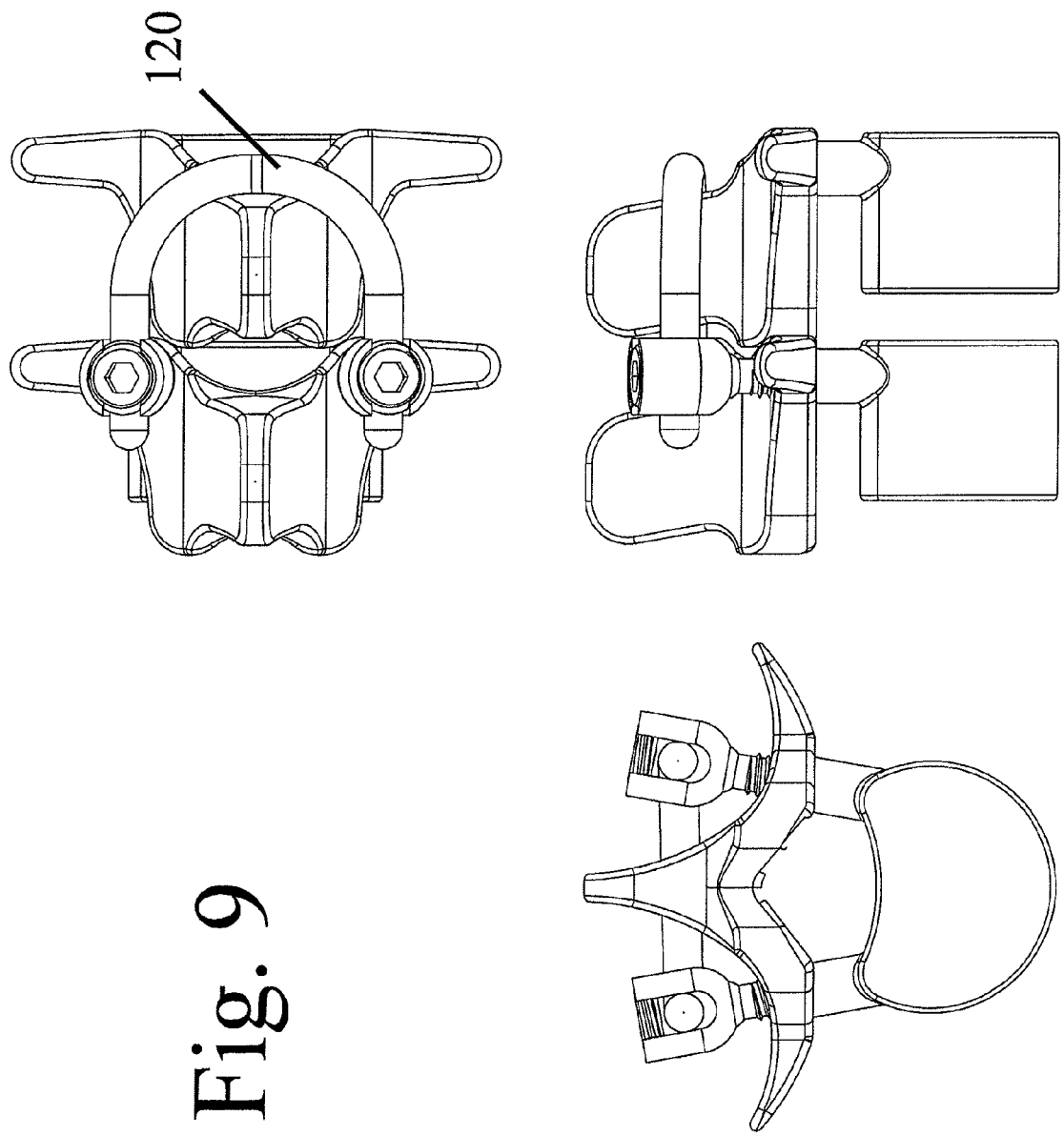
FIGS. 9 and 10 illustrate multiple views of another device embodiment.
Figure 10:
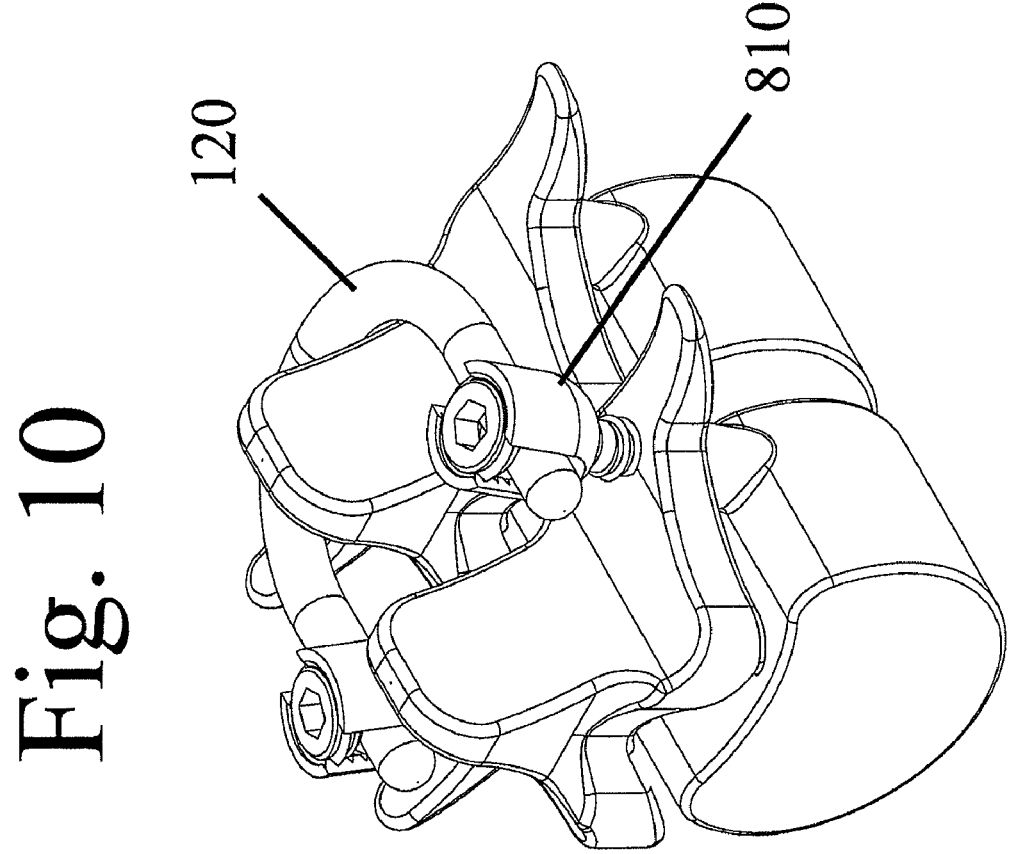

FIGS. 9 and 10 illustrate multiple views of another device embodiment that fixates the spinous processes of one vertebral bone to bone fasteners anchored into the pedicle portion of an adjacent vertebral body. The vertebrae are represented schematically and those skilled in the art will appreciate that actual vertebral bones may include anatomical details that differ from those shown in these figures. In this embodiment, a U-shaped rod 120 is sized and shaped to wrap around the spinous process of a first vertebral body. Opposed ends of the rod 120 are coupled to bone fasteners such as bone screw assemblies 810. The bone fasteners are attached to the pedicles of an adjacent vertebral body. Unlike the previous embodiments, this device does not include a central member.

Figure 11:
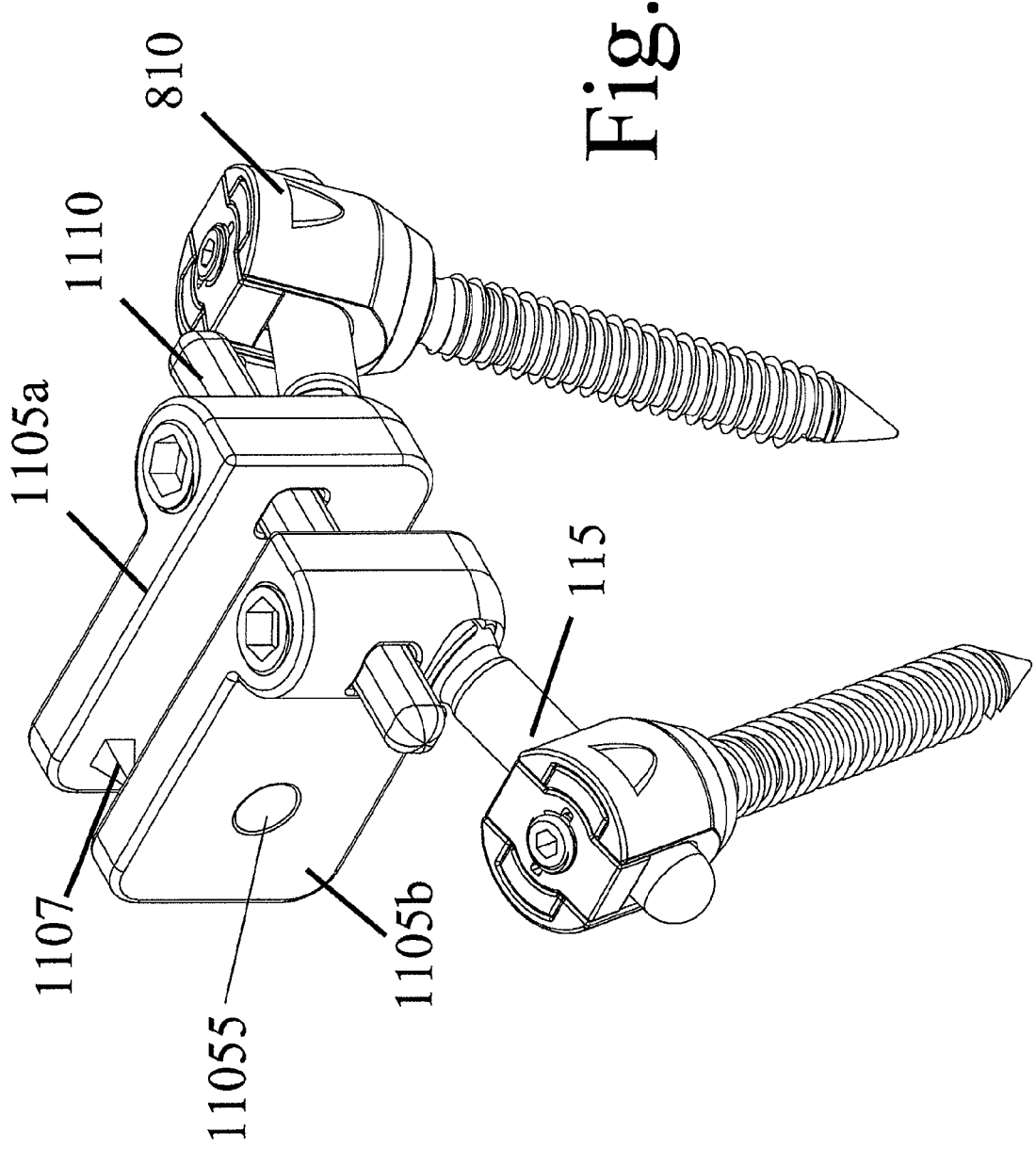
FIG. 11 illustrates a perspective view of a preferred embodiment of the current invention.
Figure 13:
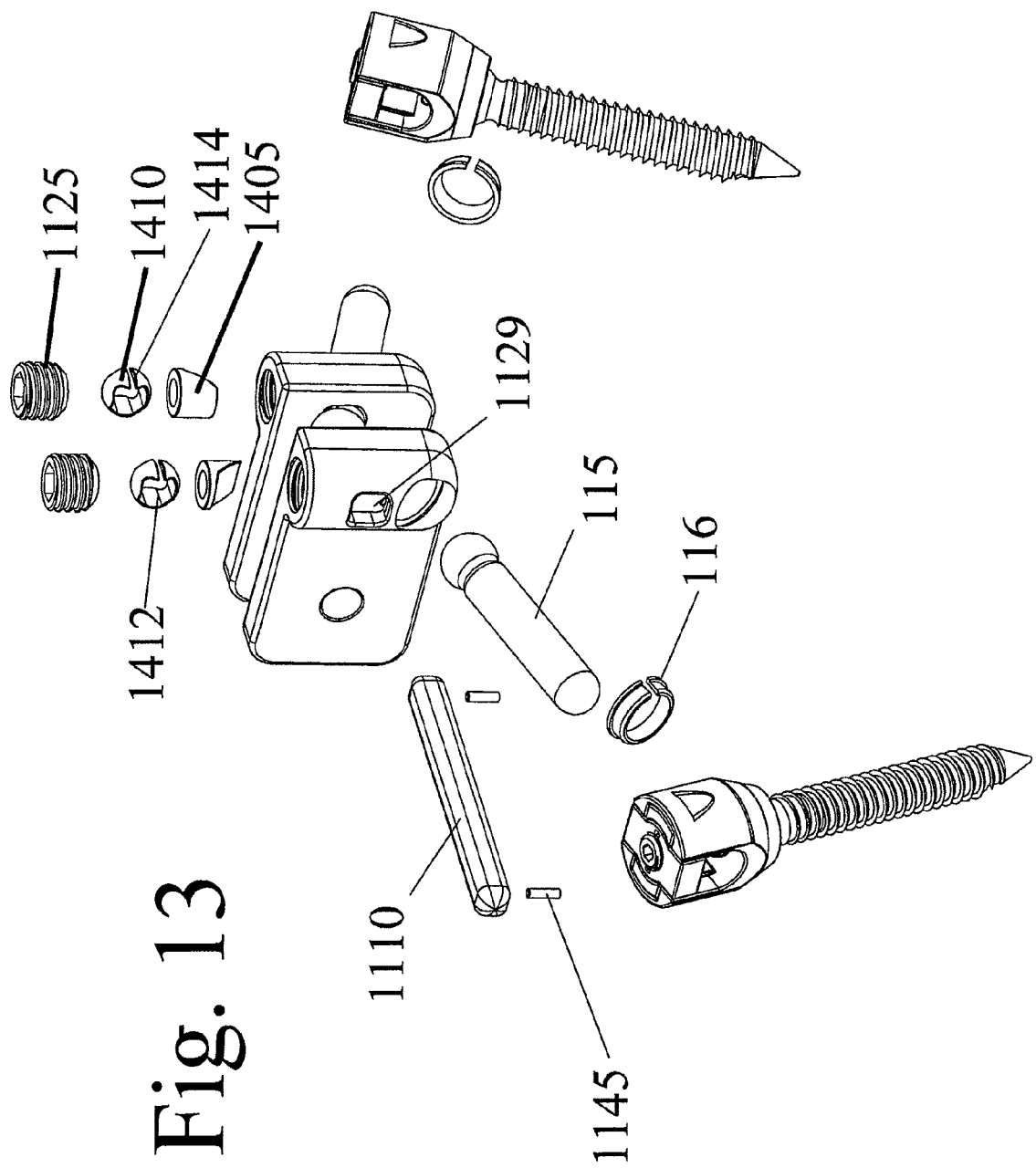
FIG. 13 shows an exploded view of the implant.

FIGS. 11-13 show another embodiment of a device that fixates the spinous processes of one vertebral body to bone fasteners anchored into the pedicle portion of an adjacent vertebral body. The device includes a pair of central members 1105a and 1105b (collectively central members 1105) with opposed interior surfaces. Fixation members such as barbs 1107 are positioned on the interior surfaces such that the barbs face inward for attaching to a spinous process positioned between the central members 1105. The central members 1105 are slidably mounted on a rod 1110 such that the central members 1105 can move toward and away from one another. In this manner, the size of the space between the central members 1105 can be adjusted to accommodate spinous processes of various sizes. Further, the orientation of members 1105 relative rod 1110 is adjustable in multiple planes.

Each rod 115 is coupled to a central member 1105 such that it extends outwardly therefrom. Rod 115 has a spherical head that is positioned inside a complimentary shaped seat inside a respective central member 1105 and retained in position collapsible "C" ring 116. In the unlocked state, the spherical head of rod 115 is freely movable within member 1105 in a ball and socket manner. The end of each rod 115 can be attached to a bone fastener, such as pedicle screw assemblies 810, that is anchored to the pedicle portion of a vertebral bone.

Figure 14:
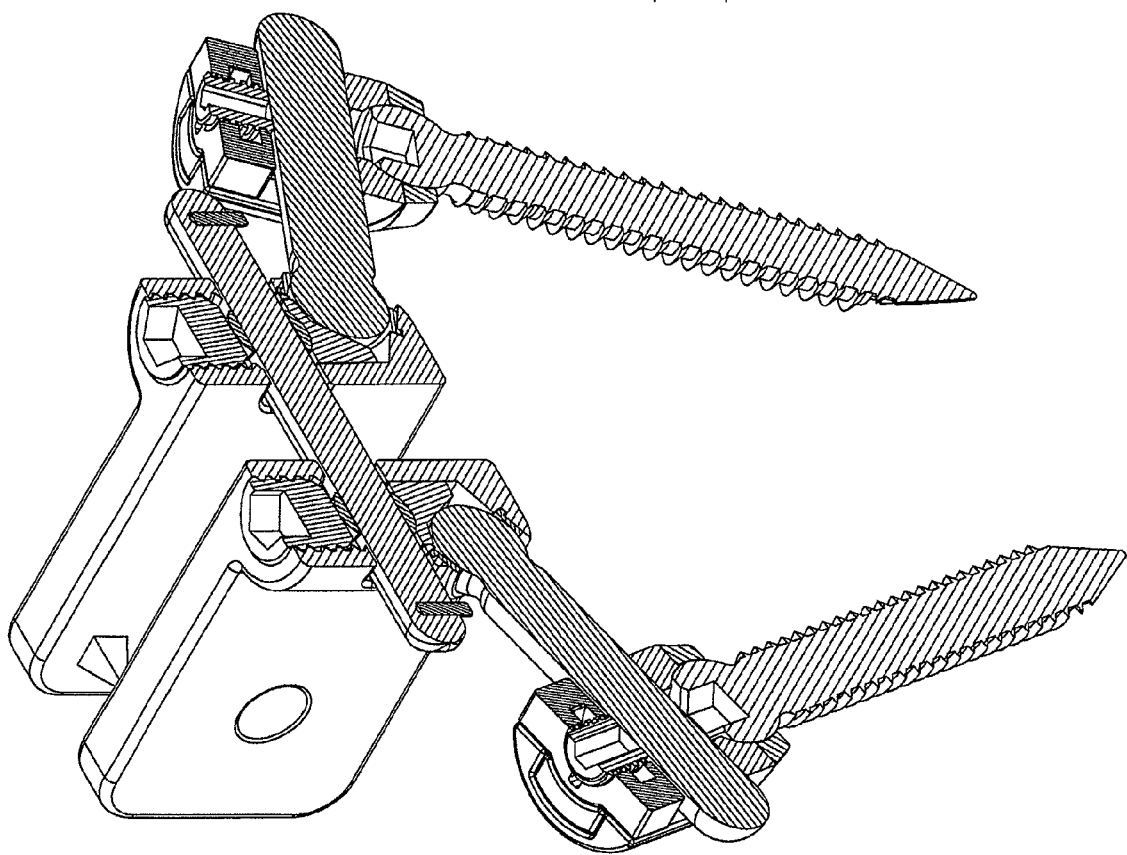
FIGS. 14 and 15 illustrate cross-sectional views of the locking mechanism of the implant.
Figure 15:
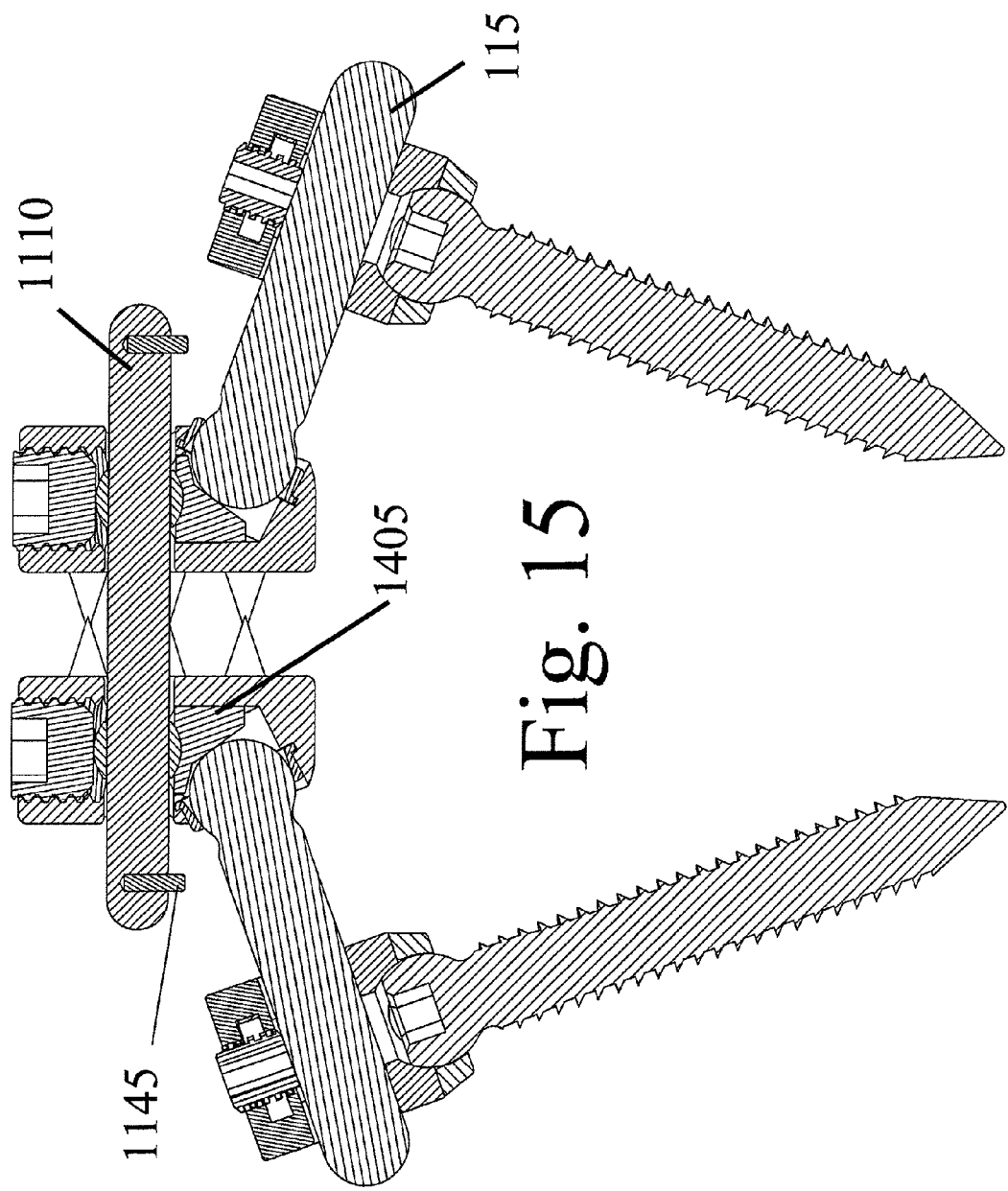

The top surface of each member 1105 contains a bore 1127, which extends from the top surface to the cavity adapted to receive the spherical head of rod 115. The upper aspect of bore 1127 is threaded. Bore 1127 is crossed by bore 1129, wherein the latter bore extends from the lateral to the medial wall of member 1105. A cross sectional view through the locking mechanism is shown in FIGS. 14 and 15. Spherical member 1410 has central bore 1412 and full thickness side cut 1414, thereby forming a compressible "C" ring that can be compressed onto the contents of bore 1412. In the assembled device, rod 1110 is positioned within central bore 1412 and can translate relative to it. With the application of a compressive load onto the outer surface of member 1410 by threaded locking nut 1125, member 1410 is compressed onto rod 1110 and the latter is immobilized within bore 1412. Retention pins 1145 are used to retain rod 1110 within member 1410 in the assembled device.

Advancement of each of lock nuts 1125 immobilizes rod 1110, rod 115 and central member 1105 relative to one another and renders the device rigid. With reference to the cross-sectional views of FIGS. 14 and 15, tightening lock nut 1125 downwardly onto spherical member 1410 produces a compressive load onto rod 1110 and a downward force onto locking plug 1405. The latter is pushed towards the spherical head of rod 115, thereby immobilizing rod 115 within central members 1105. In this manner, advancement of each lock nut 125 provides a downward force onto both rod 1110 and the spherical head of rod 115 contained with each member 1105. Thus, each lock nut 125 serves as a locking member that simultaneously locks rod 1110 and rod 115 to the central member 1105.

Figure 16:
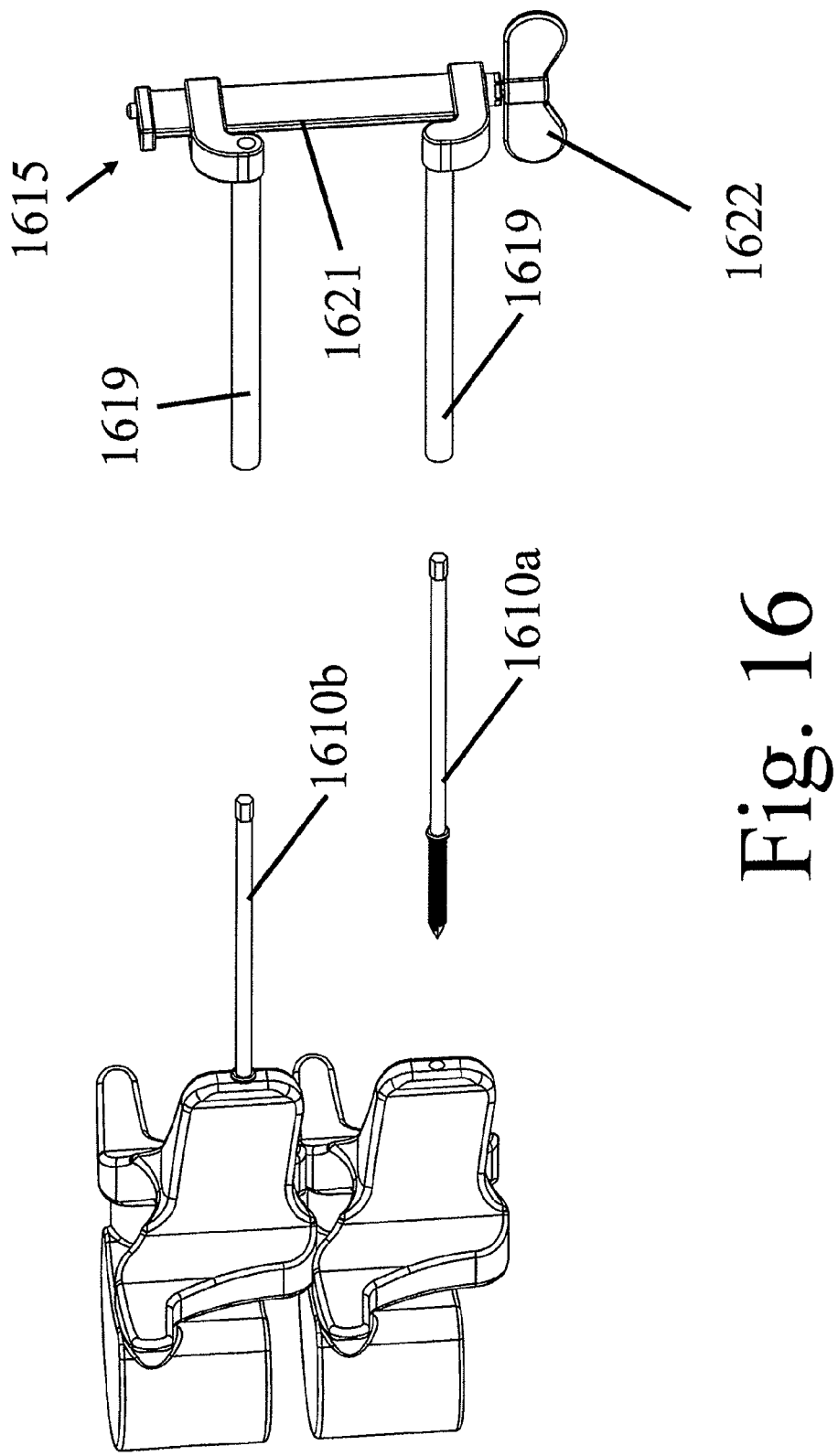
FIGS. 16 through 18 illustrate devices and methods for vertebral distraction in preparation for device placement.

The spinal level to be implanted has an upper and a lower vertebral bone and the device is attached onto the posterior aspect of these vertebral bones. Prior to device placement, the upper and lower vertebral bones are distracted to facilitate decompression of the nerve elements. FIG. 16 shows a perspective, assembled view of a distractor device. For clarity of illustration, the vertebral bodies are represented schematically and those skilled in the art will appreciate that actual vertebral bodies include anatomical details not shown in FIG. 16. The device generally includes a pair of anchors that include elongate distraction screws 1610 coupled to a platform 1615. Each of the distraction screws 1610 is advanced into the posterior surface of a spinous process and follows a posterior to anterior trajectory along the long axis of the spinous process. The distal end of each screw includes a structure for attaching to the spinous process, such as a threaded shank. The proximal ends of the distraction screws 1610 are attached to the platform 1615. The screws 1610 are axially positioned within sheaths 1619 that surround the screws and extend downwardly from the platform 1615.

Figure 17:
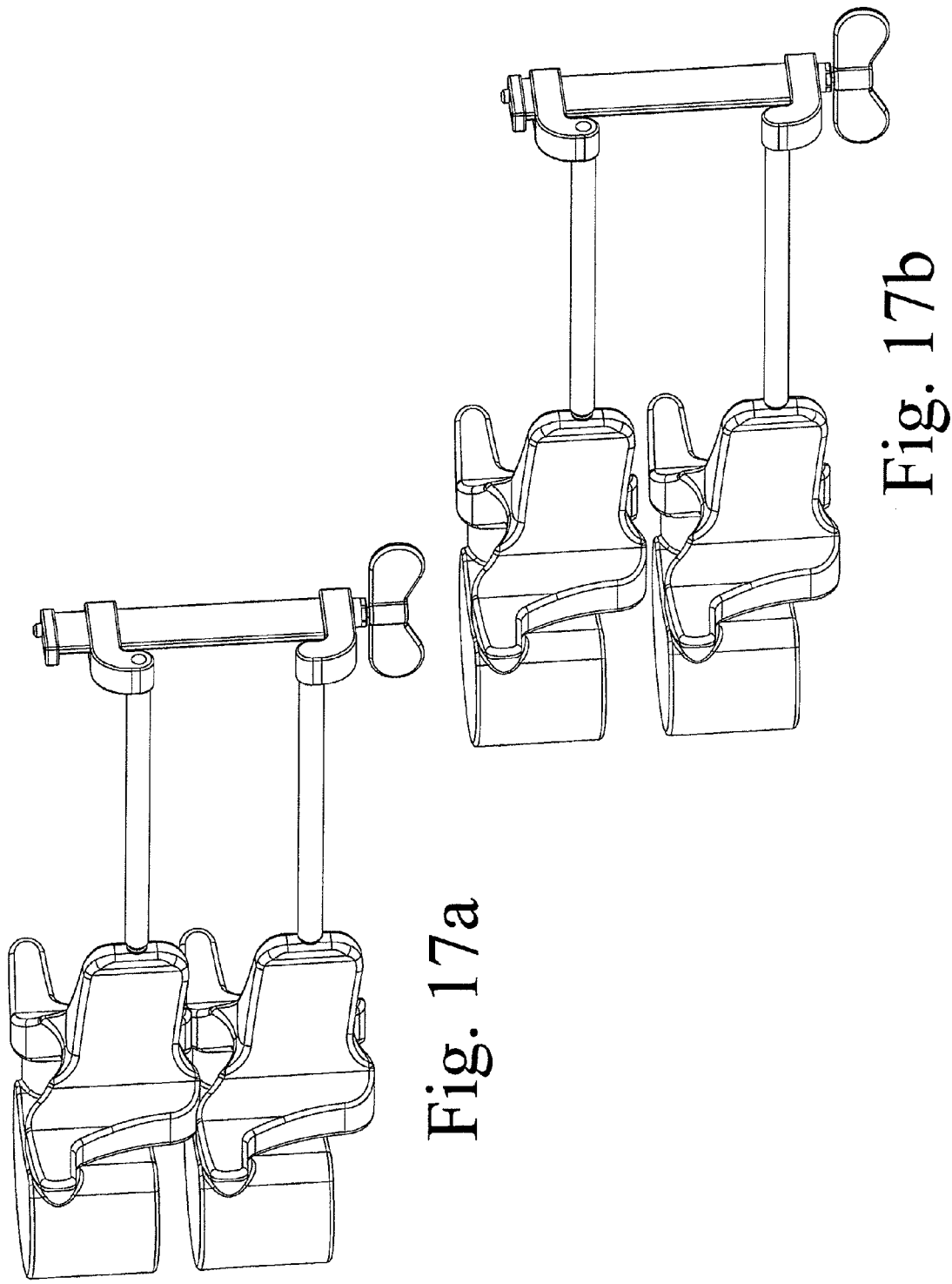
Figure 18:
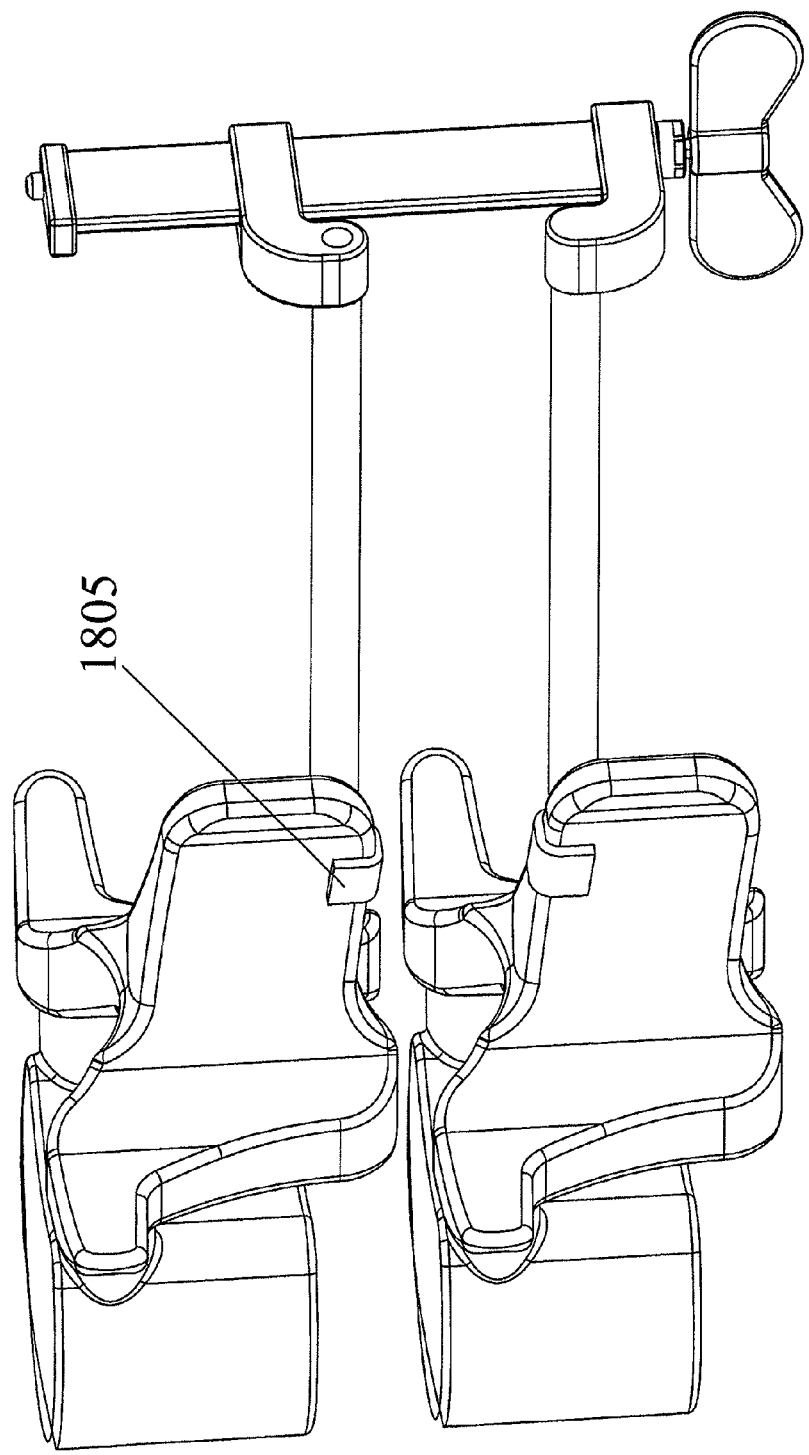
Figure 19:
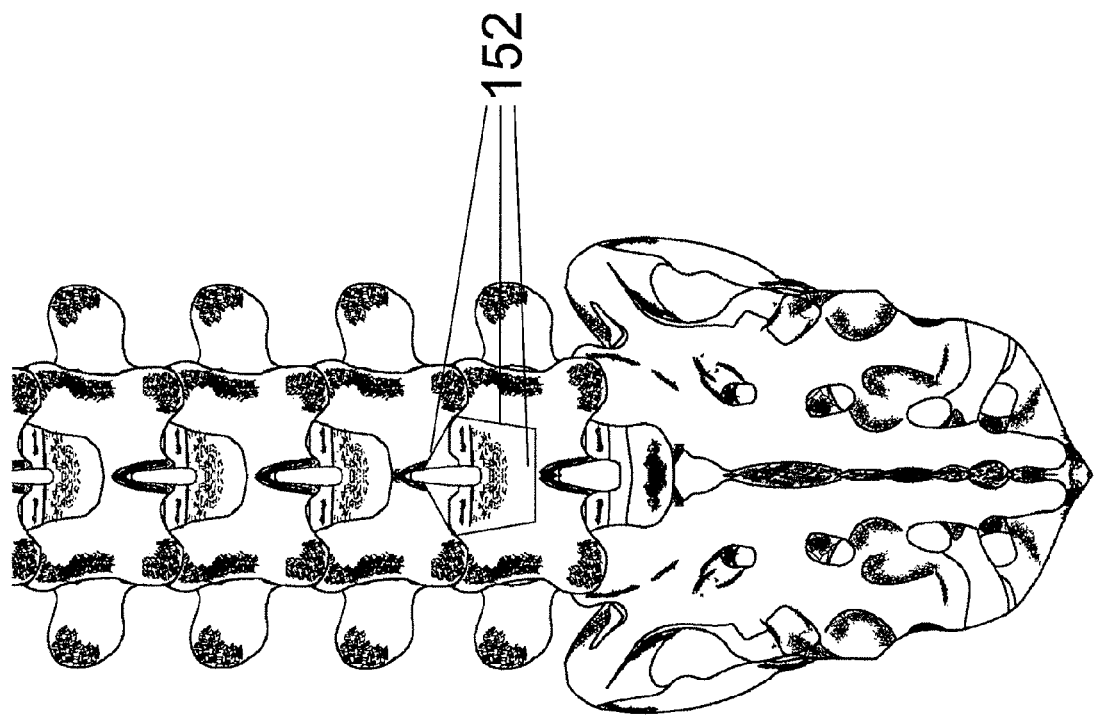
FIG. 19 shows a method of vertebral and nerve decompression.

The distraction actuator 1622 is actuated to cause one of the distraction screws to slide along the rail 1621 such that it moves away form the other distraction screw. This applies a distraction force to the vertebral bodies to distract the vertebral bodies—as shown in FIG. 17. (In another embodiment, shown in FIG. 18, the distraction screws are replaced by clip members 1805 that couple to the spinous processes or lamina of the vertebral bodies. Other known methods of vertebral distraction may be alternatively used.) The decompression of the nerve elements is performed under distraction and it is schematically illustrated in FIG. 19. The bony and ligament structures that are compressing the nerves are removed from the lower aspect of the lamina of the upper vertebra and the upper aspect of the lamina of the lower vertebra (regions 1152).

Prior to device implantation, bone fasteners 810 had been placed into the pedicel portion of the lower vertebra on each side of the midline. A bone graft or bone graft substitute is packed with the facet joints and used to span the distance between the lamina of each of the upper and lower vertebra. The implant is positioned at the level of implantation such that opposing central members 1105 are disposed on either side of a spinous process of a the upper vertebral body. A compression device (not shown) attaches onto the lateral wall of each opposing central member 1105 at indentation 11055. The compression device forcefully abuts the medial aspect of each central member 1105 against a lateral wall of the spinous process and drives spikes 1107 into the bone. Spikes 1107 provide points of device fixation onto the each side of the spinous processes.

With the compression device still providing a compressive force, the distal ends of rods 115 are positioned into the rod receiving portions of bone fasteners 810. The locking nuts of the fasteners are actuated so that each rod 115 is locked within the respective fastener. Lock nuts 1125 are actuated, locking the device's locking mechanism and immobilize opposing central members 1105, the interconnecting rod 1110 and rods 115 relative to one another. The compression device is removed, leaving the device rigidly attached to the upper and lower vertebral bones.

Figure 20C:
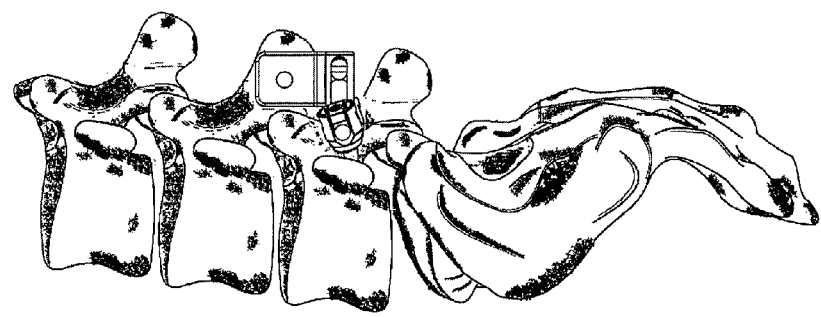
FIGS. 20a-20c show the device of FIG. 11 attached to the spine.
Figure 20B:
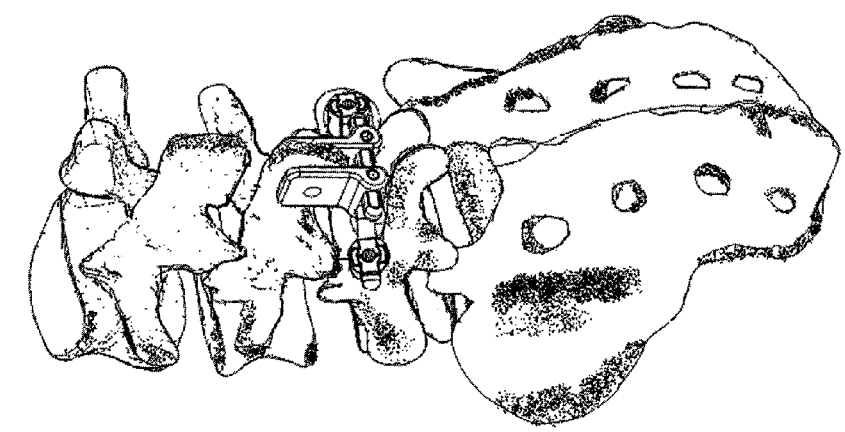
Figure 20A:
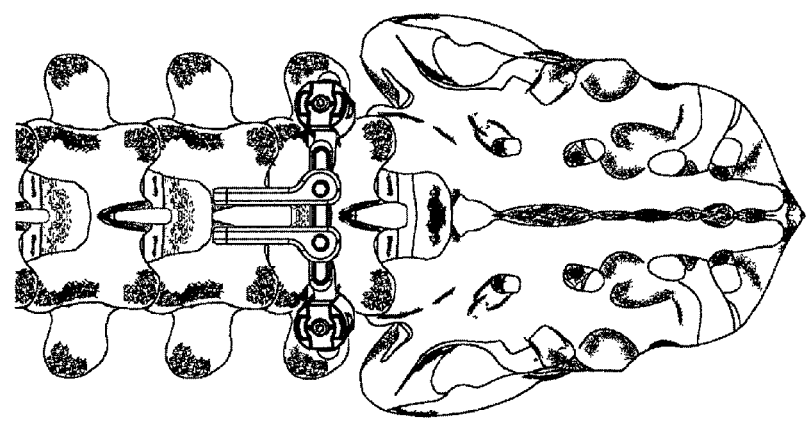
Figure 21:
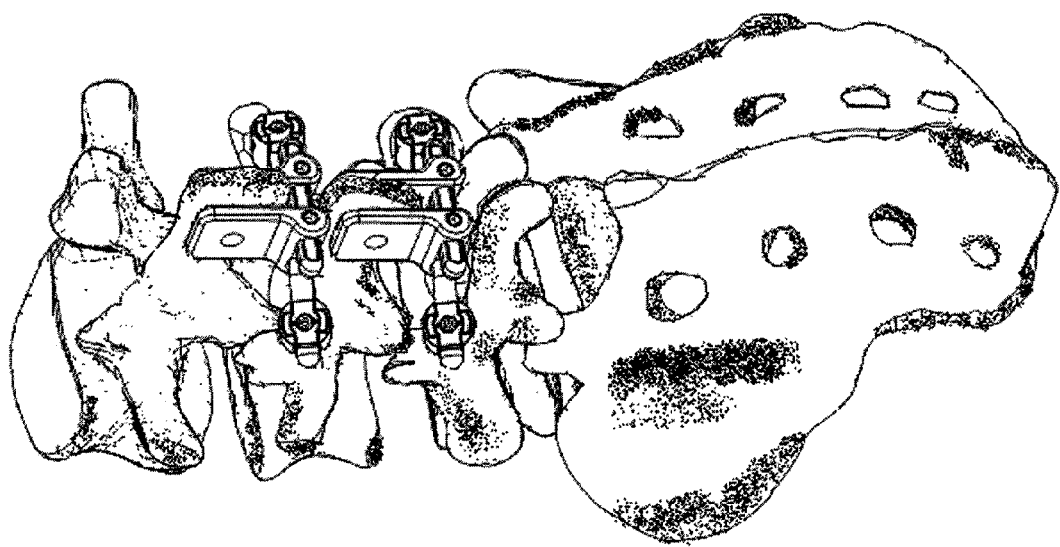
FIG. 21 illustrates the addition of a second device at an adjacent spinal level.

FIGS. 20a-20c show the device of FIG. 11 attached to the spine. As mentioned, the central members 1105 are spaced apart with a spinous process of an upper vertebra positioned in the space between them. The rods 115 are oriented so that they extend toward respective bone fasteners that are anchored to the pedicle portion of a lower vertebra. In this manner, the device fixates the spinous processes of one vertebral body to bone fasteners anchored into the pedicle portion of an adjacent vertebral body. FIG. 21 illustrates the addition of a second device at an adjacent spinal level. Note that device can be used to fixate the L5 vertebra to the sacrum.

Figure 22:
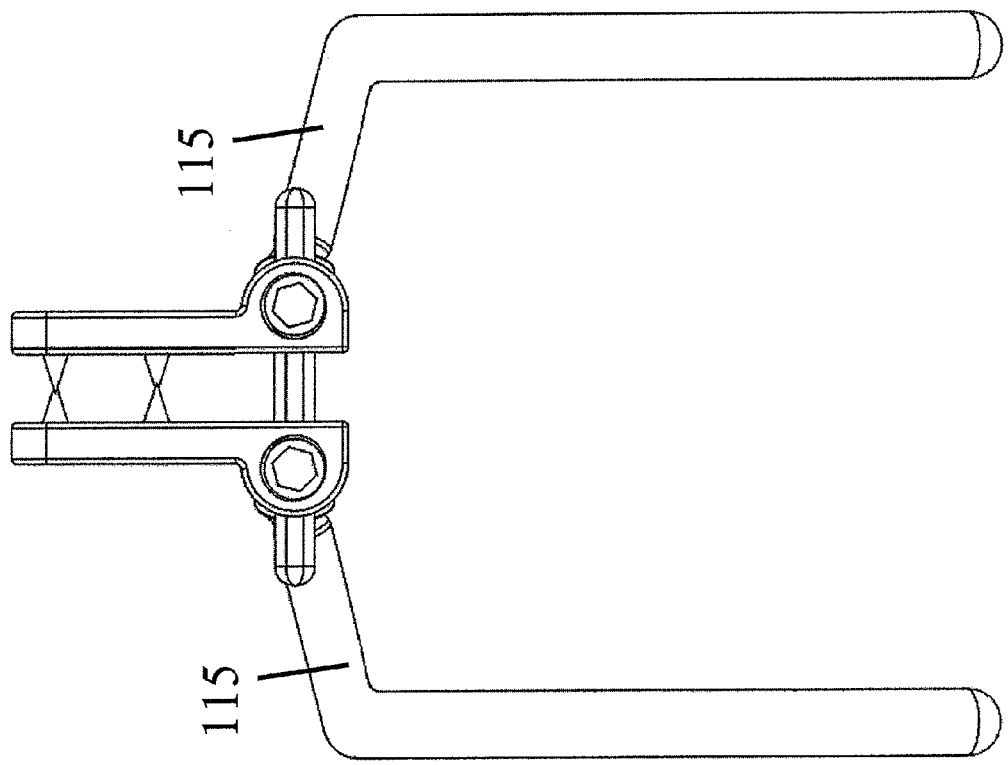
FIG. 22 shows an additional device embodiment that is adapted to fixate multiple vertebral levels.

FIG. 22 shows another embodiment of a device that is similar to the device of FIG. 11. In this embodiment, the rods 115 have a length that is sufficient to span across multiple vertebral levels. This permits the device to be used to fixate multiple vertebral bodies across multiple levels to a spinous process of a single vertebral body.

Figure 23:
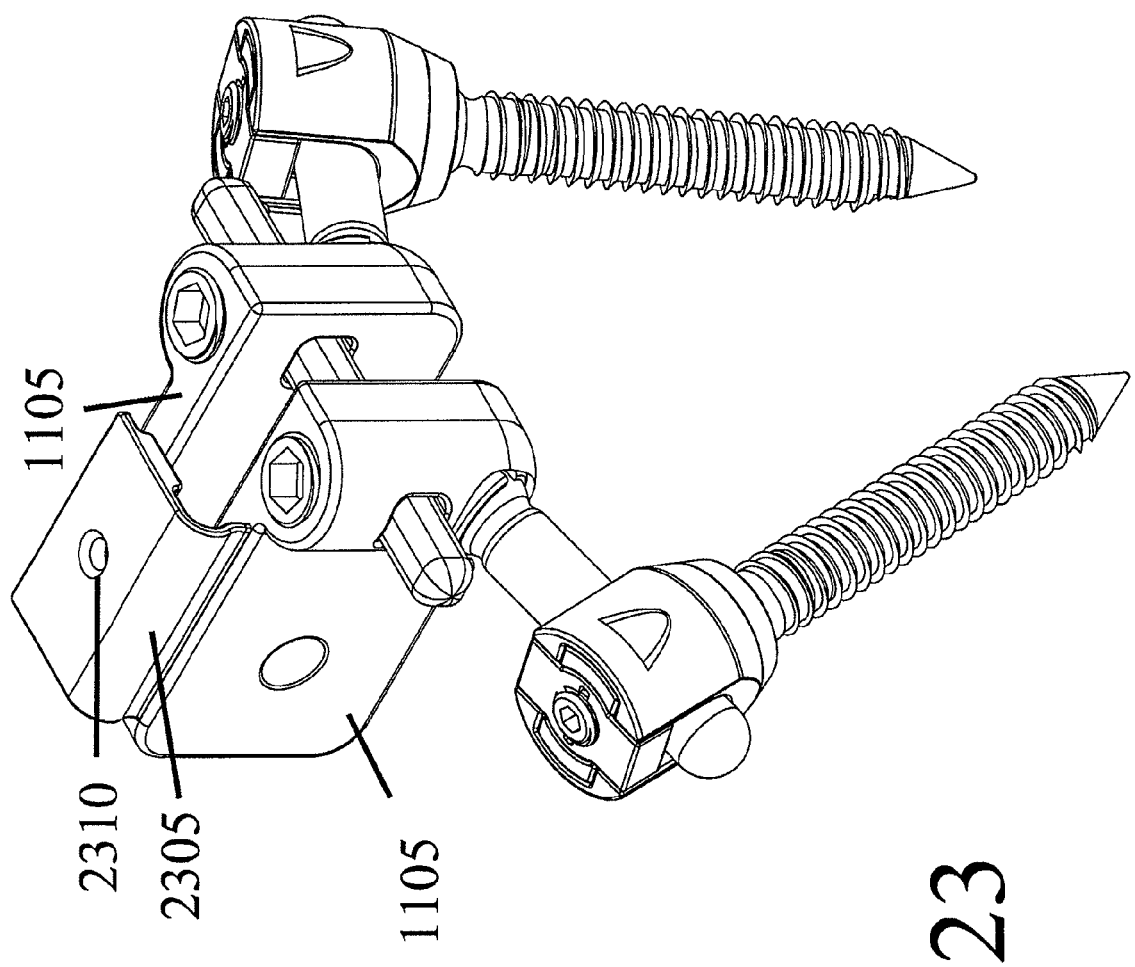
FIG. 23 shows a perspective view of an alternative embodiment of the device shown in FIG. 11.
Figure 25B:
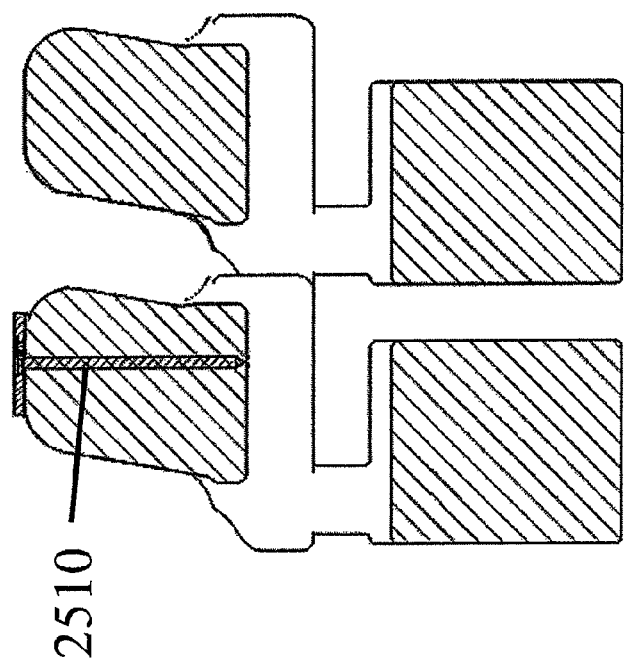
FIG. 25B illustrates a cross-sectional view wherein the spinous process fixation screw is shown.
Figure 25A:
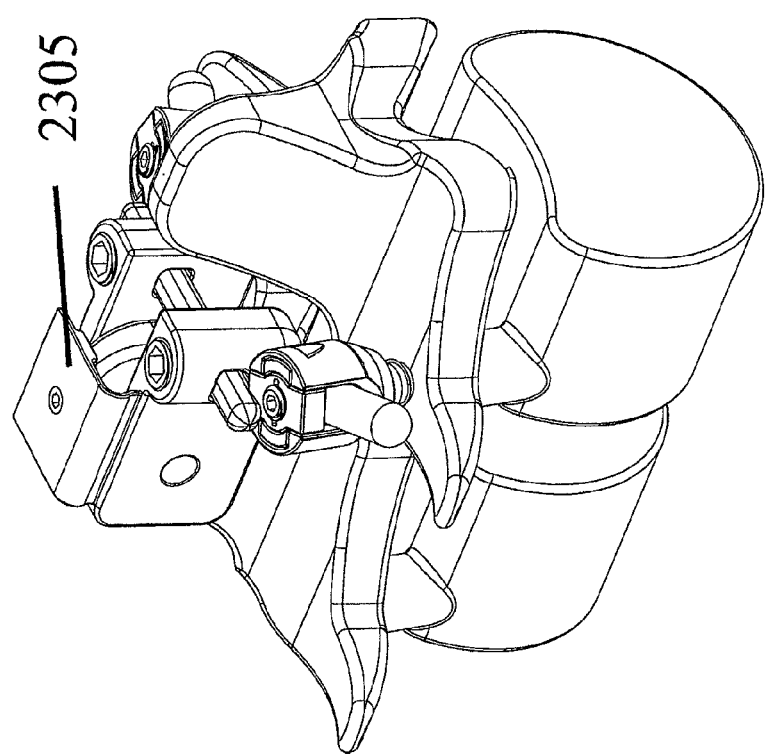
FIG. 25A shows the device of FIG. 23 attached to a spine model.

FIGS. 23 and 24 show an alternative embodiment. In this device, at least one of the central members 1105 has a portion 2305 that extends outwardly and overhangs the space between the central members 1105. The portion 2305 is sized, shaped, and contoured such that it can fit around the spinous process that is positioned between the central members 1105. A bore 2310 extends through the portion 2305. The bore receives a bone fastener, such as a bone screw, that can be driven into the posterior surface of the spinous process and having a posterior to anterior trajectory that substantially follows the long axis of the spinous process. FIG. 25A shows the device of FIG. 23 attached to a spine model. FIG. 25B illustrates a cross-sectional view wherein the spinous process fixation screw 2510 is shown extending through the portion 2305 and into the spinous process.

FIG. 26A shows another embodiment of the device of FIG. 11 wherein rods 115 are replaced with paddle attachment members 2605. FIG. 26B shows an exemplary embodiment of a paddle attachment member 2605. The paddle attachment member 2605 is used in place of a rod 115. The attachment member 2605 has a head that fits into the central member 1105 and also has an opening 2610 that can be coupled to a bone fastener, such as a pedicle screw assembly.

Figure 27:
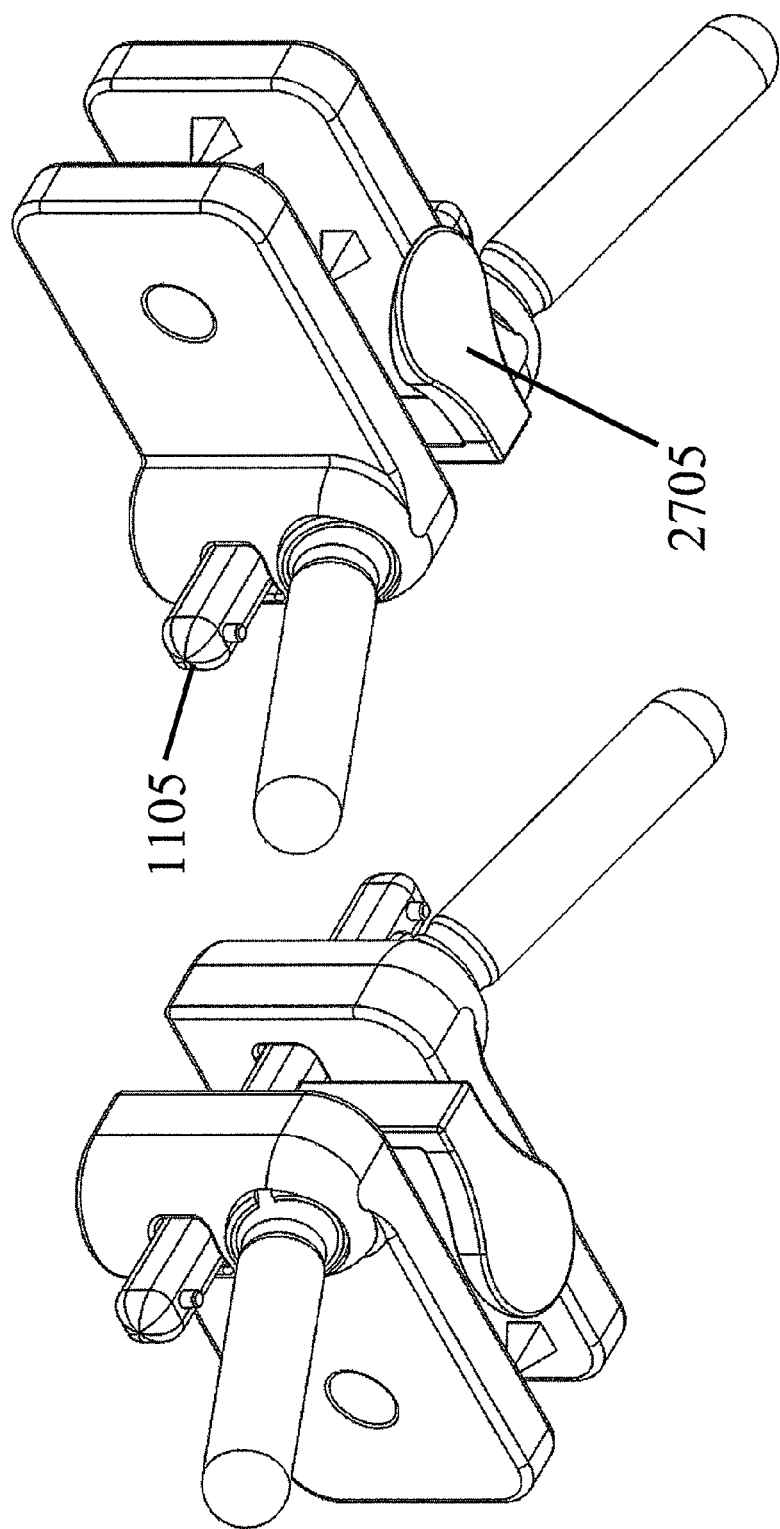
FIGS. 27 and 28 illustrate additional device embodiments.
Figure 28:
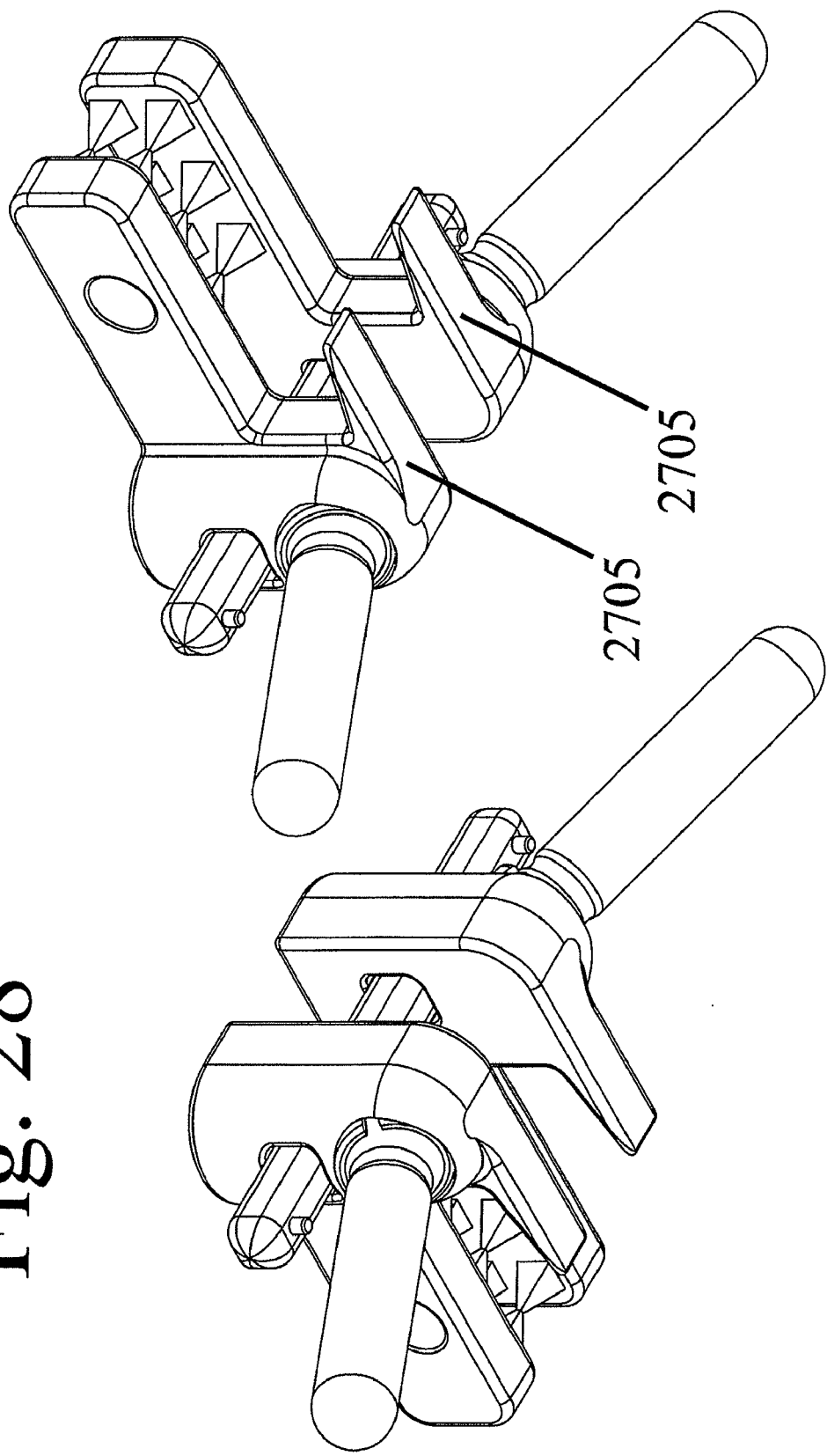

FIGS. 27 and 28 show additional embodiments of the device of FIG. 11. In these devices, a portion 2705 is sized and shaped to capture the inferior surface of the lamina of the upper vertebral bone. In the embodiment of FIG. 27, the portion 2705 extends outward from the rod 1110. In the embodiment of FIG. 28, the portion 2705 extends outward from each of the central members 1105.

Figure 29:
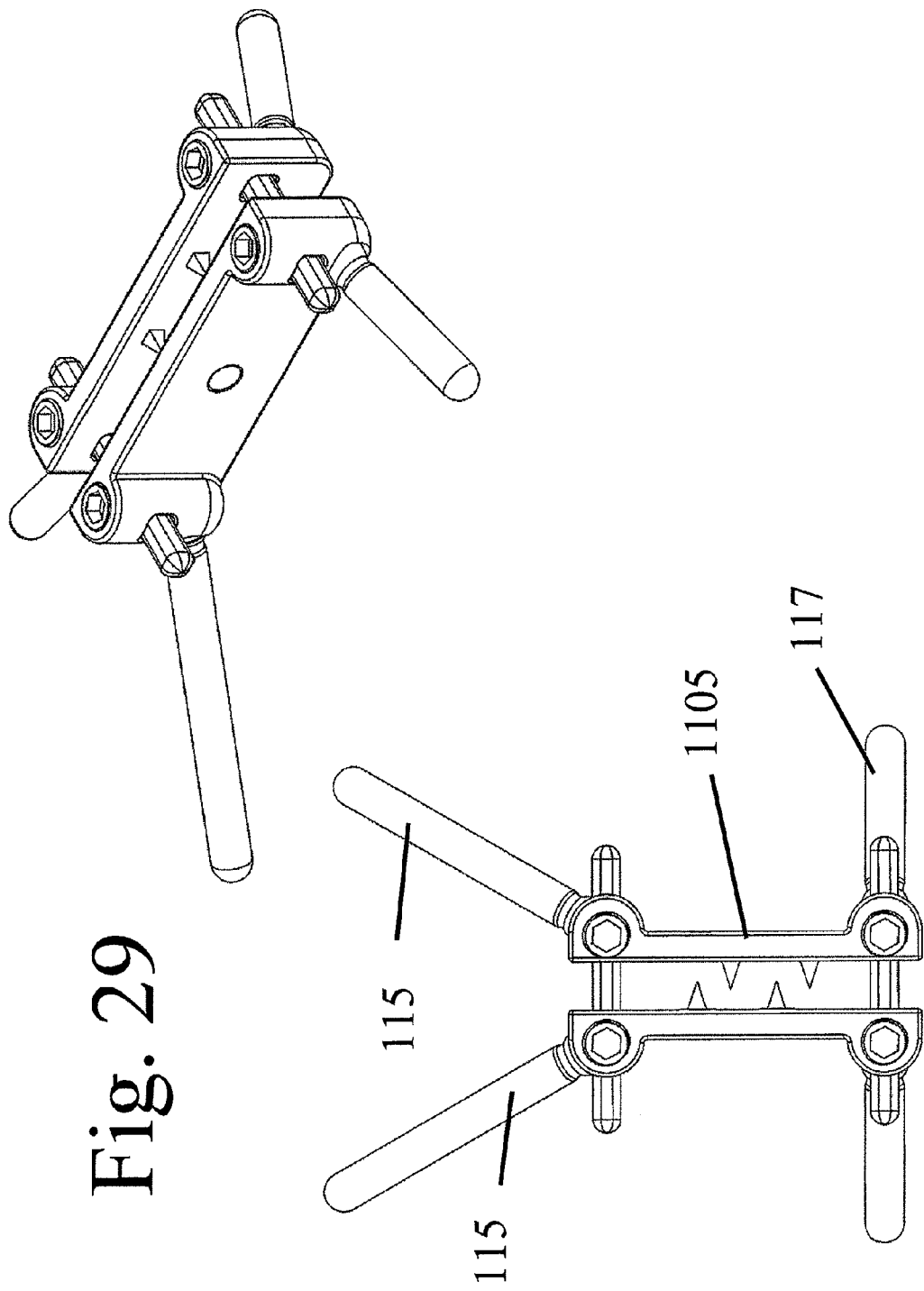
FIG. 29 shows another device embodiment used to fixate three or more vertebral bones.
Figure 30:
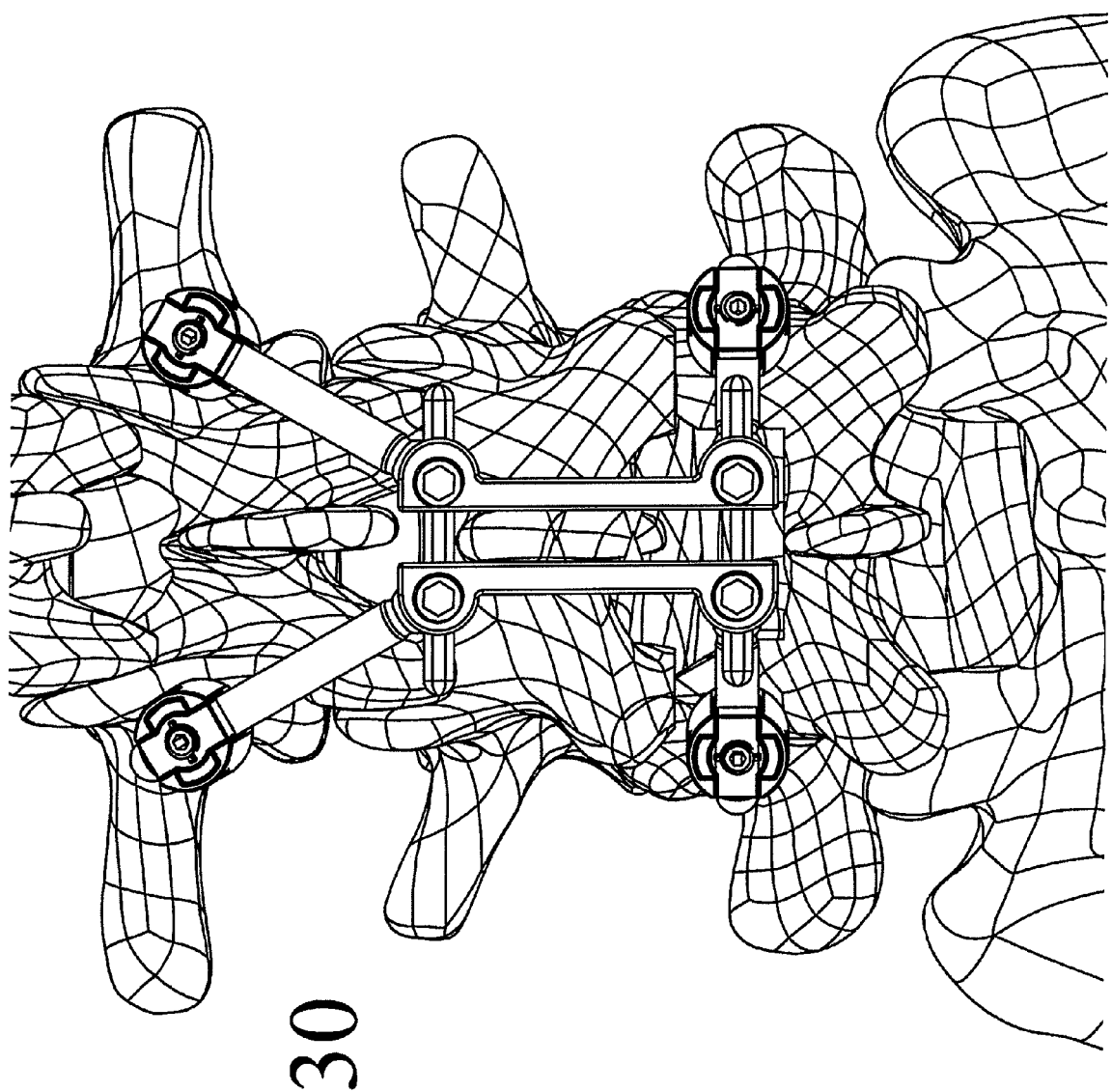
FIG. 30 shows the device of FIG. 29 attached to the spine.

FIG. 29 shows another device embodiment used to fixate three or more vertebral bones. In this embodiment, the central members 1105 are sufficiently long such that the spinous processes of one or more vertebral bodies can fit between the central members 1105. The central members 1105 have barbs or other attachment means that are adapted to secure to the spinous processes. One end of each of the central members has a rod 115 movably attached thereto while the opposed end has another rod 117 movably attached thereto. The rods 115 and 117 can extend outward at any of a variety of orientations and angles relative to the central members. The rods 115 and 117 can be attached to pedicle screw assemblies for attaching the device to adjacent vertebral bodies. Thus, the device is adapted to fixate the spinous process of a middle vertebra to screw fasteners attached to the pedicle portions of an upper and a lower vertebra. FIG. 30 shows the device of FIG. 29 attached to a schematic representation of the spine.

Figure 31:
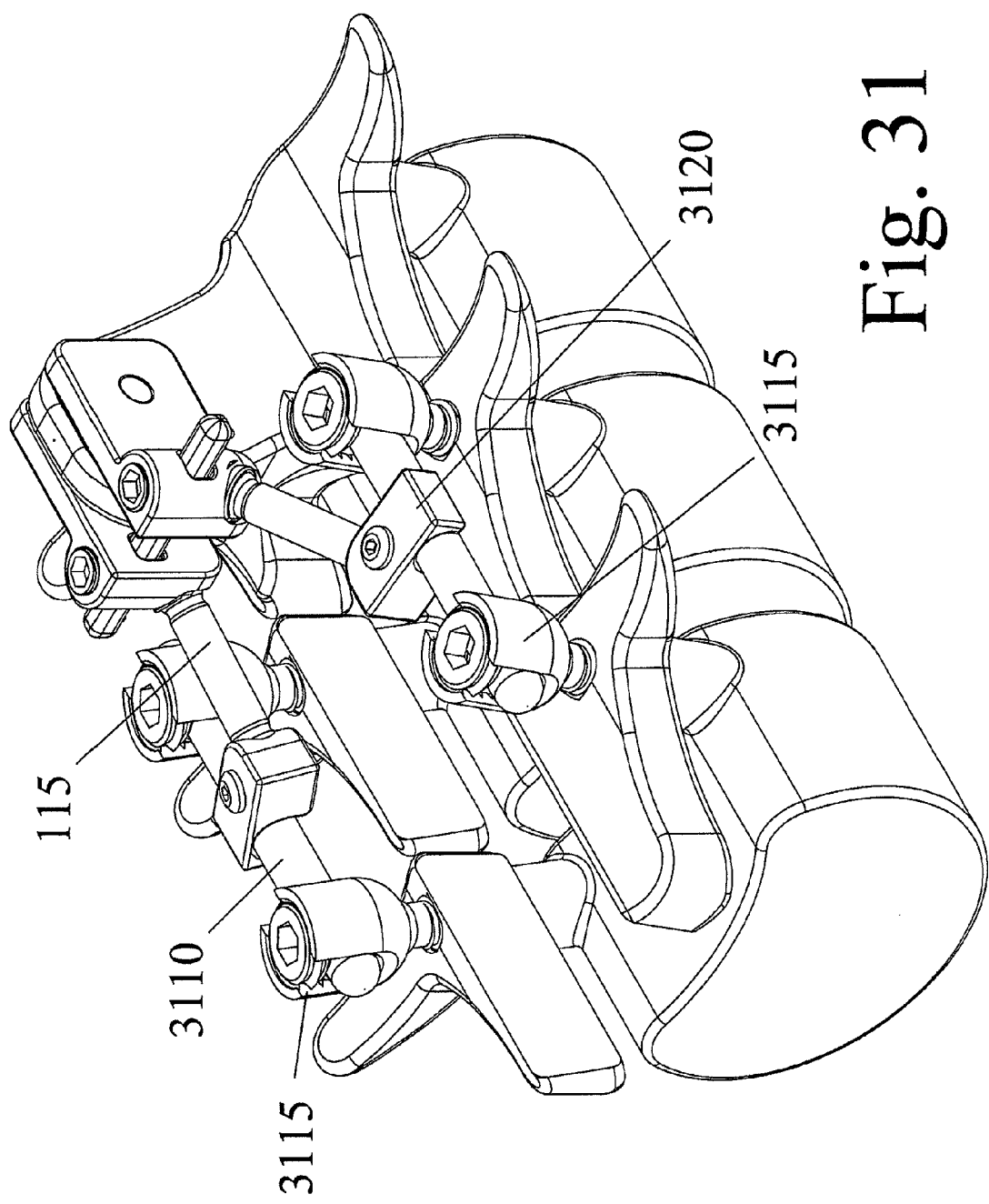
FIGS. 31 to 33 illustrate a device adapted to attach onto existing rod/screw instrumentation.
Figure 32:
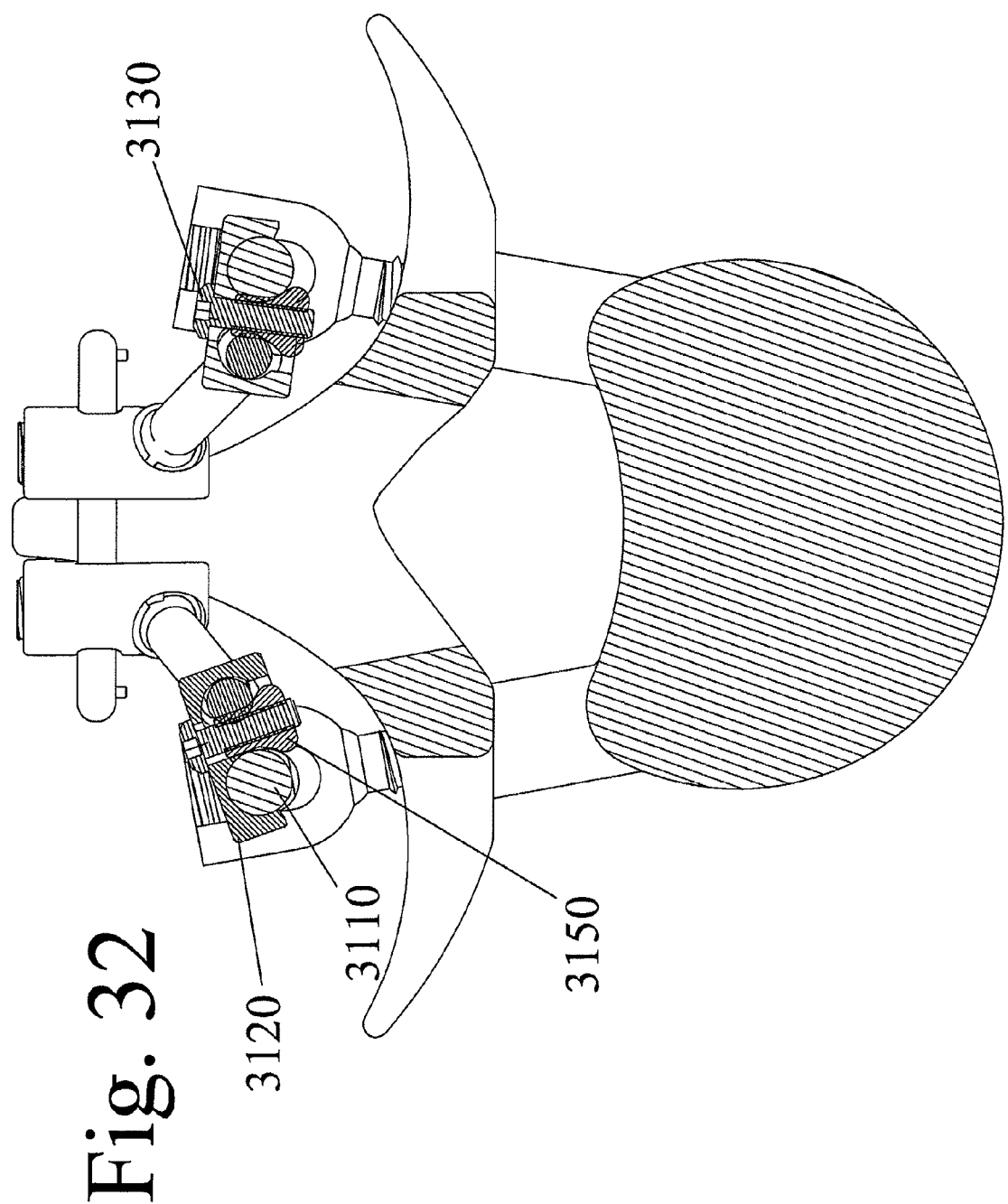
Figure 33:
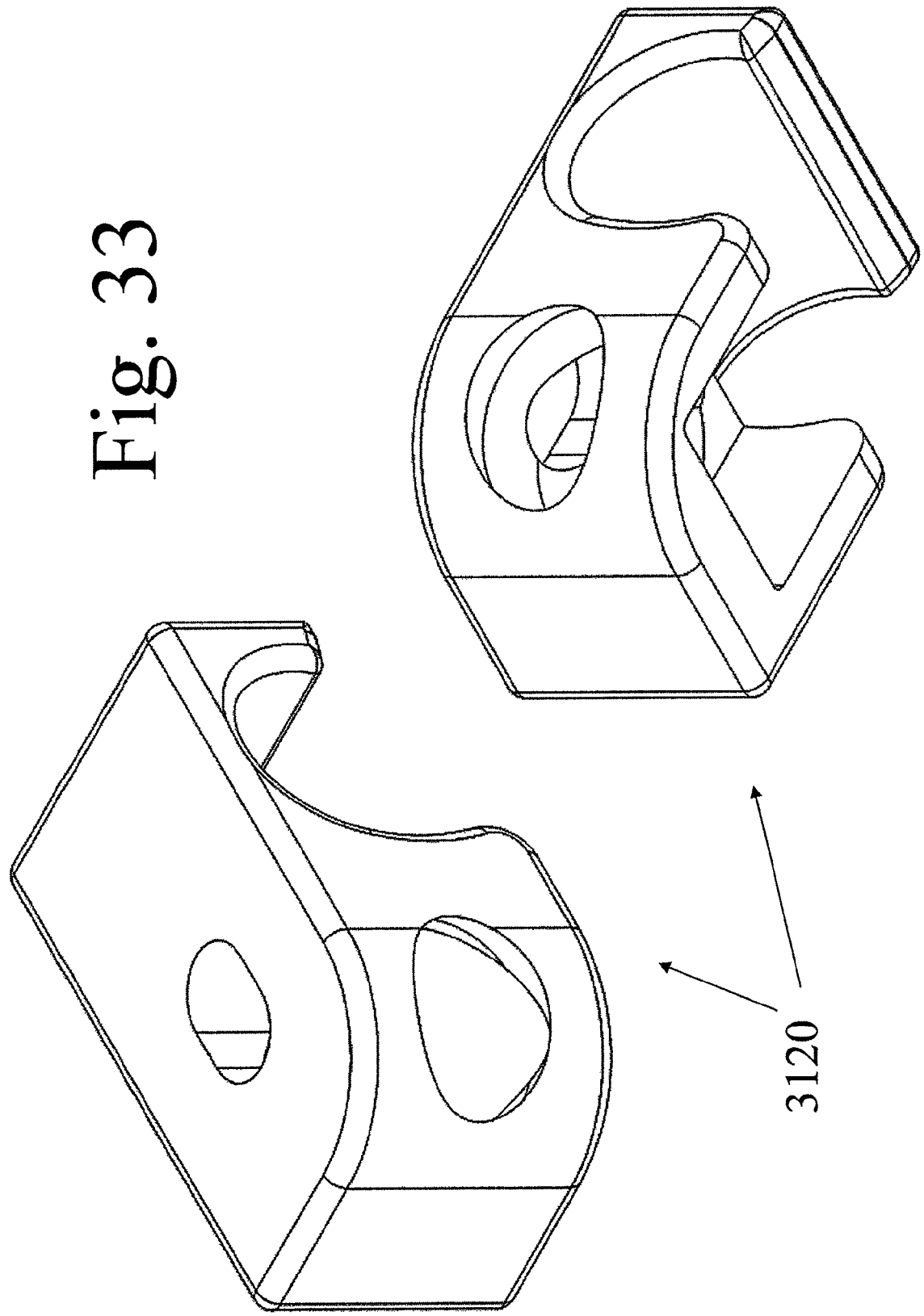

FIGS. 31 to 33 illustrate a device adapted to attach onto existing rod/screw instrumentation and extend the fusion to a additional level. Each of two rods 3110 is attached to a pair of vertebral bodies in a conventional screw/rod fixation arrangement. Each rod 3110 is attached to two pedicle screw assemblies 3115—as shown in FIG. 31. The extension device has a pair of central members 1105 that are positioned on opposed sides of a spinous process of an upper vertebra. Rods 115 extend outwardly from the device. The rods 115 movably attach to the rods 3110 via a pair of brackets 3120. Perspective views of bracket 3120 are shown in FIG. 33. Each bracket is sized to receive a spherical end of rod 115 while also receiving a cylindrical segment of rod 3110. Actuation of the locking screw 3130 of bracket leads to the upward movement of member 3150 and the immobilization of rod 3110 and the special head of rod 115 within bracket 3120. A cross-sectional view of the locking mechanism is shown in FIG. 32.

Figure 34:
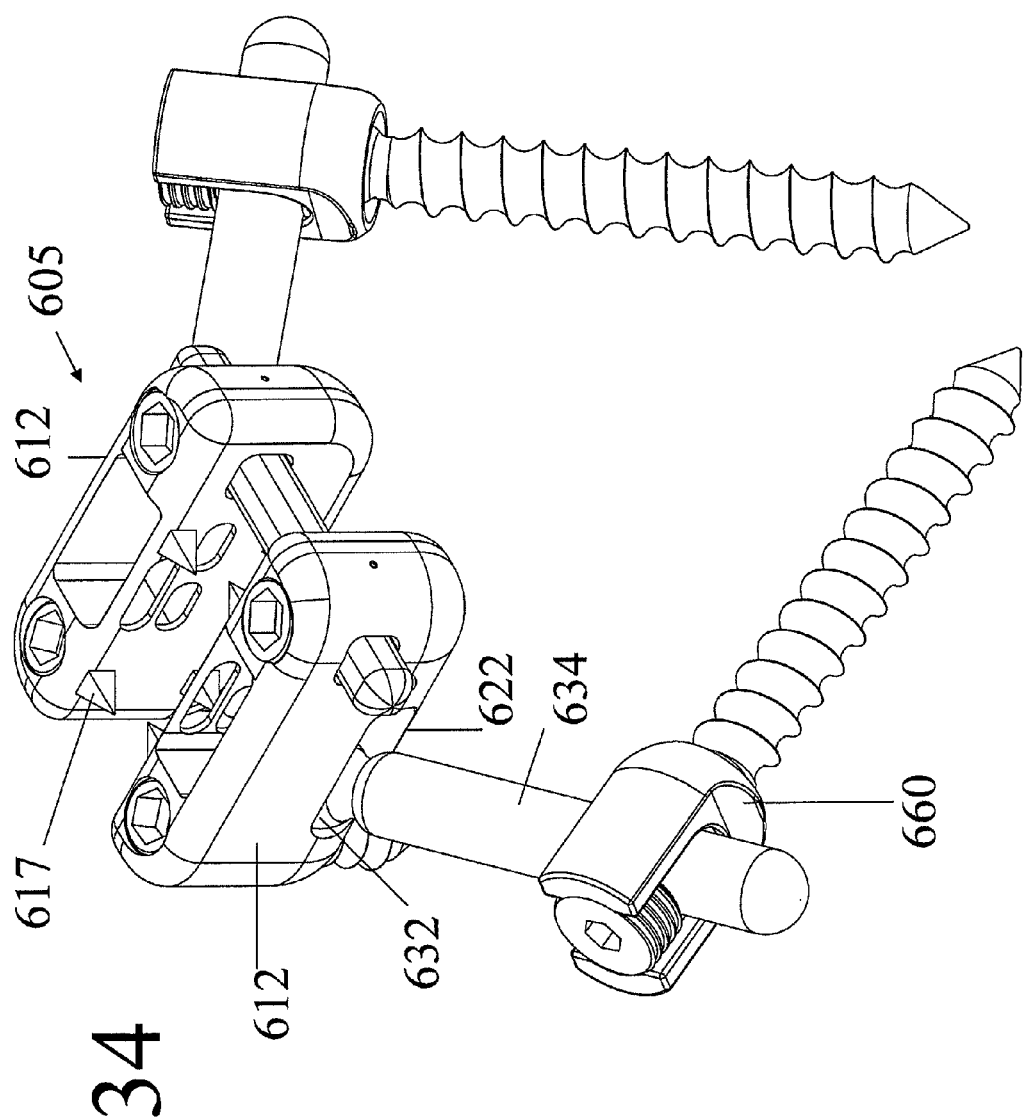
FIG. 34 shows a perspective view of a device embodiment adapted to preserve motion between the vertebral bodies.
Figure 35:
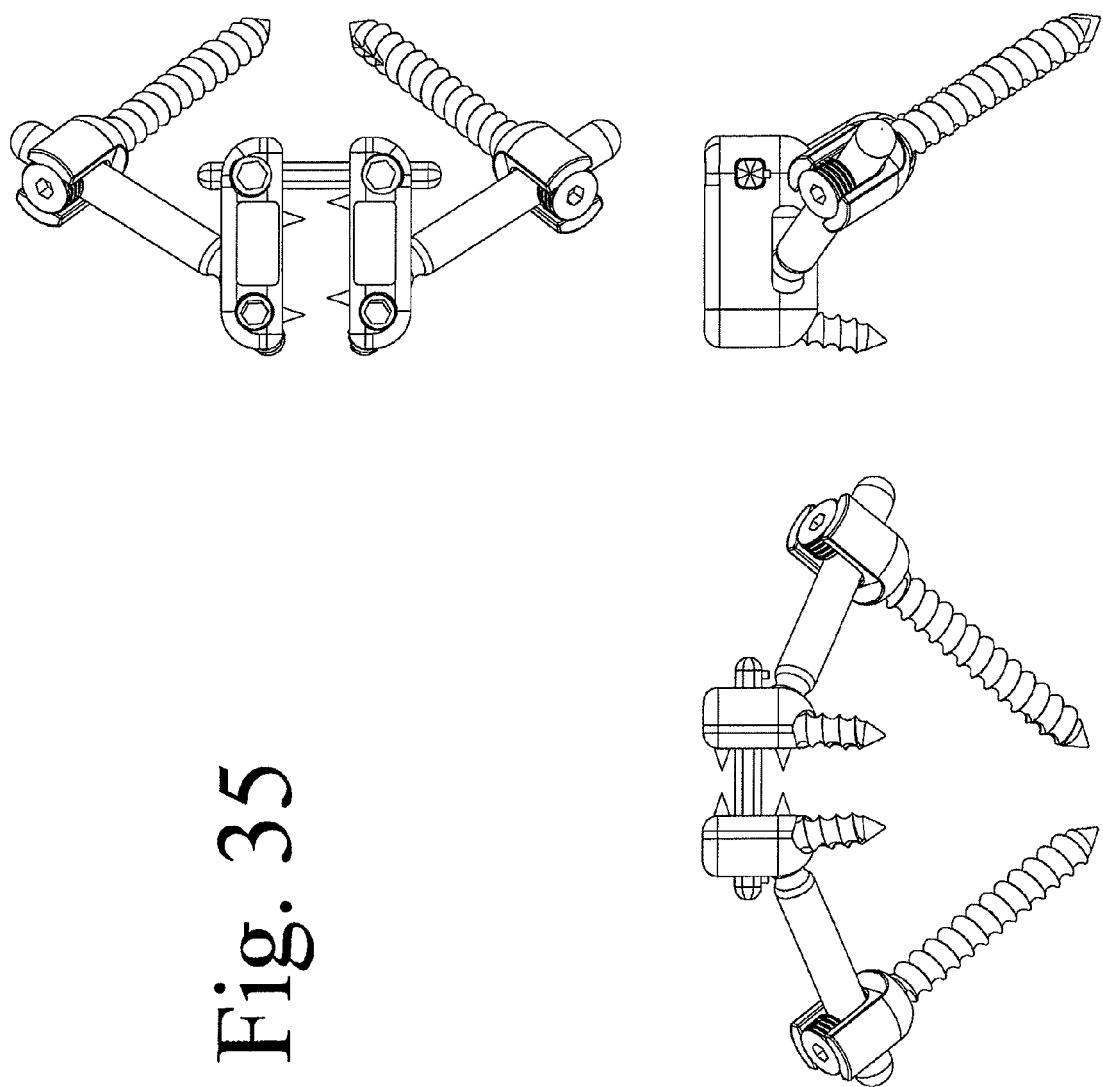
FIG. 35 shows the device of FIG. 34 in multiple orthogonal planes.
Figure 36:
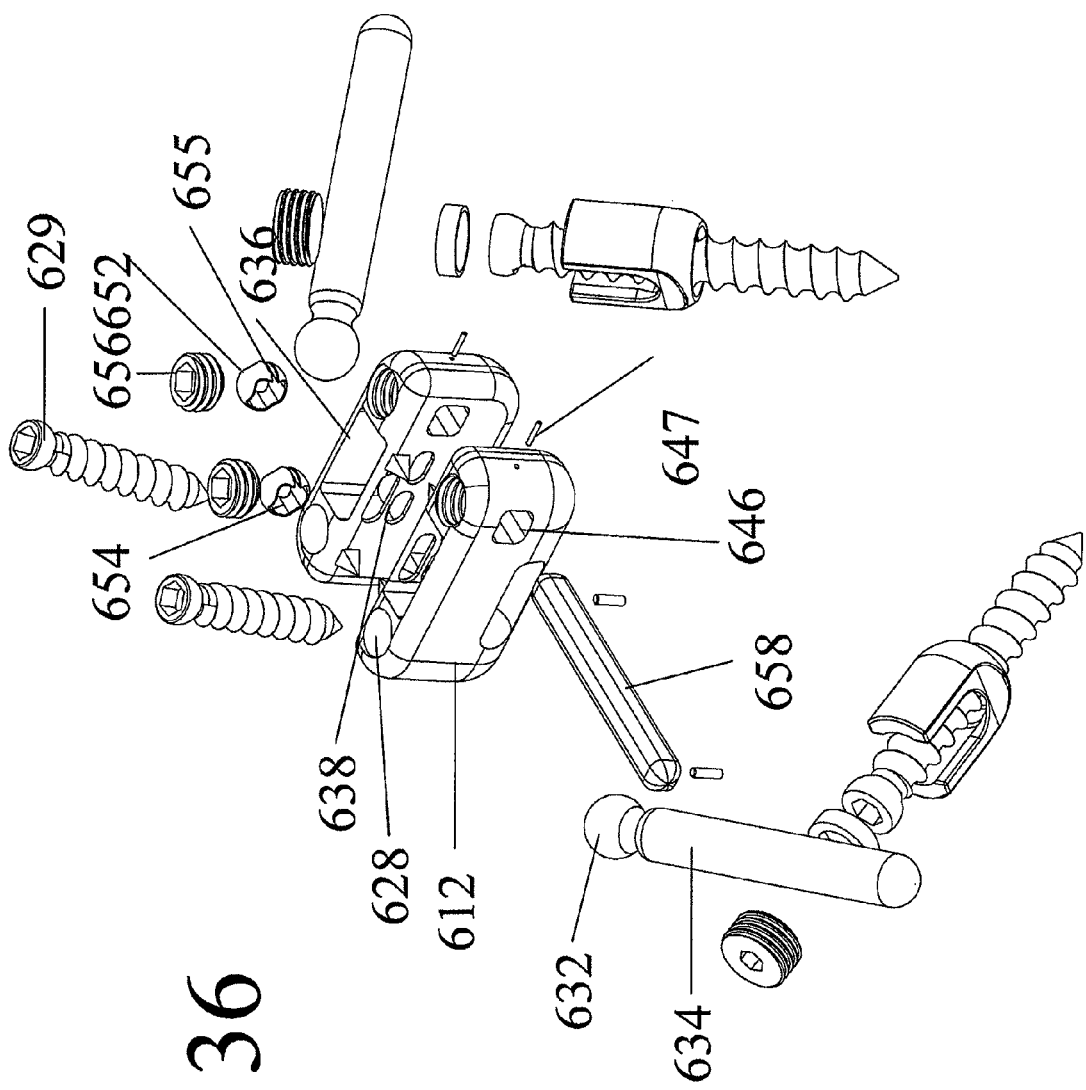
FIG. 36 illustrates an exploded view.

FIG. 34 illustrates a device embodiment 605 adapted to fixate onto the spinous processes of one vertebral bone and bone fasteners anchored into the pedicle portion of an adjacent vertebral body. The device provides controlled movement between the two attached vertebral bones. FIG. 35 shows the device in multiple orthogonal planes and FIG. 36 shows the device components in an exploded view. Each of opposing body members 612 has a top surface, bottom surface, an outer side surface, an inner side surface and a front and back surface. Each medial surface contains spike protrusions 617 that are adapted to be driven into the side surface of a spinous process and serve to increase device fixation onto bone. The lateral surface contains opening 622 of channel 624 that is intended to receive the spherical head 632 of rod 634. Movement of head 632 within channel 624 forms the mobile bearing surface of the implant. A cross-sectional view of head 632 contained within channel 624 is illustrated in FIG. 37A. As shown, head 632 can move unopposed within channel 624. In an alternative embodiment, a spring member is placed within channel 624 so that the position of head 632 is biased against movement away from a default position. Preferably, in the default position, head 632 is positioned at the end of channel 624 that is adjacent to bore 628—as shown in FIG. 34.

The top surface of each body member 612 contains bore 628 adapted to accept a bone fastener 629. Preferably, but not necessarily, bores 628 of the opposing body members 612 are angled in one or more planes so that the seated bone fasteners are not parallel. Non-parallel bore trajectories provide a crossed screw configuration and increased resistance to screw pull-out. As previously discussed, the seated screws may engage any portion of the lamina or spinous process bone but are preferably targeted and placed to engage the junction of the lamina and spinous process.

The top surface of each body member 612 contains a cavity 636 with full thickness bore holes 638 within the medial cavity wall. The cavity is adapted to accept a segment of bone graft or bone graft substitute and to function as a bone containment cage. With time, the graft material within cavity 636 of an implanted device 605 will fuse with the lateral wall of the spinous process and provide an additional attachment point with the underlying bone. Since it contains living bone tissue, ossification of the fusion mass will provide a stronger and more enduring bridge between the implant and vertebral bone than any mechanical fastener.

The top surface of each body member 612 contains a second bore 642, wherein partial thickness bore 642 does not extend through to the bottom surface of the body member. The upper aspect of bore 642 is threaded. Bore 642 is crossed by bore 646, wherein the full thickness bore 646 extends from the lateral to the medial wall of body member 612. Bores 642 and 646 contain the device's locking mechanism. (A cross sectional view through the locking mechanism is shown in FIG. 37B.) Spherical member 652 has central bore 654 and full thickness side cut 655, thereby forming a compressible "C" ring that can be compressed onto the contents of bore 654. In the assembled device, longitudinal member 658 is positioned within central bore 654 and can translate relative to it. With the application of a compressive load onto the outer surface of member 652 by threaded locking nut 656, spherical member 652 is compressed onto longitudinal member 658 and the latter is immobilized within bore 654. Retention pins 645 are used to retain longitudinal member 658 in the assembled device. In the assembled configuration, retention pins 647 are positioned within side cut 655 of spherical member 652 so as to limit the extent of rotation of opposing body members 612.

The spinal level to be implanted has an upper and a lower vertebral bone and the device is attached onto the posterior aspect of the vertebral bones. Prior to device placement, bone fasteners 660 had been placed into the pedicel portion of the lower vertebra on each side of the midline. In addition, each side of the spinous process of the upper vertebra is gently decorticated in order to maximize the likelihood of bone (fusion) mass formation. Each of opposing body members 612 is placed on an opposite side of the spinous process of the upper vertebra. A compression device (not shown) is used to compress each body member 612 onto a side of the spinous process and drive the spike protrusions 617 into the bone surface. With the compression device still providing a compressive force, the distal ends of rods 634 are positioned into the rod receiving portions of bone fasteners 660. Preferably, each head 632 is positioned at the end of channel 624 immediately adjacent to bore 628 prior to locking bone fasteners 660 onto rods 634. This configuration assures that vertebral extension is limited to the position set at the time of surgery. The locking nuts of the fasteners are then actuated so that each rod 634 is locked within the respective fastener 660. Locking nuts 656 of device 605 are then actuated, locking the device's locking mechanism and immobilize opposing body member 612 and the interconnecting longitudinal member 658 relative to one another. The compression device is removed, leaving the device rigidly attached to the upper and lower vertebral bones. Preferably, but not necessarily, cavity 636 is packed with bone graft or bone graft substitute so that, with time, a bone fusion mass connects the device to the side wall of the spinous process. If desired, a bone fastener 629 can be placed through each bore hole 628 into the underlying bone and further increase device fixation onto bone.

It is important to note that spike protrusions 617 and fastener 629 provide immediate device fixation to the upper vertebral level. With time, these fixation points may weaken from the cyclical device loading that invariably results during routine patient movement. Formation and ossification of the bone fusion mass contained within cavity 636 provides long-term fixation for the device. In contrast to spike and screw fixation, the fusion mass will increase in strength with time and provide a more permanent attachment point for the device. In this way, the immediate fixation of the spike and fasteners and the long-term fixation of the fusion mass compliment one another and provide optimal fixation for the device.

After device implantation, certain movements between the upper and the lower vertebras are permitted while other movements are limited. For example, the illustrated embodiment permits forward flexion of the upper vertebra relative to the lower vertebra. However, extension is limited by the position set at the time of implantation (that is, the position of head 632 within channel 624). Anterior translation of the upper vertebral bone relative to the lower vertebral bone is significantly limited so that aberrant motion resulting in spondylolisthsis is prevented. Lateral flexion between the vertebral bones is permitted but to a lesser degree than that of normal physiological vertebral motion. Vertebral rotation is substantially eliminated.

These limitations are determined by the interaction of heads 632 with channels 624 and can be varied by the shape and/or orientation of one or both of these structures. For example, extending the diameter of channel 624 in a medial to lateral direction will permit an increase in vertebral rotation. Further, a channel with lesser medial to lateral diameter at one end and a greater medial to lateral diameter at another end will permit a variable degree of rotational movement, wherein the extent of rotation depends of the extend of anterior flexion. This configuration can simulate physiological vertebral motion, wherein grater vertebral rotation is permitted in anterior flexion than in extension. As can be easily seen, numerous alternative motion characteristics can be produced by one of ordinary skill in the art through the simple manipulation of the shape and/or orientation of heads 632 and/or channels 624. In addition, malleable members can be placed within channel 624 so that the position of head 632 is biased towards a default position and movement away from that position is opposed.

Figure 38:
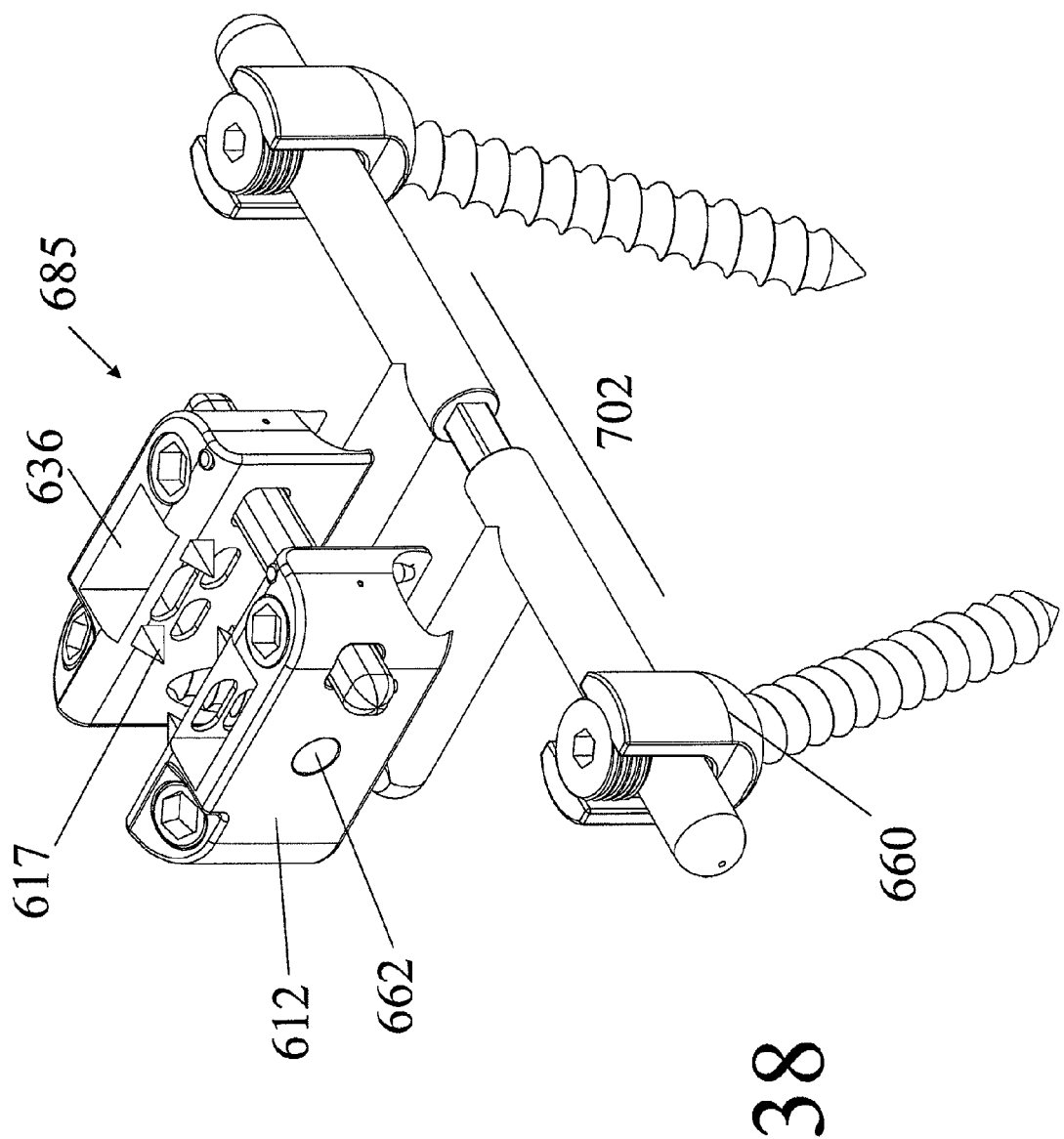
FIG. 38 illustrates a perspective view of an additional device embodiment.
Figure 40:
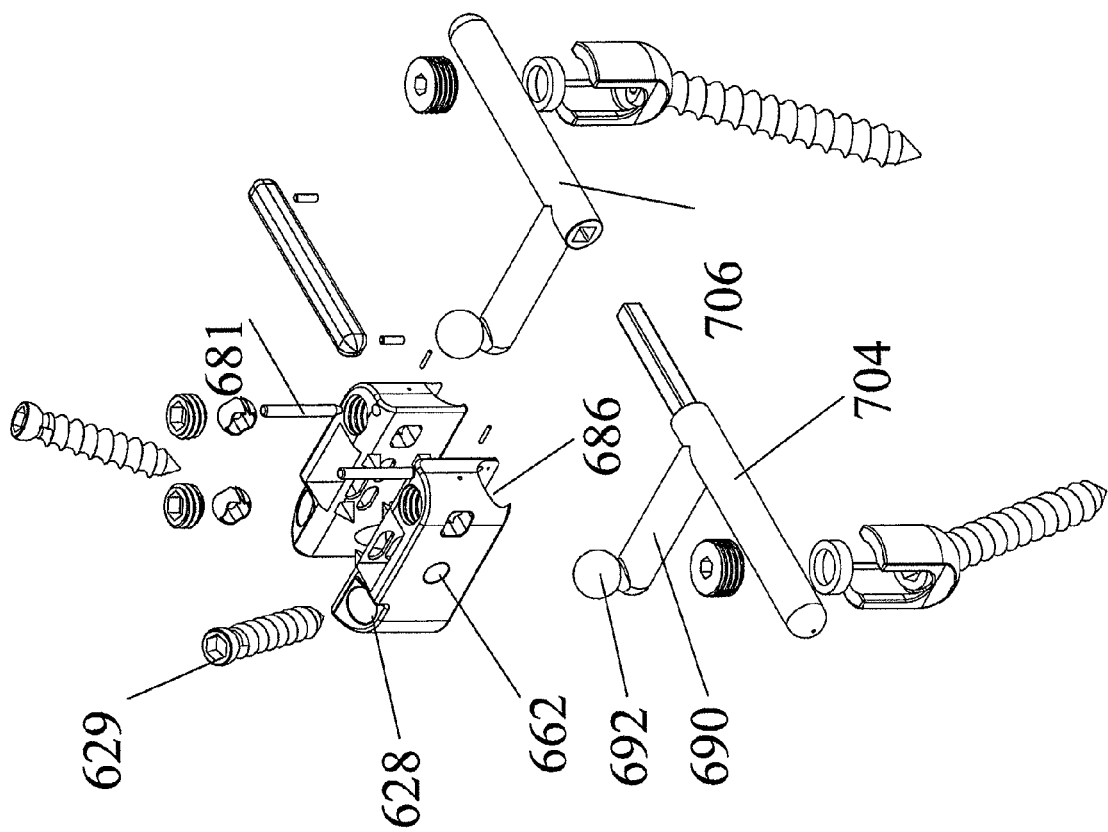
FIG. 40 illustrates an exploded view.
Figure 41:
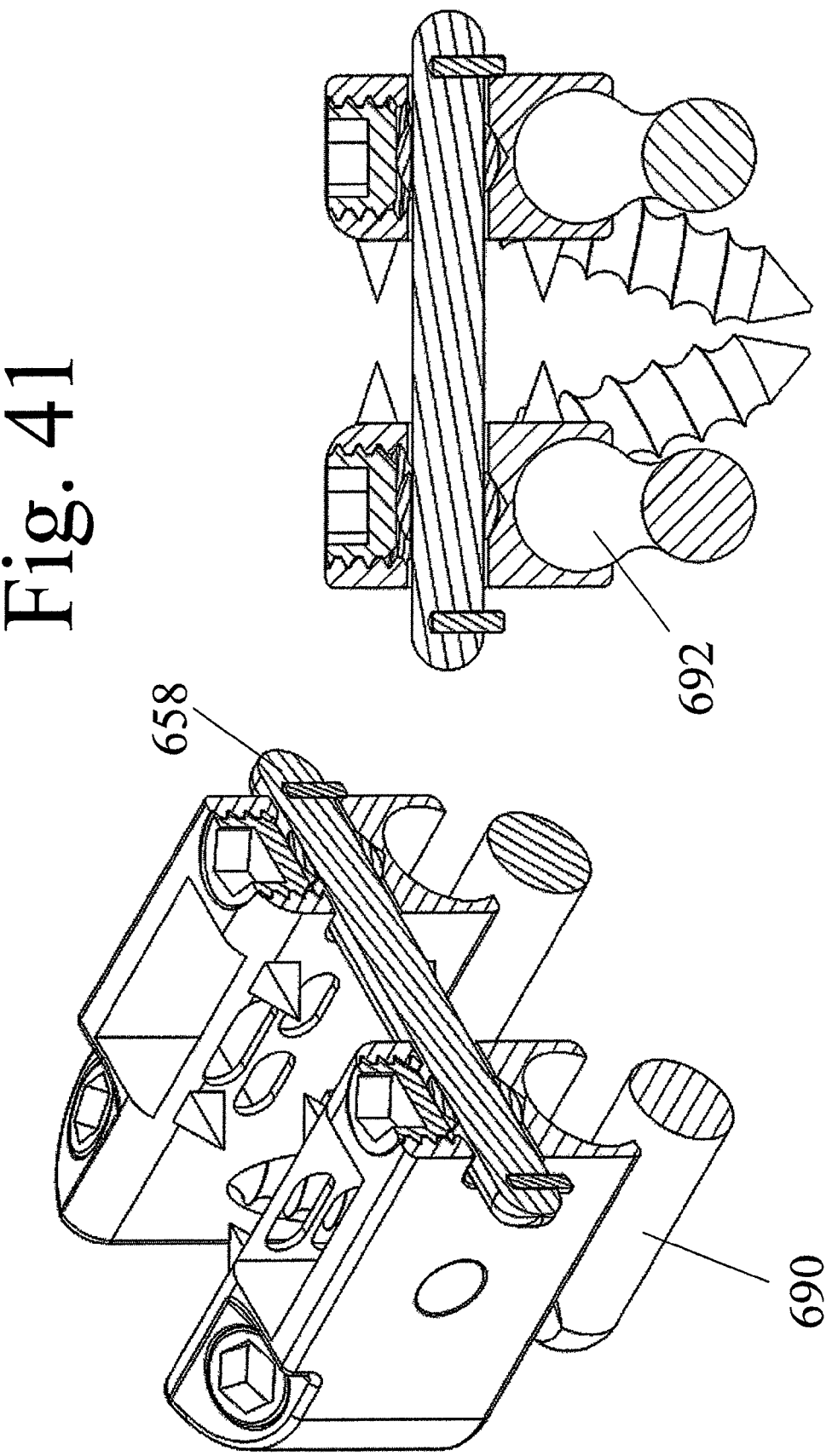
Figure 43:
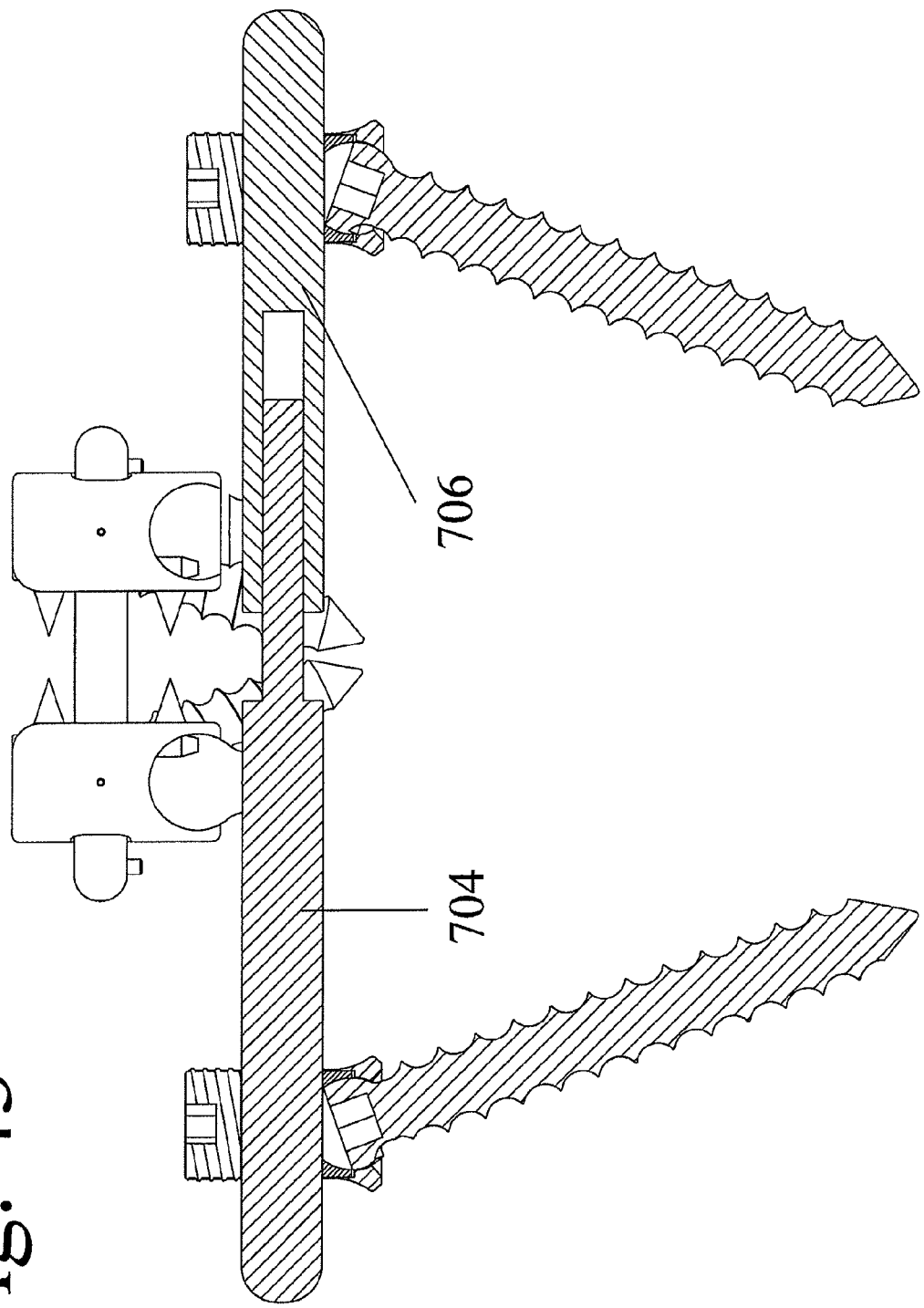

An alternative embodiment is shown in FIG. 38. While similar to the preceding embodiment, this device provides a cross-member that inter-connects the bone fasteners 660 so as to obviate the possibility of fastener rotation (along its long axis) within the pedicle portion of the bone. The cross member also increases the resistance to fastener pull-out from the lower vertebral bone. FIG. 39 shows the device in multiple orthogonal planes. An exploded view is shown in FIG. 40 and multiple cross-sectional views are shown in FIGS. 41, 42 and 43.

Device 685 is adapted to fixate onto the spinous processes of one vertebral bone and bone fasteners anchored into the pedicle portion of an adjacent vertebral body. As before, each of opposing body members 612 has side spikes 617, a central cavity 636 adapted to accept a bone forming graft, and a locking mechanism adapted to immobilize body members 612 to interconnecting longitudinal member 658. (A section view through the locking mechanism is shown in FIG. 41.) The top surface of each body member 612 contains bore 628 adapted to accept a bone fastener 629. Side indentations 662 receive the compression device during device implantation.

The inferior surface of each body 612 contains opening 682 of channel 686. Head 692 of rod 690 travels within channel 686 and forms the mobile bearing surface of the implant. Retention pin 681 (FIG. 40) is used to retain head 692 within channel 682 and prevent device disassembly. As before the motion characteristics permitted by the implant are determined by the interaction of heads 692 with channels 686 and can be varied by the shape and/or orientation of one or both of these structures. (A section view through the bearing surface is shown in FIG. 42.) Examples of the possible configuration changes were previously discussed. In addition, malleable members can be placed within channel 682 so that the position of head 692 is biased towards a default position and movement away from that position is opposed.

Interconnecting rod 702 is used to attach the device onto the bone fasteners imbedded within the pedicel portion of the lower vertebral body. Rod 702 is comprised of telescoping segments 704 and 706 so that the rod length may be varied. Segment 704 contains rectangular protrusion 704 that, in the assembled state, is housed with a complimentary bore within segment 706. A cross-sectional view through rod 702 is shown in FIG. 43. A side rod 690 with head 692 (bearing surface) is contained in each of segments 704 and 706—as illustrated. The procedure for placement of device 685 is similar to the placement procedure previously described for device 605.

Figure 44:
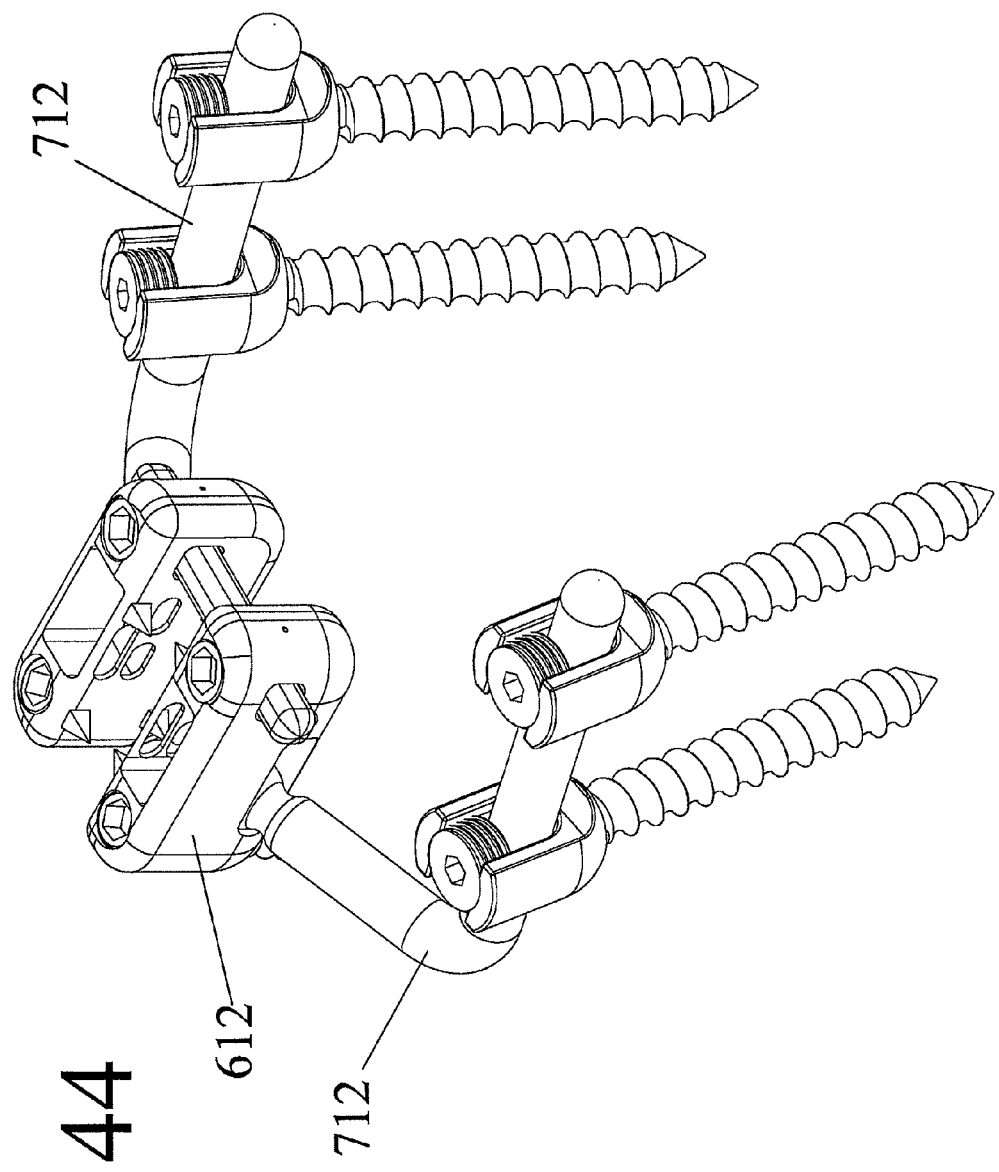
FIG. 44 shows a perspective view of an alternate embodiment of the motion preservation device.
Figure 45:
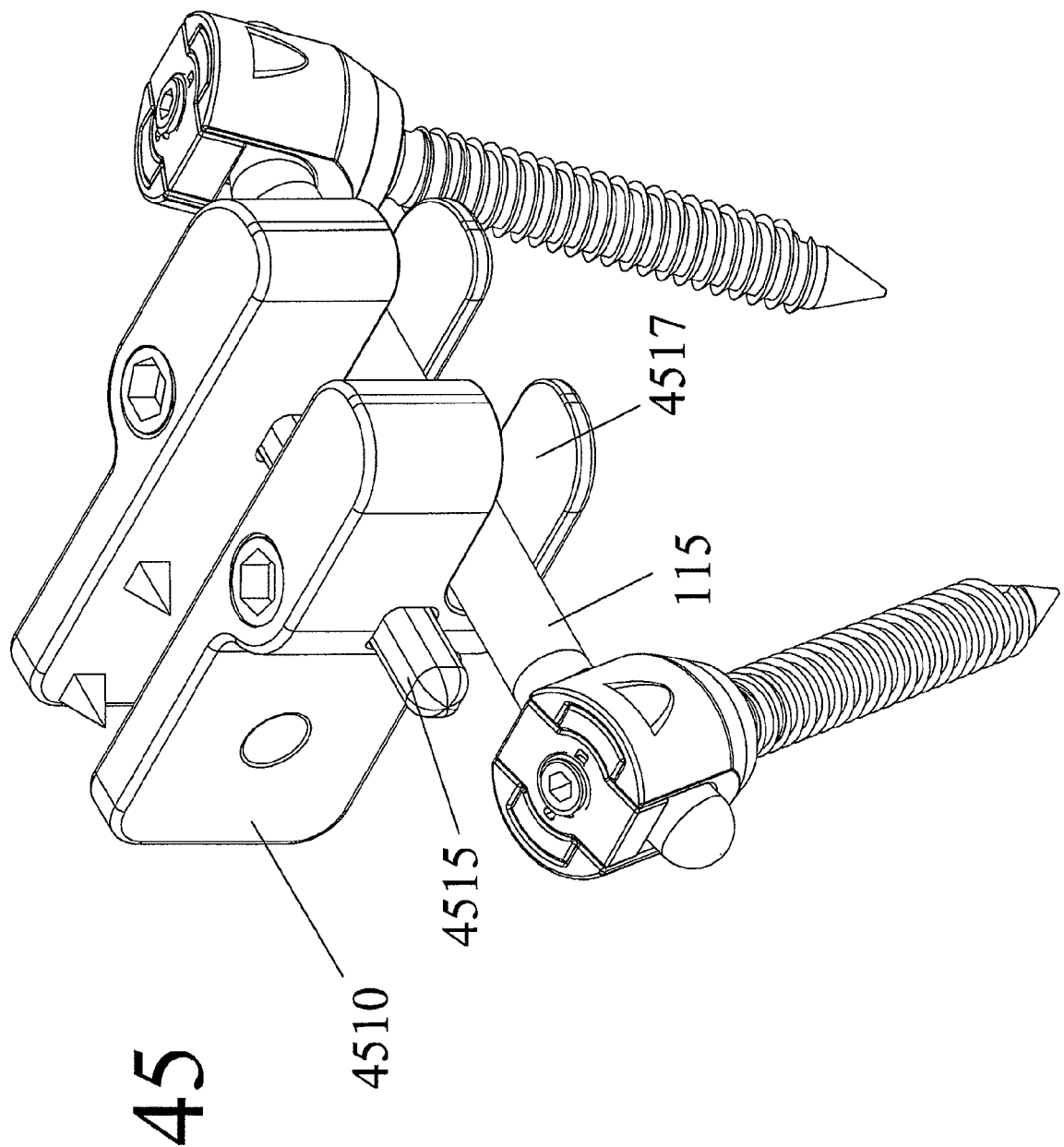
FIG. 45 illustrates a perspective view of an additional device embodiment.
Figure 47:
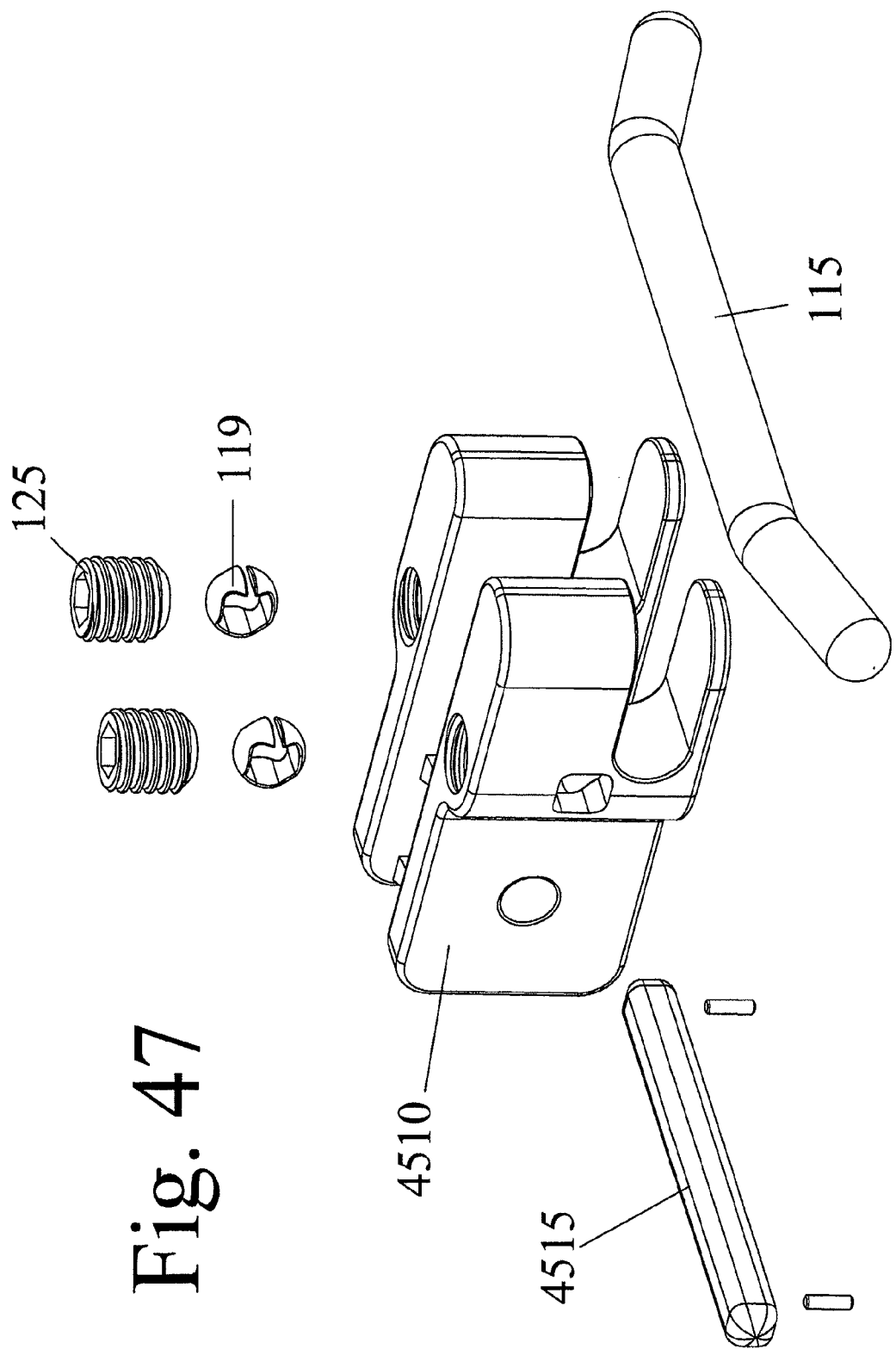
FIG. 47 illustrates an exploded view.

An alternative device embodiment is illustrated in FIG. 44. While the portion of the device that attaches onto the spinous process of the upper vertebral bone is largely identical to that of device 605, the current embodiment contains two contoured rods 712 that are adapted to attach bone fasteners at multiple vertebral levels. In use, bodies 612 attach onto the spinous process segment of an upper vertebral while contoured rod 712 attaches onto bone fasteners that are attached onto a middle and a lower vertebral level. As before, the bone fasteners are preferably, but not necessarily, anchored into the pedicle portion of the middle and lower vertebral bones. In this way, the current embodiment provides a hybrid device that permits vertebral movement between a first and second vertebral bones and complete immobilization (and fusion) between a second and third vertebral bone. Clearly, additional fasteners can be attached to contoured rod 712 to immobilize additional vertebral levels. This device is particularly adapted for use within the lower lumber spine where it is frequently desirable to immobilize and fuse the S1 and L5 vertebral levels and preserve motion between the L5 and L4 vertebral levels.

FIG. 45-48 show another embodiment of a device. The device includes central members 4510 that are slidably attached to a rod 4515 that extends through a bore 4513 in both of the central members 4510. Each of the central members 4510 has a u-shaped slot 4517 that is sized to receive a contoured rod 115. As in the previous embodiments, the central members are positioned on opposed sides of a spinous process and engaged thereto via spikes or barbs on the interior surface of the central members.

Figure 48:
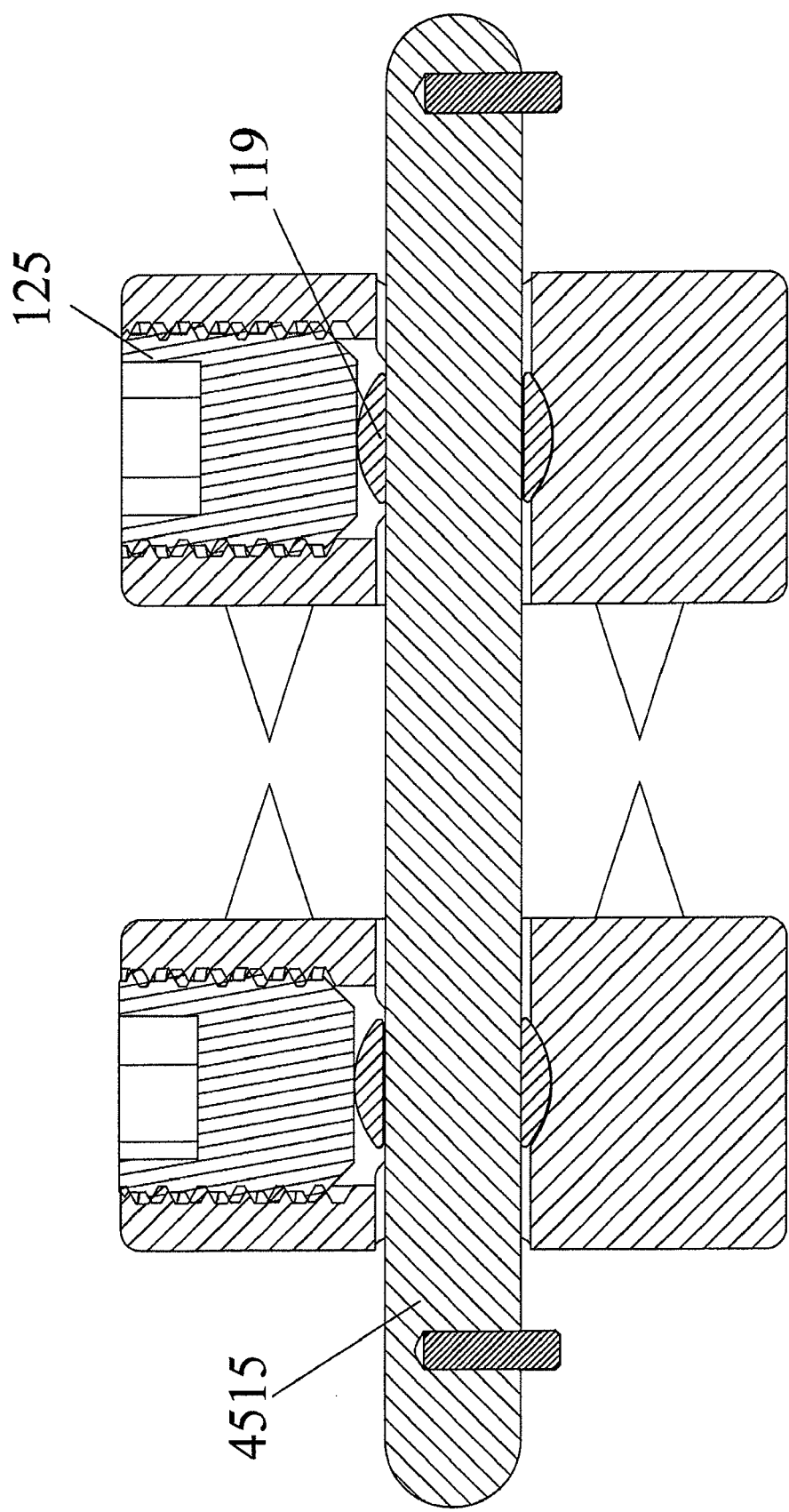
FIG. 48 shows a cross-sectional view through the locking mechanism.

A pair of locking nuts 125 are positioned within boreholes of central members 4510 and adapted to produce a compressive force onto "C" ring 119 and interconnecting rod 4515. A cross-sectional view of the locking mechanism is illustrated in FIG. 48. As illustrated in prior embodiments, each ember 4510 can move relative to rod 115 in one or more planes while in the unlocked state. With actuation of locking nuts 125, members 4510 and rod 4515 are immobilized relative to one another. Rod 115 is affixed to fasteners that are attached to the pedicle portion of the lower vertebral level. Rod is freely movable within slot 4517. In use, the device will preserve vertebral motion but prevent abnormal translational movement that produces spondylolisthesis.

Figure 50:
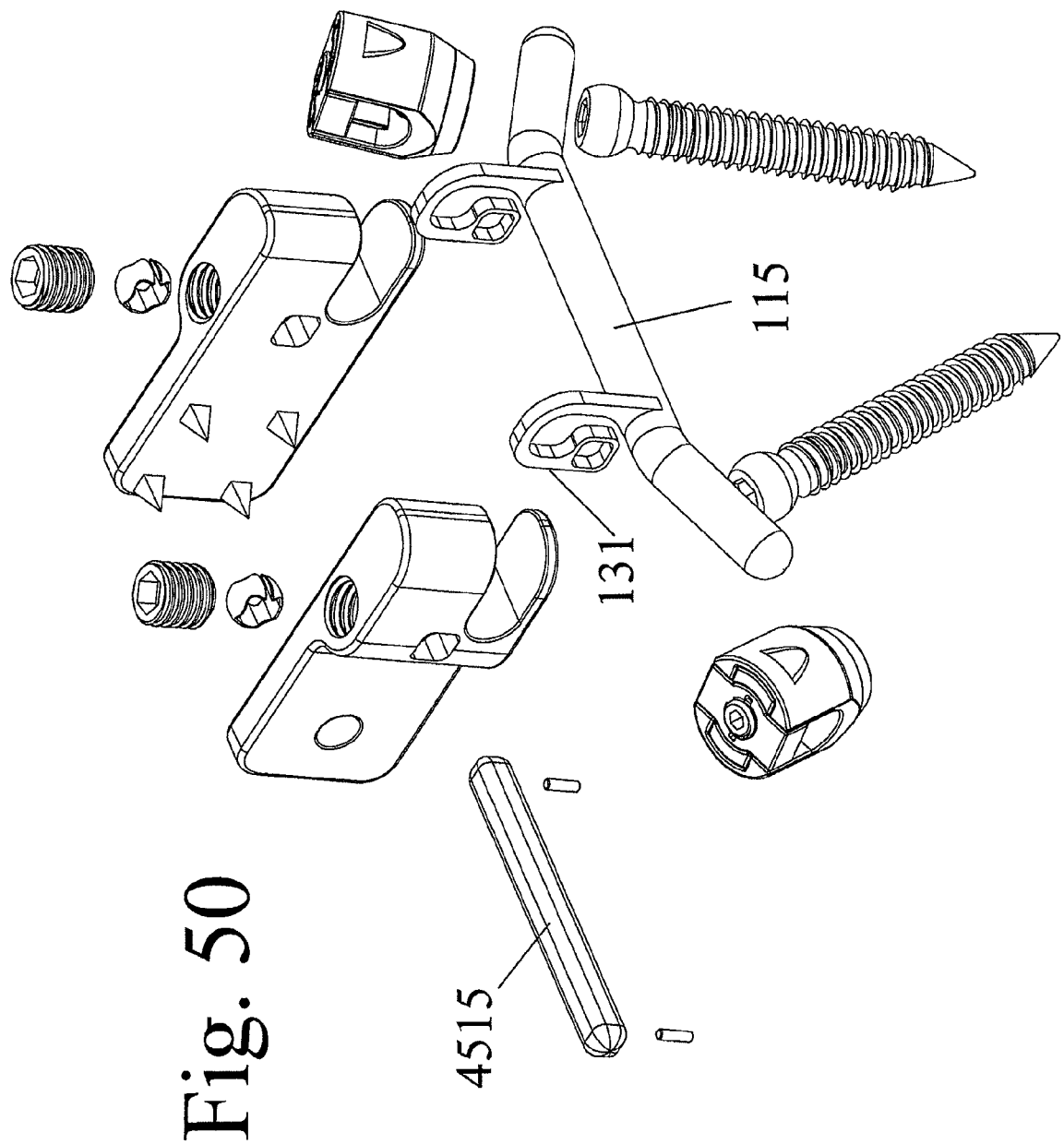
FIG. 50 shows an exploded view of the device of FIG. 49.
Figure 51:
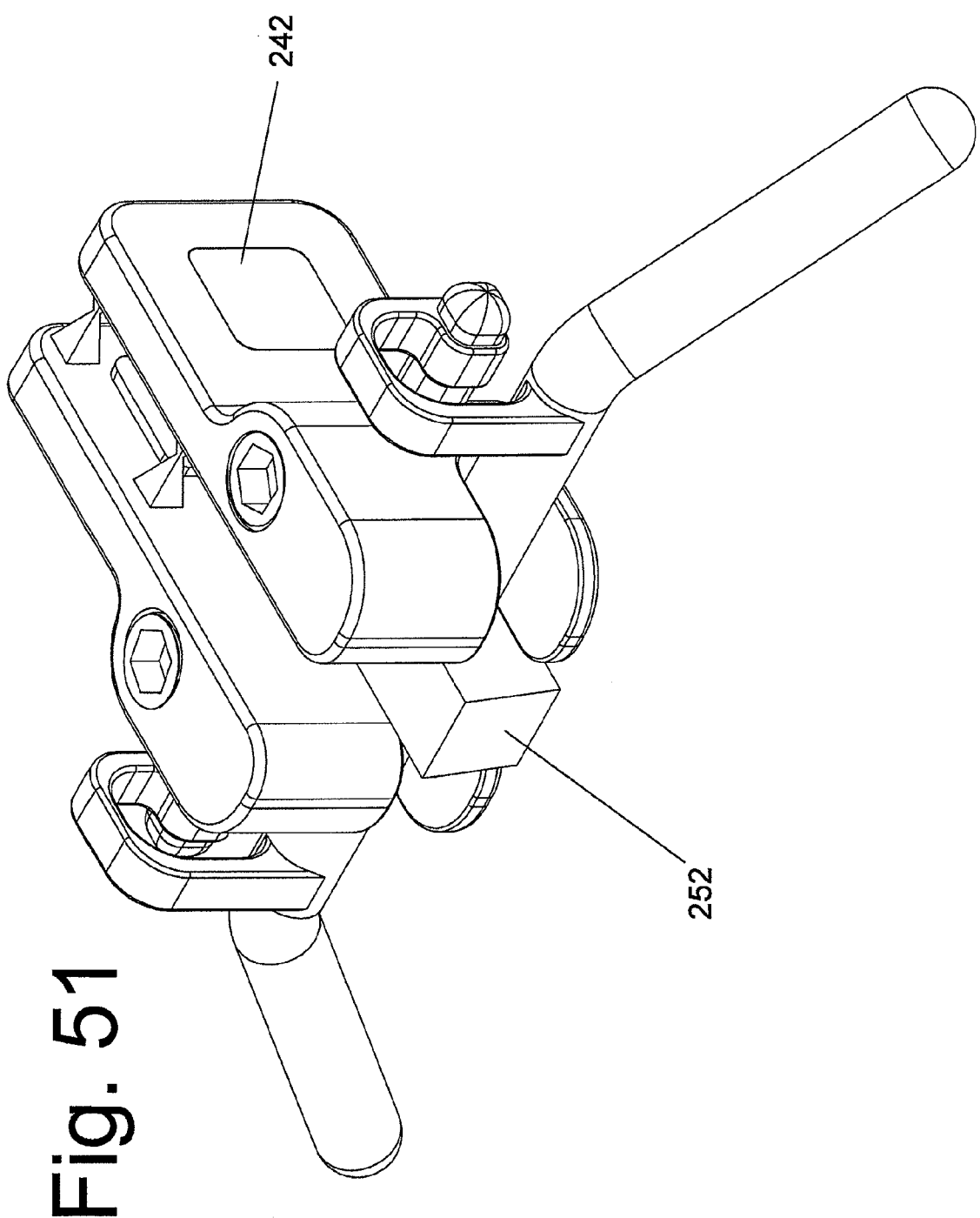
FIG. 51 shows an alternative embodiment of the device in FIG. 49.

FIG. 49 shows perspective views of an additional device embodiment while FIG. 50 illustrates an exploded view. The present embodiment is similar to the preceding embodiment with the exception of placement of malleable members 131 between the interconnecting rod 4515 and rod 115. The malleable member biases movement between the vertebral bones towards a default position and resists vertebral movement away from that position. FIG. 51 illustrates an embodiment in which a cavity 242 is placed within each spinous process abutment member in order to accept a bone forming substance. As noted in previous embodiments, this feature would permit device fusion onto the spinous process of the first vertebral bone. Further, a bone graft or bone graft substitute 252 is positioned so that rod 115 transverses a bore within member 252. This feature permits the establishment of a bony fusion between rod 115 and the lamina or spinous process of the second vertebral bone.

Figure 52:
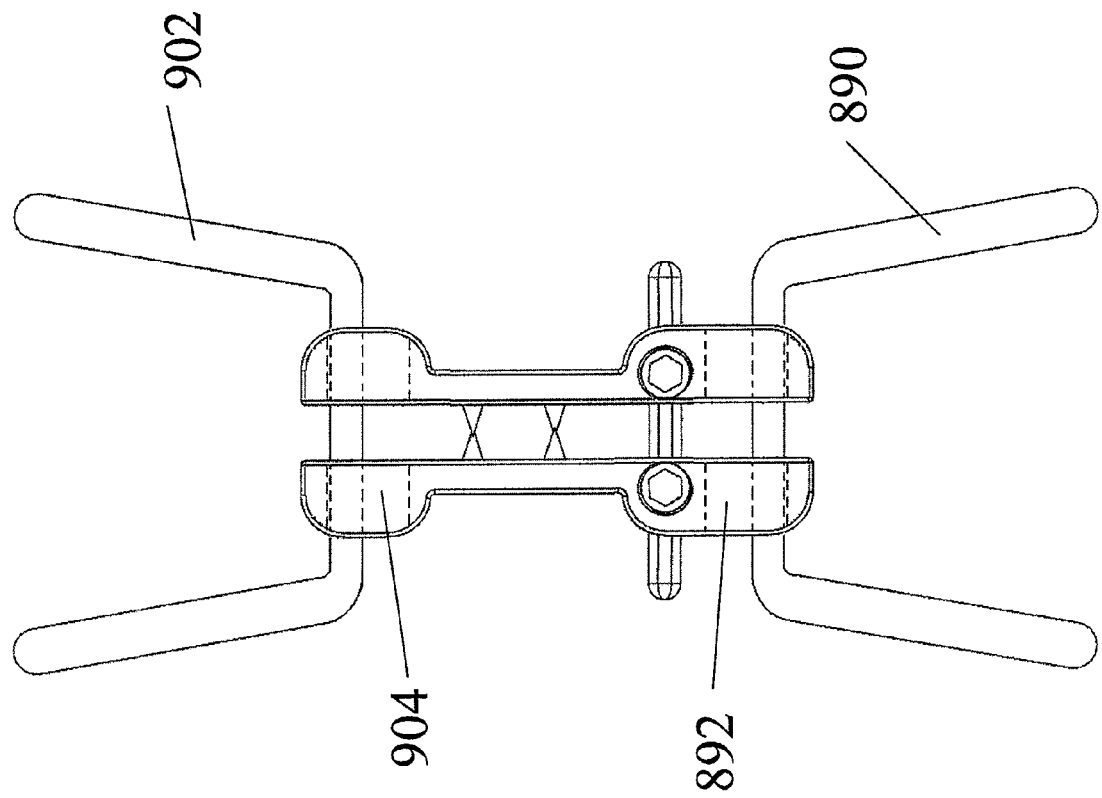
FIGS. 52 and 53 illustrate additional device embodiments.
Figure 53:
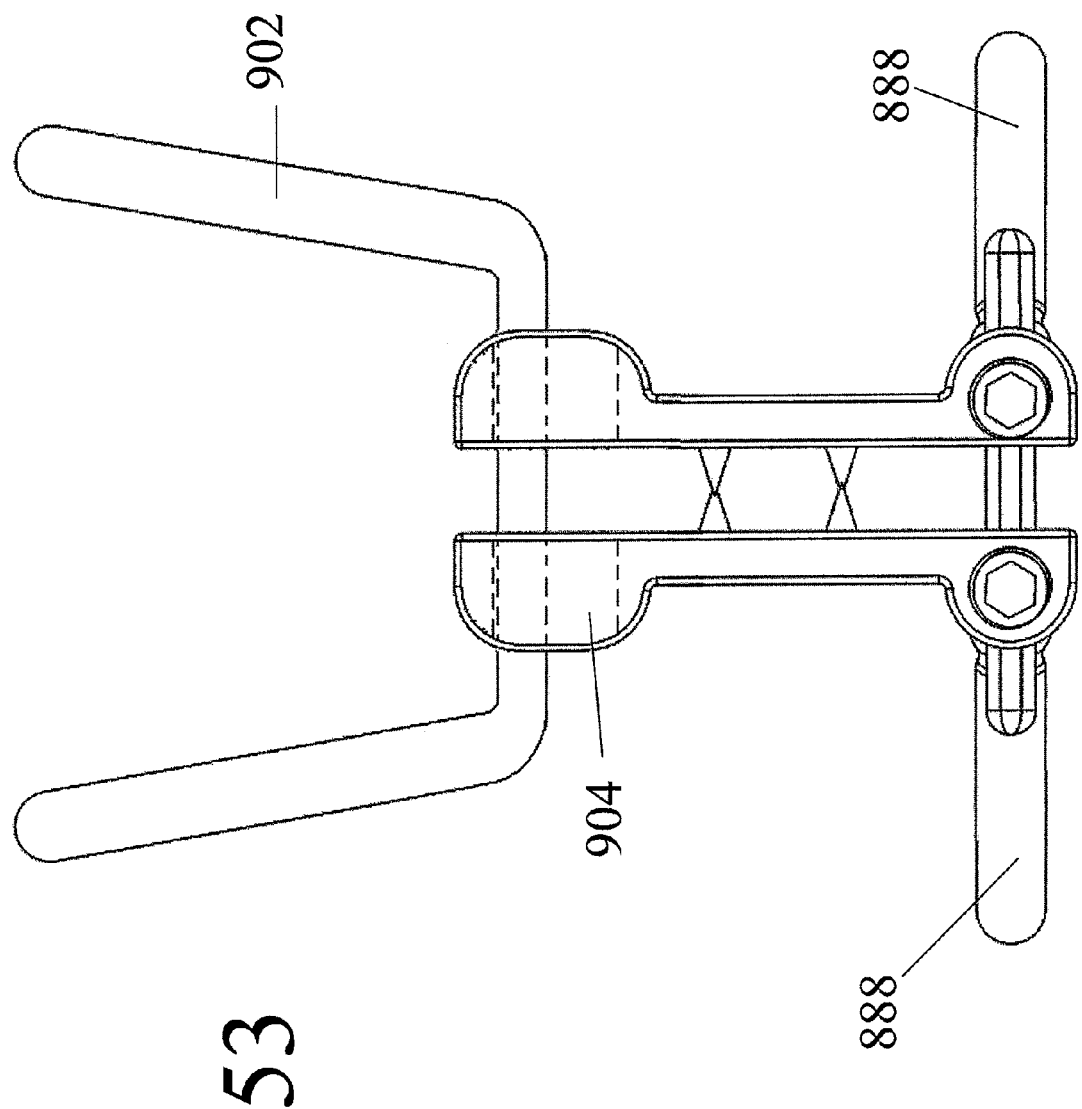

Alternative device embodiments are shown in FIGS. 52 and 53. In either embodiment, the device is adopted to fixate three vertebral bones. In the embodiment of FIG. 52, the device anchors onto the spinous process of the middle vertebral level. Rod 890 is attached to bone fasteners that are anchored into the pedicle portion of the lower vertebral level. Rod 890 is freely movable within slot 892 of the spinous process attachment member. Rod 902 is attached to bone fasteners that are anchored into the pedicle portion of the upper vertebral level. Rod 902 is freely movable within slot 904 of the spinous process attachment member. In the embodiment of FIG. 53, rod 902 is freely movable within slot 904 whereas arms 888 rigidly attach onto the spinous process attachment member using the same mechanism as that shown in FIG. 11. In use, the embodiment of FIG. 53 provides rigid fixation between the middle and lower vertebral levels while permitting movement between the upper and middle vertebral levels.

Figure 56:
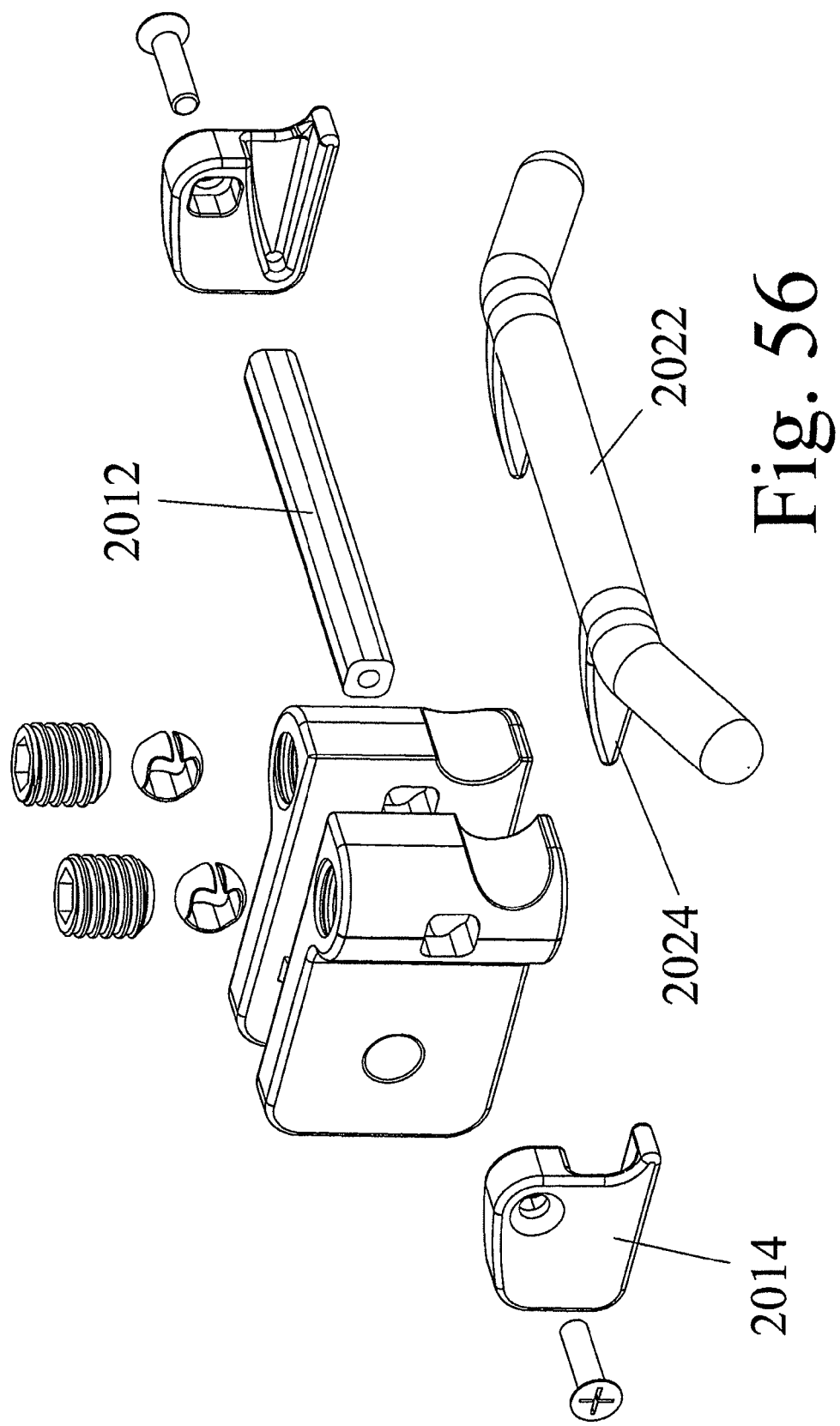
FIG. 56 shows an exploded view.

A perspective view of an additional embodiment is illustrated in FIG. 54. Multiple orthogonal views are shown in FIG. 55 while an exploded, view is shown in FIG. 56. Interconnecting rod 2012 has articulation member 2014 on each end. The spinous process engagement members and the locking mechanism of the device are similar to prior embodiments, such as that of FIG. 45. Rod 2022 is attached to bone fasteners anchored into the pedicle portion of the lower vertebral bone. Rod 2022 has triangular projections 2024 that articulate with articulation members 2014 of rod 2012. The embodiment provides controlled movement between the two vertebral bones.

Figure 57:
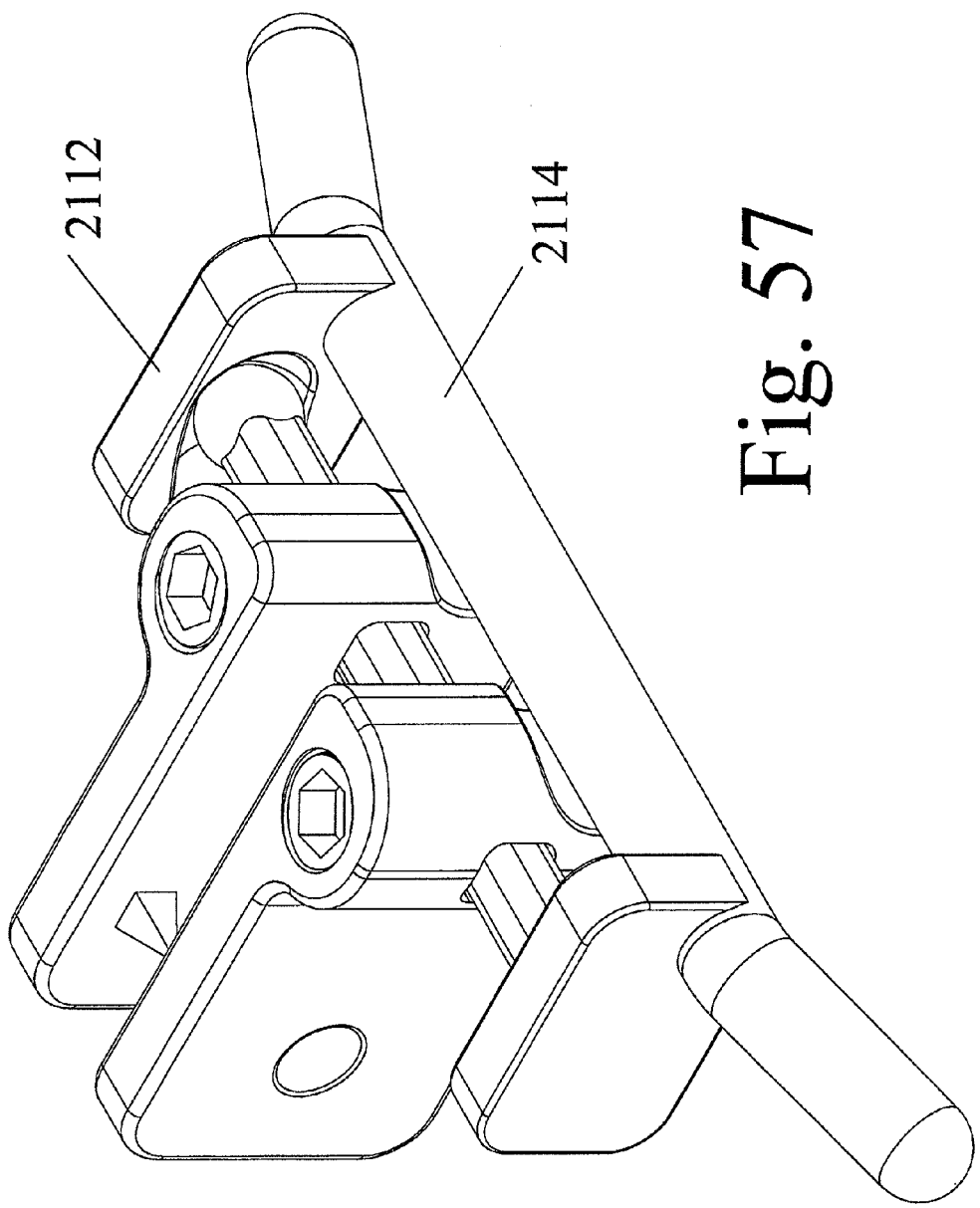
FIG. 57 illustrates an additional device embodiment.
Figure 58:
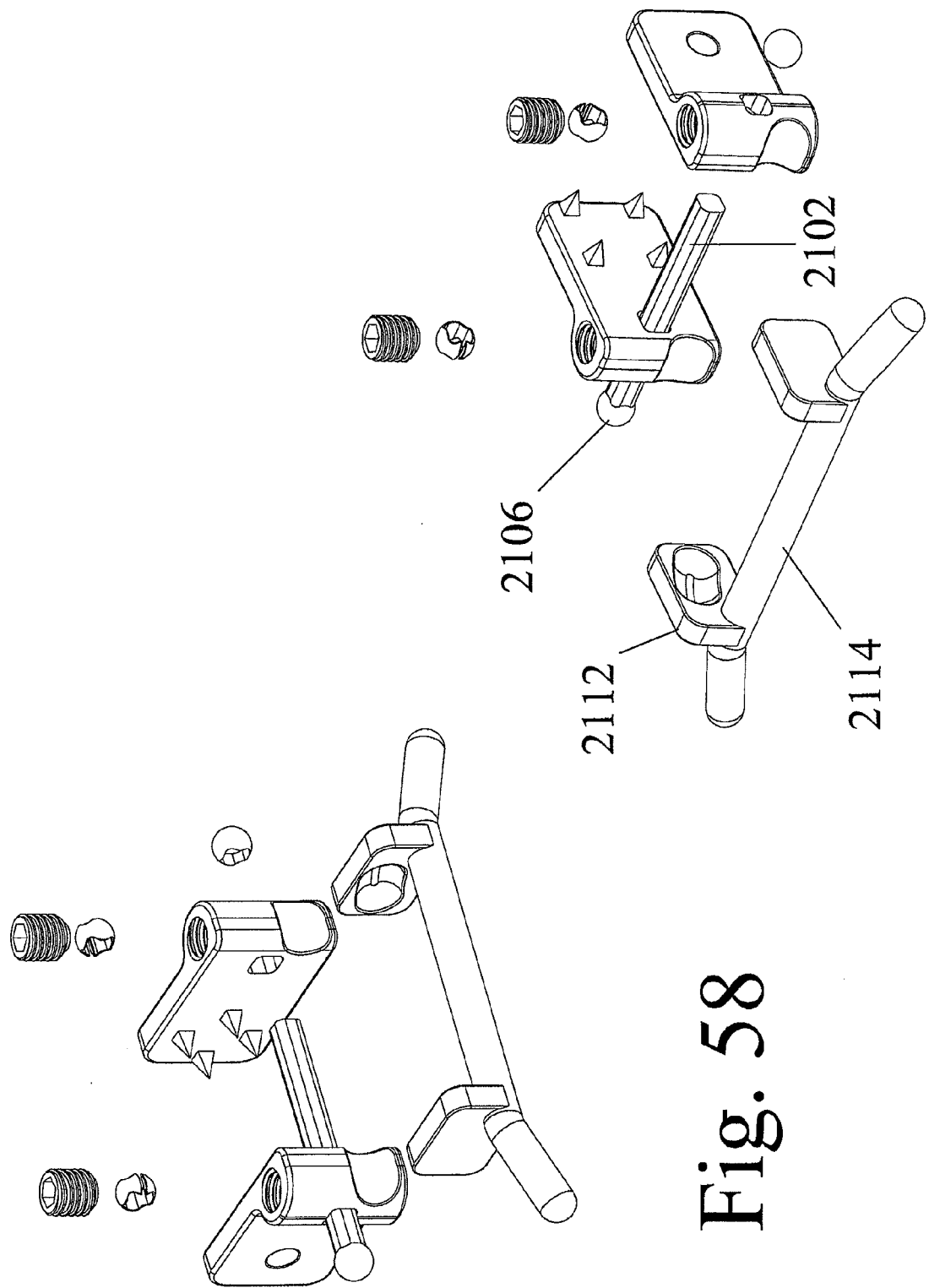
FIG. 58 shows exploded views of the device.
Figure 59:
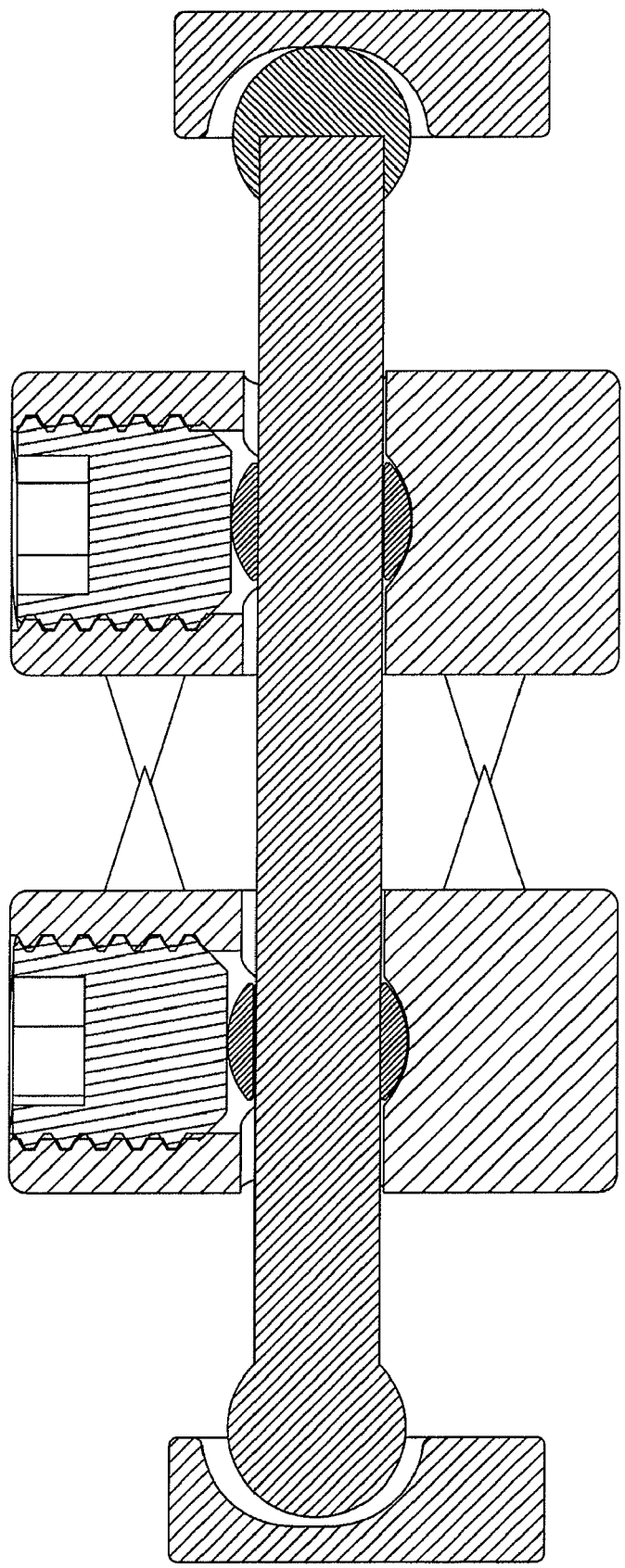
FIG. 59 shows a sectional view through the locking mechanism and articulation surface.

A perspective view of an additional embodiment is shown in FIG. 57. Exploded views are shown in FIG. 58 and a cross-sectional view through the articulation surface is illustrated in FIG. 59. While similar to the prior embodiment, this device employs a different articulation mechanism. Spherical members 2106 are contained at the end of interconnecting rod 2102. Two complimentary articulation surfaces 2112 are attached to rod 2114. As shown in the cross-sectional view, the complimentary articulation surface 2112 contains a depression adapted to accept spherical member 2106 and, preferably, the depression is larger spherical member 2106 so as to permit some additional translational movement. That is, the articulations form a "loose" joint.

Figure 60B:
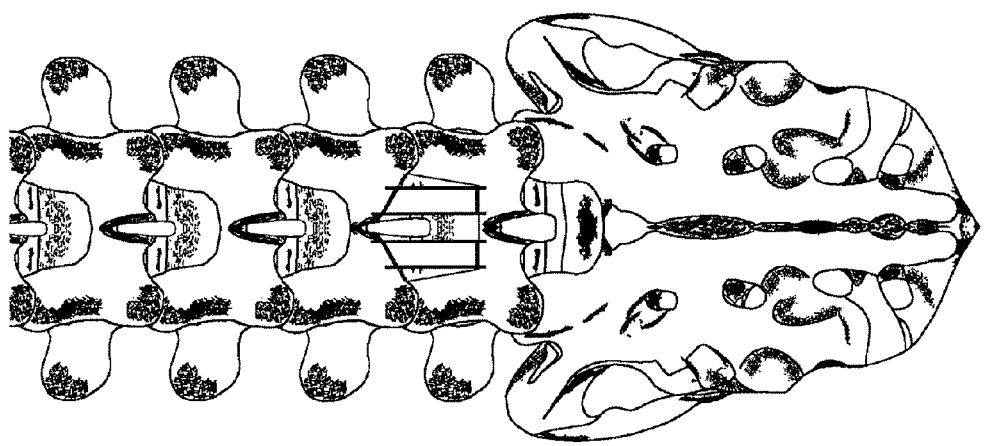
FIG. 60B shows a bone containment implant in place at the L4/5 level.
Figure 60A:
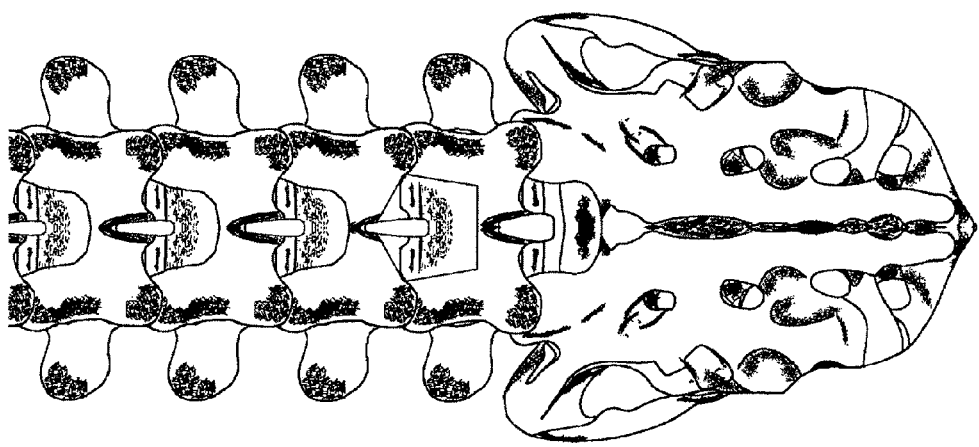
FIG. 60A shows the posterior aspect of a spine.
Figure 61B:
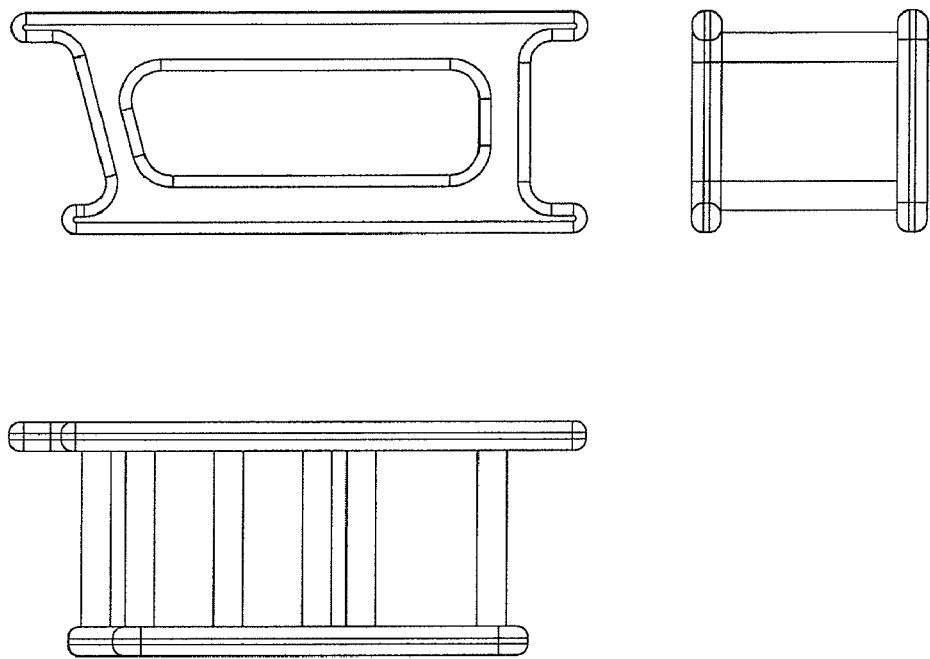
FIG. 61B illustrates the device of FIG. 61A in multiple orthogonal views.
Figure 61A:
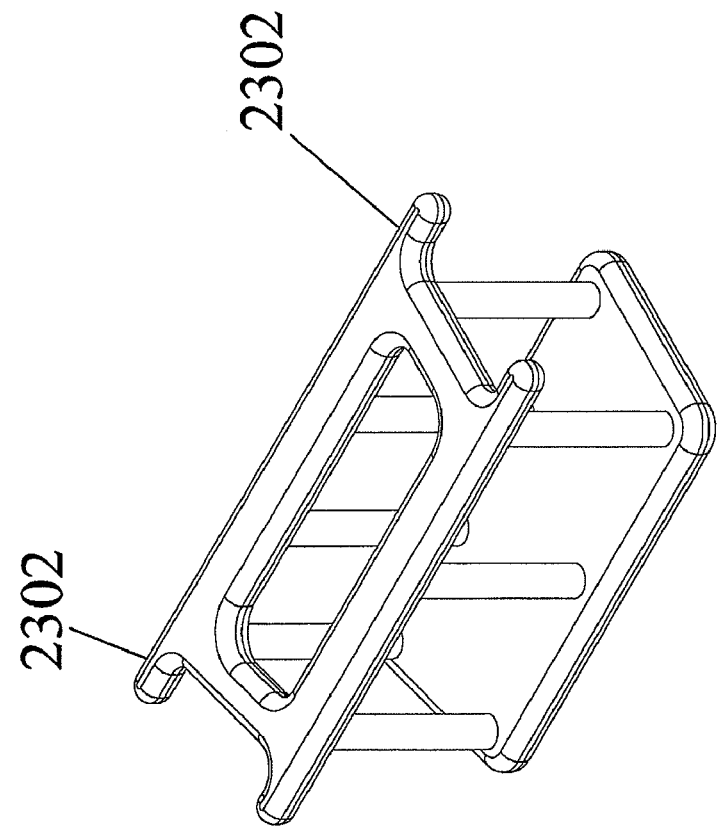
FIG. 61A shows a perspective view of a bone containment implant
Figure 62:
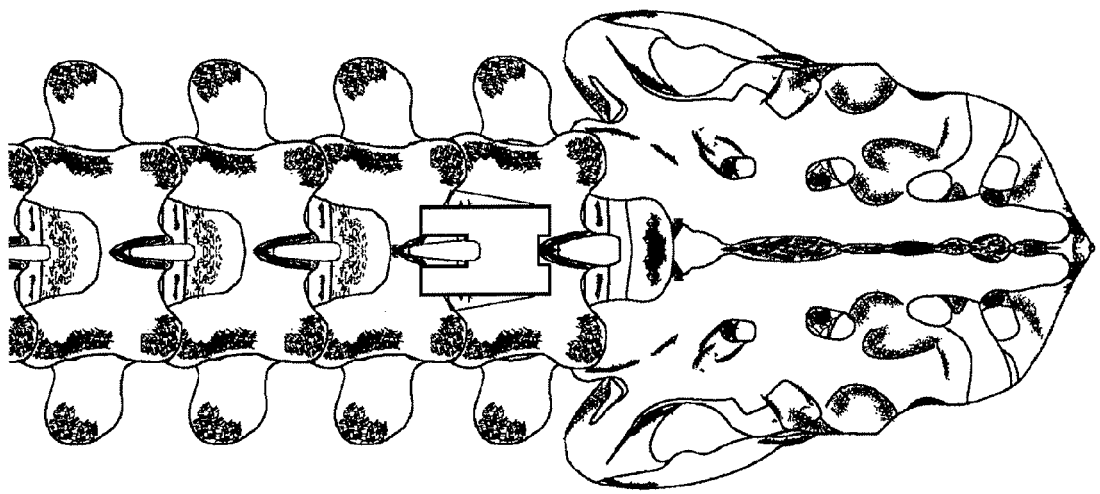
FIG. 62 shows another embodiment of the bone containment implant in place at the L4/5 level.

FIG. 60A illustrates the posterior aspect of spine model whereas FIG. 60B shows the placement of bone forming material between the lamina of the L4 and L5 bones. The bone forming material may be an actual bone graft that is cut to the shape illustrated or a device adapted to contain bone graft or bone graft substitute. FIGS. 61A and B show perspective and orthogonal views of an exemplary graft containment device. As shown, the device preferably has a solid bottom that keeps the contained bone forming material form impinging upon the nerve elements. The sides may be open or solid. The top is preferably open and contains side protrusions 2302 that prevent anterior migration of the device into the spinal canal. An alternative device configuration is shown in FIG. 62. The latter device is intended to cross the vertebral midline, whereas the former is placed on either side of the vertebral midline.

The disclosed devices or any of their components can be made of any biologically adaptable or compatible materials. Materials considered acceptable for biological implantation are well known and include, but are not limited to, stainless steel, titanium, tantalum, shape memory alloys, combination metallic alloys, various plastics, resins, ceramics, biologically absorbable materials and the like. Any components may be also coated/made with osteo-conductive (such as demineralized bone matrix, hydroxyapatite, and the like) and/or osteo-inductive (such as Transforming Growth Factor "TGF-B," Platelet-Derived Growth Factor "PDGF," Bone-Morphogenic Protein "BMP," and the like) bio-active materials that promote bone formation. Further, any surface may be made with a porous ingrowth surface (such as titanium wire mesh, plasma-sprayed titanium, tantalum, porous CoCr, and the like), provided with a bioactive coating, made using tantalum, and/or helical rosette carbon nanotubes (or other nanotube-based materials) in order to promote bone in-growth or establish a mineralized connection between the bone and the implant, and reduce the likelihood of implant loosening. Lastly, the system or any of its components can also be entirely or partially made of a shape memory material or other deformable material.

Although embodiments of various methods and devices are described herein in detail with reference to certain versions, it should be appreciated that other versions, embodiments, methods of use, and combinations thereof are also possible. At a minimum, any feature illustrates in one device embodiment may be alternatively incorporated within any other device embodiment. Therefore the spirit and scope of the appended claims should not be strictly limited to the description of the embodiments contained herein.

The invention claimed is:

1. A method for the fusion of a first vertebral bone and a second vertebral bone of a subject, comprising:
   coupling a first segment of a first distraction member to a spinous process of the first vertebral bone, wherein the first distraction member has a second segment that couples to a distraction device and wherein the distraction device is adapted to deliver a distractive force through the first distraction members to the first vertebral bone;
   coupling a first segment of a second distraction member to the second vertebral bone, wherein the second distraction member has a second segment that couples to the distraction device and wherein the distraction device is adapted to deliver a distractive force through the second distraction members to the second vertebral bone;
   actuating the distraction device and distracting the spinous processes of the first and second vertebral bones away from one another to a distracted position;
   decompressing spinal nerves while the spinous process of the first vertebral bone is coupled to the distraction device and while the first and second vertebral bones are in the distracted position, wherein decompression of the spinal nerves is performed by removing bone and ligament structures that compress the spinal nerves from at least a portion of the lamina of the first vertebral bone or the second vertebral bone;
   using a bone graft or bone graft substitute to span a distance from the lamina of the first vertebral bone to the lamina of the second vertebral bone, wherein the bone graft or bone graft substitute is configured to form a bony fusion between the first and second vertebral bones;
   implanting an orthopedic device to affix the first and second vertebral bones, wherein the orthopedic device contains at least first and second opposed surfaces, wherein at least one of the opposed surfaces contains at least one protrusion that is adapted to penetrate a side surface of the spinous process of the first or second vertebral bone, wherein the orthopedic device also includes a locking member adapted to transition from a first state to a second state, wherein the opposed surfaces are movable relative to one another when the locking member is in the first state and immobilized relative to one another when the locking member is in the second state.

2. A method as in claim 1, wherein implanting the orthopedic device comprises:
   positioning the first opposed surface of the orthopedic device on a first side of the spinous process of the first or second vertebral bone;
   positioning the second opposed surface of the orthopedic device on a side of the spinous process that is opposite to where the first opposed surface is positioned, wherein each of the first and second opposed surfaces is positioned on opposite sides of the same spinous process;
   driving the first and second opposed surfaces of the orthopedic device towards one another and capturing the spinous process between the first and second opposed;
   transitioning the locking member of the orthopedic device from the first state to the second state and immobilizing the first and second opposed surfaces relative to the spinous process.

3. A method as in claim 1, wherein the at least one protrusion from at least one opposed surface is forcibly driven into a side surface of the spinous process when the first and second opposed surfaces of the orthopedic device are driven towards one another.

4. A method as in claim 1, wherein at least one distraction member contains an elongated bone screw having, at the first segment, a threaded shank that is adapted to threadably engage the spinous process.

5. A method as in claim 1, wherein the distraction member contains a threaded shank that positioned into a spinous process along a posterior to anterior axis of the spinous process.

6. A method as in claim 1, wherein the first segment of the first distraction member is positioned more proximal to the spinous process than the second segment of the distraction member when the first distraction member is coupled to the spinous process.

7. A method as in claim 1, wherein at least one distraction member contains a clip member at its first segment, wherein the clip member abuts an outer surface of the spinous process.

8. A method as in claim 1, wherein the implanted orthopedic device attaches to the spinous process of one of the first or second vertebral bones and to threaded fasteners anchored into the other of the first or second vertebral bones.

9. A method as in claim 1, wherein the threaded fasteners are anchored into the pedicle portion of the other vertebral bone.

10. A method as in claim 1, wherein the bone forming material is contained at the site of implantation within a bone graft containment device.

11. A method for the fusion of a first vertebral bone and a second vertebral bone of a subject, comprising:
   coupling a first segment of a first distraction member to a lamina segment of the first vertebral bone, wherein the first distraction member has a second segment that couples to a distraction device, wherein the distraction device is adapted to deliver a distractive force through the first distraction member to the first;
   coupling a first segment of a second distraction member to the second vertebral bone, wherein the second distraction member has a second segment that couples to the distraction device, wherein the distraction device is adapted to deliver a distractive force through the second distraction member to the second vertebral bone;
   actuating the distraction device and distracting the lamina segments of the first and second vertebral bones away from one another to a distracted position;
   decompressing spinal nerves while the lamina segments of the first and second vertebral bones are in the distracted position, wherein the decompression is performed by removing bone and ligament structures that compress the spinal nerves from at least a portion of the lamina of the first vertebral bone or the second vertebral bone;
   using a bone graft or bone graft substitute to span a distance from the lamina of the first vertebral bone to the lamina of the second vertebral bone, wherein the bone graft or bone graft substitute is intended to form a bony fusion between the first and second vertebral bones;
   implanting an orthopedic device to affix the first and second vertebral bones, wherein the orthopedic device contains at least first and a second opposed surfaces, wherein at least one opposed surface contains at least one protrusion adapted to penetrate a side surface of the spinous process of the first or second vertebral bone, wherein the orthopedic device also contains a locking member adapted to transition from a first state to a second state, wherein the opposed surfaces are movable relative to one another when the locking member is in the first state and immobilized relative to one another when the locking member is in the second state.

12. A method as in claim 11, wherein implanting the orthopedic device comprises:

positioning the first opposed surfaces of the orthopedic device on a first side of the spinous process of the first or second vertebral bone;

positioning the second opposed surface of the orthopedic device on a side of the spinous process that is opposite to where the first opposed surface is positioned, wherein each of the first and second opposed surfaces are positioned on opposite sides of the same spinous process;

driving the first and second opposed surfaces of the orthopedic device towards one another and capturing the spinous process between the opposed surfaces, wherein the at least one protrusion from at least one opposed surface is forcibly driven into a side surface of the spinous process;

transitioning the locking member of the orthopedic device from the first state to the second state and immobilizing the first and second opposed surfaces relative to the spinous process positioned between the first and second opposed surfaces.

13. A method as in claim 11, wherein at least one of the distraction members contains a clip member at its first segment, wherein the clip member abuts an outer surface of a lamina surface of the first or second vertebral bone.

14. A method as in claim 11, wherein the implanted orthopedic device attaches to the spinous process of one vertebral bone and to threaded fasteners anchored into the other vertebral bone.

15. A method as in claim 14, wherein the threaded fasteners are anchored into the pedicle portion of the other vertebral bone.

16. A method as in claim 11, wherein the bone forming material is positioned to span the distance from the lamina of the first vertebral bone to the lamina of the second vertebral bone and further positioned to cross the vertebral midline.

17. A method as in claim 11, wherein the bone graft or bone graft substitute is contained at the site of implantation within a bone graft containment device.

18. A method for the implantation of non-fusion orthopedic implants within a vertebral column, comprising:

coupling a first segment of a first distraction member to a spinous process of a first vertebral bone, wherein the first distraction member has a second segment that couples to a distraction device, wherein the distraction device is adapted to deliver a distractive force through the first distraction member to the first vertebral bone;

coupling a first segment of a second distraction member to a second vertebral bone, wherein the second distraction member has a second segment that couples to the distraction device, wherein the distraction device is adapted to deliver a distractive force through the second distraction member to the second vertebral bone;

actuating the distraction device and distracting the spinous processes of the first and second vertebral bones away from one another to a distracted position;

decompressing a spinal nerves while the spinous process of the first and second vertebral bones are coupled to the distraction device and in the distracted position, wherein the decompression is performed by removing bone and ligament structures that compress the spinal nerves from at least a portion of the lamina of the first vertebral bone or the second vertebral bone;

implanting an orthopedic device to affix onto the first and second vertebral bones, wherein the orthopedic device contains at least first and second opposed surfaces, wherein at least one of the opposed surfaces contains at least one protrusion adapted to penetrate a side surface of the spinous process of the first or second vertebral bone, wherein the orthopedic device also contains a locking member adapted to transition from a first state to a second state, wherein the opposed surfaces are movable relative to one another when the locking member is in the first state and immobilized relative to one another when the locking member is in the second state.

19. A method as in claim 18, wherein implanting the orthopedic device comprises:

positioning the first opposed surfaces of the orthopedic device on a first side of the spinous process of the first or second vertebral bone;

positioning the second opposed surface of the orthopedic device on a side of the spinous process that is opposite to where the first opposed surface is positioned, wherein each of the first and second opposed surfaces are positioned on opposite sides of the same spinous process;

driving the first and second opposed surfaces of the orthopedic device towards one another and capturing the spinous process between the opposed surfaces;

transitioning the locking member of the orthopedic device from the first state to the second state and immobilizing the first and second opposed surfaces relative to the spinous process.

20. A method as in claim 18, wherein the implanted orthopedic device attaches to the spinous process of one vertebral bone and to threaded fasteners anchored into the other vertebral bone.

* * * * *